US011905253B2

(12) United States Patent
Vacher et al.

(10) Patent No.: US 11,905,253 B2
(45) Date of Patent: Feb. 20, 2024

(54) COMPOUNDS AND PHARMACEUTICAL COMPOSITIONS FOR REDUCING CD95-MEDIATED CELL MOTILITY

(71) Applicants: INSTITUT NATIONAL DE LA SANTE ET DE LA RECHERCHE MEDICALE (INSERM), Paris (FR); UNIVERSITE DE RENNES 1, Rennes (FR); CENTRE HOSPITALIER UNIVERSITAIRE DE BORDEAUX, Talence (FR); INSTITUT BERGONIE, Bordeaux (FR); CENTRE NATIONAL DE LA RECHERCHE SCIENTIFIQUE (CNRS), Paris (FR); UNIVERSITE DE BORDEAUX, Bordeaux (FR)

(72) Inventors: Pierre Vacher, Bordeaux (FR); Patrick Legembre, Rennes (FR); Mickael Jean, Rennes (FR); Patrick Blanco, Bordeaux (FR); Pierre Van De Weghe, Rennes (FR)

(73) Assignees: INSTITUT NATIONAL DE LA SANTE ET DE LA RECHERCHE MEDICALE (INSERM), Paris (FR); UNIVERSITE DE RENNES 1, Rennes (FR); CENTRE HOSPITALIER UNIVERSITAIRE DE BORDEAUX, Talence (FR); INSTITUT BERGONIE, Bordeaux (FR); CENTRE NATIONAL DE LA RECHERCHE SCIENTIFIQUE (CNRS), Paris (FR); UNIVERSITE DE BORDEAUX, Bordeaux (FR)

( * ) Notice: Subject to any disclaimer, the term of this patent is extended or adjusted under 35 U.S.C. 154(b) by 0 days.

(21) Appl. No.: 17/049,680

(22) PCT Filed: Apr. 19, 2019

(86) PCT No.: PCT/EP2019/060242
§ 371 (c)(1),
(2) Date: Oct. 22, 2020

(87) PCT Pub. No.: WO2019/206834
PCT Pub. Date: Oct. 31, 2019

(65) Prior Publication Data
US 2021/0238143 A1 Aug. 5, 2021

(30) Foreign Application Priority Data

Apr. 23, 2018 (EP) ..................... 18305500

(51) Int. Cl.
C07D 233/64 (2006.01)
A61P 37/00 (2006.01)
A61K 45/06 (2006.01)

(52) U.S. Cl.
CPC ............ *C07D 233/64* (2013.01); *A61K 45/06* (2013.01); *A61P 37/00* (2018.01)

(58) Field of Classification Search
None
See application file for complete search history.

(56) References Cited

PUBLICATIONS

Hu, Yaogang, "Design and synthesis of AApeptides: A new class of peptide mimics." Bioorganic & Medicinal Chemistry Letters, 21(5), 2011, 1469-1471.*

* cited by examiner

*Primary Examiner* — Samantha L Shterengarts
(74) *Attorney, Agent, or Firm* — WCF IP

(57) ABSTRACT

The present invention relates the field of reducing CD95-mediated cell motility in a subject, in particular for their use in the reduction of CD-95 mediated cancer cell motility, the reduction of CD95-mediated lymphocyte motility and/or B cell maturation, or the treatment of B-cell tumors, in a subject. The inventors identified a novel family of compounds having the ability to disrupt CD95/PLCγ1 interaction and to neutralize the CD95-mediated calcium signaling pathway and cell migration in human peripheral blood lymphocytes (PBLs) and Th17 cells. Thus, the present invention relates to compounds of formula (A) as defined in the present text, to a pharmaceutical composition comprising said compounds in a pharmaceutically acceptable medium and to the use of these compounds and compositions as medicament, in particular for their use in the reduction or treatment of the above-mentioned pathologies, and in particular in the treatment of cancers and autoimmune inflammatory disease such as systemic lupus erythematosus, inflammatory condition and Th17-mediated disease.

Figure 1A:
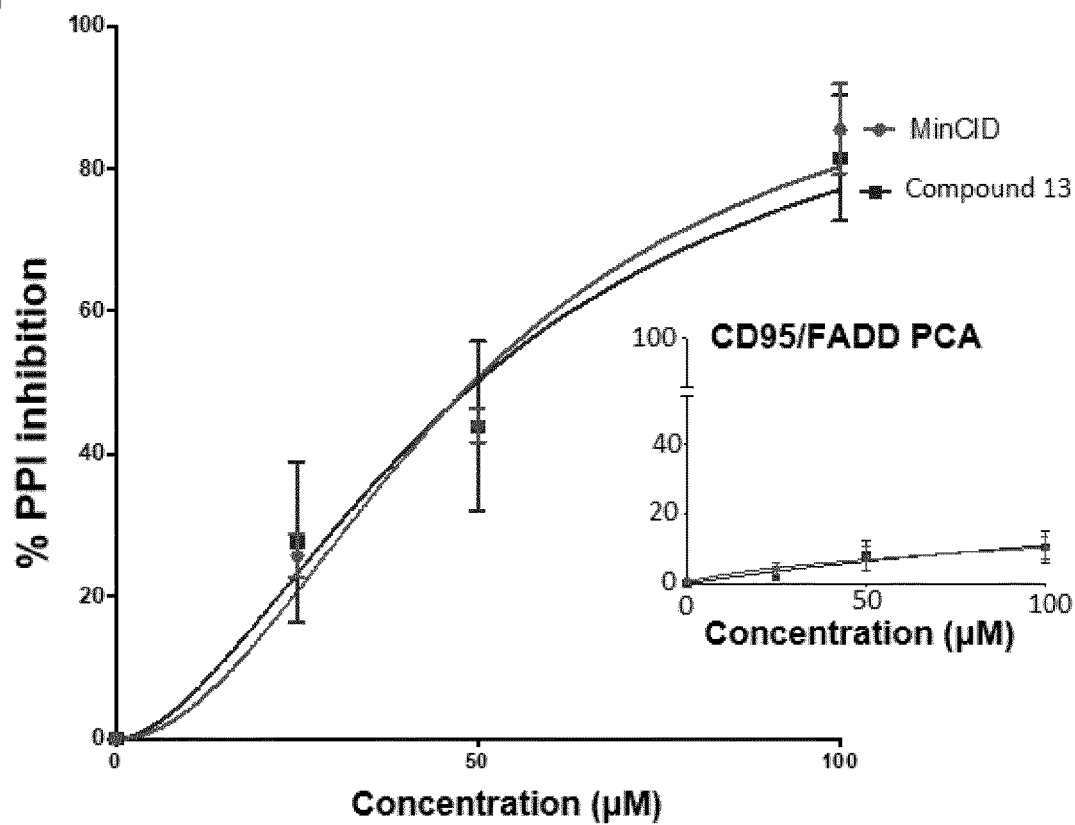

19 Claims, 12 Drawing Sheets
Specification includes a Sequence Listing.

SEQUENCE LISTING

<160> NUMBER OF SEQ ID NOS: 1

<210> SEQ ID NO 1
<211> LENGTH: 7
<212> TYPE: PRT
<213> ORGANISM: Homo sapiens
<220> FEATURE:
<223> OTHER INFORMATION: minCID corresponding to amino acids 182-188 of
      human CD95

<400> SEQUENCE: 1

Thr Cys Arg Lys His Arg Lys
1               5

COMPOUNDS AND PHARMACEUTICAL COMPOSITIONS FOR REDUCING CD95-MEDIATED CELL MOTILITY

FIELD OF THE INVENTION

The present invention relates to novel compounds and to their use for reducing CD95-mediated cell motility in a subject.

More particularly, the present invention relates to novel compounds, and compositions comprising them, for their use in:
- the reduction of CD95 mediated cancer cell motility;
- the reduction of CD95-mediated lymphocyte motility and/or B cell maturation, in particular its use in the treatment of systemic lupus erythematosus; or
- the treatment of B-cell tumors, such as multiple myeloma and chronic lymphocytic leukemia;

in a subject.

BACKGROUND OF THE INVENTION

Chronic inflammatory diseases (IDs) are the third cause of death in developed countries, after cancer and cardiovascular disorders, and their prevalence is growing in developed countries. These diseases constitute a heterogeneous group of illnesses, including autoimmune systemic diseases (systemic lupus erythematosus, systemic sclerosis (SSc)) and inflammatory bowel disorders. All these diseases appear clinically different, but in fact share many similarities, from common genetic background, common pathophysiological pathways, and not surprisingly similar treatments. From a pathogenic point of view, these IDs are usually characterized first by an autoimmune response, characterized by a breakdown of tolerance and the presence of circulating autoantibodies. Those antibodies are secreted by B cells, which have been activated by a specific subset of effector CD4+ T cells, follicular helper T cells (Tfh). Second, tissue lesions responsible for the clinical presentations involve the IL17-secreting T cells (Th17), which once recruited in the organs trigger robust inflammation. Therefore, understanding the signals governing the fate of effector T cells is of tremendous importance to identify new therapeutic targets and small molecules that interact selectively them.

Systemic Lupus Erythematosus (SLE) is a chronic autoimmune disease characterized by a loss of tolerance toward nuclear components leading to autoantibody production, immune complex formation and organ/tissue damage. Human studies and murine models indicate a role for Th17, and Tfh in SLE progression (Shin, M. S. et al. Curr Opin Rheumatol. 2011, 23, 444-448).

CD95L (FasL) belongs to the Tumor Necrosis Factor (TNF) family and is the ligand of the death receptor CD95 (also known as Fas). While CD95 is ubiquitously expressed on healthy cells, CD95L exhibits a restricted expression pattern, mainly detected at the surface of lymphocytes, where it plays a pivotal role in the elimination of infected and transformed cells (Strasser, A. et al. Immunity. 2009, 30, 180-192). CD95L is a transmembrane glycoprotein that acts locally through cell-to-cell contact (Suda, T. et al. Cell. 1993, 75, 1169-1178.) and after cleavage by metalloproteases such as MMP3 (Matsuno, H. et al. J Rheumatol. 2001, 28, 22-28), MMP7 (Vargo-Gogola, T. et al. Arch Biochem Biophys. 2002, 408, 155-161.), MMP9 (Kiaei, M. et al. Exp Neurol. 2007, 205, 74-81) or A Disintegrin And Metalloproteinase 10 (ADAM-10) (Kirkin, V. et al. Cell Death Differ. 2007, 14, 1678-1687 and Schulte, M. et al. Cell Death Differ. 2007, 14, 1040-1049), a soluble CD95L (cleaved CD95L or cl-CD95L or s-CD95L) is released into the bloodstream. This soluble ligand contributes to aggravate inflammation in chronic inflammatory disorders such as systemic lupus erythematosus (SLE) (O'Reilly, L. A. et al. Nature. 2009, 461, 659-663 and Tauzin, S. et al. PLoS Biol. 2011, 9, e1001090) by inducing non-apoptotic signaling pathways such as NF-κB (O'Reilly, K. E. et al. Cancer Res. 2006, 66, 1500-1508) and PI3K (Tauzin, S. et al. PLoS Biol. 2011, 9, e1001090) and may exert pro-oncogenic functions by promoting the survival of ovarian and liver cancers and chemotherapy resistance of lung cancers.

CD95L receptor, designated CD95 or Fas, carries an intracellular conserved stretch, the death domain (DD), which serves as a docking platform to trigger cell death. Binding of membrane-bound hexameric CD95L to CD95 leads to the recruitment of the adaptor protein FADD (Fas Associated Death Domain) through homotypic interactions via their respective DD (Holler, N. et al. Mol Cell Biol. 2003, 23, 1428-1440). FADD in turn aggregates the initiator caspase-8 and caspase-10. The CD95/FADD/caspase complex is called death-inducing signalling complex (DISC) and leads to the elimination of cancer cells through an apoptotic mechanism (Kischkel, F. C. et al. Embo J. 1995, 14, 5579-5588.). By contrast, homotrimeric cl-CD95L fails to induce DISC formation, but instead triggers the formation of a non-apoptotic complex termed motility-inducing signaling complex (MISC) implementing a $Ca^{2+}$ response (Tauzin, S. et al. PLoS Biol. 2011, 9, e1001090; Kleber, S. et al. Cancer Cell. 2008, 13, 235-248 and Malleter, M. et al. Cancer Res. 2013, 73, 6711-6721). Recent data from our group highlighted that cl-CD95L induces a calcium response by inducing the direct interaction of CD95 with PLCγ1 (Poissonnier, A. et al. Immunity. 2016, 45, 209-223).

Indeed, in presence of cl-CD95L, the juxtamembrane region of CD95, called calcium-inducing domain (CID), recruits PLCγ1 to induce endothelial transmigration of Th17 cells in SLE (Poissonnier, A. et al. Immunity. 2016, 45, 209-223). Moreover, a peptide consisting of the CID conjugated to the cell-penetrating domain of TAT, namely TAT-CID, binds PLCγ1 and prevents its recruitment to CD95. Strikingly, repeated injections of TAT-CID in lupus-prone mice ($MRL^{Lpr/+}$) block endothelial transmigration of Th17 cells and alleviate clinical symptoms (Poissonnier, A. et al. Immunity. 2016, 45, 209-223).

Accordingly, compounds that are able to reduce CD95-meditated cell motility are highly desirable, in particular in the treatment of cancers and autoimmune inflammatory diseases such as systemic lupus erythematosus, inflammatory condition and Th17-mediated disease.

There is thus a need for novel compounds able to reduce CD95-mediated cell motility in a subject.

There is also a need for novel compounds able to reduce CD95-mediated cancer cell motility in a subject.

There is furthermore a need for novel compounds able to treat cancer in a subject.

There is also a need for novel compounds able to reduce CD95-mediated lymphocyte motility and/or B cell maturation in a subject.

There is also a need for novel compounds able to treat an auto-immune inflammatory disease, in particular able to treat systemic lupus erythematosus.

There is furthermore a need for novel compounds able to treat antibody-mediated diseases, including but not limited to graft rejection, graft vs host disease, and inflammatory-autoimmune diseases. B-cell tumors, such as multiple myeloma and chronic lymphocytic leukemia.

There is moreover a need for novel compounds able to treat B-cell tumors, such as multiple myeloma and chronic lymphocytic leukemia.

SUMMARY OF THE INVENTION

The present invention relates to compounds, pharmaceutical compositions comprising them and to their uses thereof for reducing CD95-mediated cell motility.

According to the inventor's experimental results, the presently claimed compounds are surprisingly able to reduce CD95-mediated cell motility, and in particular to alleviate clinical symptoms in lupus-prone mice and to reduce Th17 trafficking to inflamed kidneys of lupus-prone mice.

Accordingly, one of the objects of the present invention relates to a compound of formula (A):

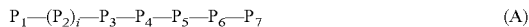
$$P_1-(P_2)_i-P_3-P_4-P_5-P_6-P_7 \quad (A)$$

wherein:
i represents 0 or 1,
with the proviso that when i represents 0, $P_1$ is directly bounded to $P_3$;
$P_1$ is selected from the group consisting of a hydrogen atom, a —$NH_2$ group and the following structures of formulae (I) and (II):

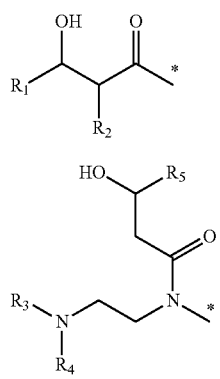

wherein:
$R_1$, $R_3$, $R_4$ and $R_5$ independently represent a hydrogen atom, a linear or branched ($C_1$-$C_{20}$)alkyl group, an aryl group or a linear or branched ($C_1$-$C_6$)alkoxy group;
$R_2$ represents a hydrogen atom or a —$NH_2$ group; and
\* represents the bound with $P_2$ or, when i represents 0, with $P_3$;
$P_2$ is selected from the group consisting of the following structures of formulae (III) and (IV):

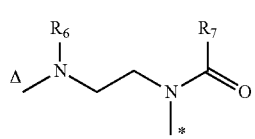

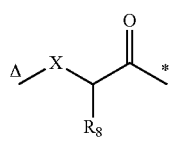

wherein:
$R_6$ represents an hydrogen atom or a linear or branched ($C_1$-$C_{20}$)alkyl group; $R_7$ represents a linear or branched ($C_1$-$C_{20}$)alkyl group, a linear or branched ($C_1$-$C_6$)alkoxy group, or an aryl group, $R_7$ being optionally substituted with one or several radical(s) independently selected from the group consisting of —OH, —$NH_2$, —SH and an amide group;
$R_8$ represents a linear or branched ($C_1$-$C_{20}$)alkyl group, a linear or branched ($C_1$-$C_6$)alkoxy group, or an aryl group, $R_8$ being optionally substituted with one or several radical(s) independently selected from the group consisting of —OH, —SH, —$NH_2$ and an amide group;
X represents a single bound or —N($R_6$)—, $R_6$ being as defined previously;
Δ represents the bound with $P_1$ and \* represents the bound with $P_3$;
$P_3$ is selected from the group consisting of the following structures of formulae (V), (VI), (VII) and (VIII):

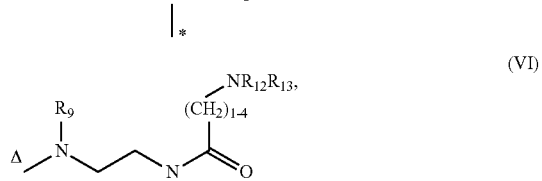

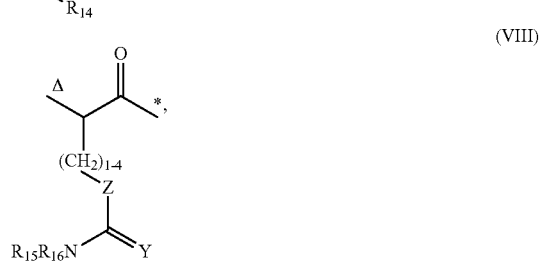

wherein:
$R_9$ represents a hydrogen atom or an alkyl group;
$R_{10}$, $R_{11}$; $R_{12}$; $R_{13}$; $R_{15}$ and $R_{16}$ independently represent a hydrogen atom or a linear or branched ($C_1$-$C_{20}$)alkyl group;
$R_{14}$ represents an aryl group, a heteroaryl group or a —$NR_{17}R_{18}$ group, wherein $R_{17}$ and $R_{18}$ independently represent a hydrogen atom or a linear or branched ($C_1$-$C_{20}$)alkyl group;
Y independently represents NH, O, S or $CH_2$;
Z independently represents —NH—, —N($CH_3$)—, —S— or —$CH_2$—;

Δ represents the bound with P$_2$ when i represent 1 or with P$_1$ when i represents 0, and * represents the bound with P$_4$;

P$_4$ is selected from the group consisting of the following structures of formulae (IX), (X) and (XI):

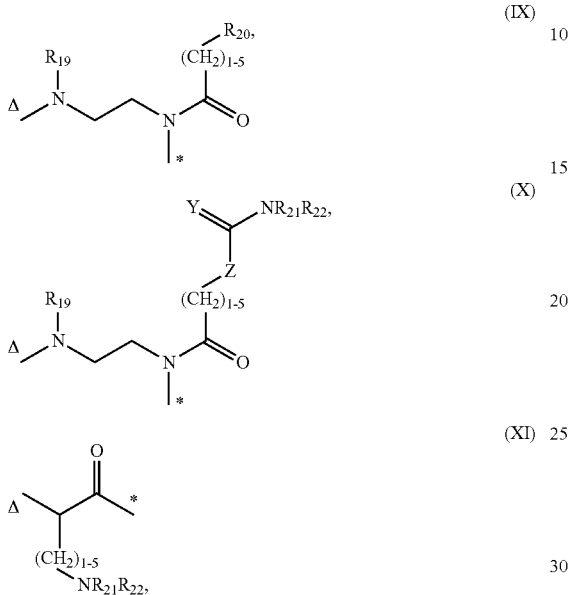

wherein:
- R$_{19}$ independently represents a hydrogen atom or a linear or branched (C$_1$-C$_{20}$)alkyl group;
- R$_{20}$ represents an aryl group, an heteroaryl group or a —NR$_{21}$R$_{22}$ group, the aryl or heteroaryl group being optionally substituted with one or several —OH group(s);
- R$_{21}$ and R$_{22}$ independently represent a hydrogen atom or a linear or branched (C$_1$-C$_{20}$)alkyl group;
- Y independently represents NH, O, S or CH$_2$;
- Z independently represents —NH—, —N(CH$_3$)—, —S— or —CH$_2$—;
- Δ represents the bound with P$_3$ and * represents the bound with P$_5$;
- P$_5$ is selected from the group consisting of the following structures of formulae (XII) and (XIII):

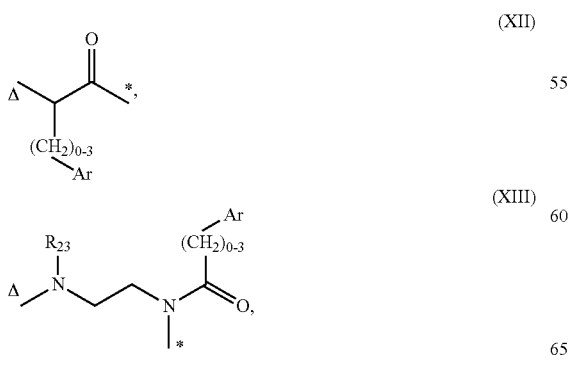

wherein:
- R$_{23}$ represents a hydrogen atom or a linear or branched (C$_1$-C$_{20}$)alkyl group;
- Ar represents an aryl or heteroaryl group, optionally substituted with one or several radical(s) independently selected from the group consisting of —OH, —SH, —NH$_2$ and an amide group;
- Δ represents the bound with P$_4$ and * represents the bound with P$_6$;
- P$_6$ is selected from the group consisting of the following structures of formulae (XIV), (XV), (XVI), (XVII) and (XVIII):

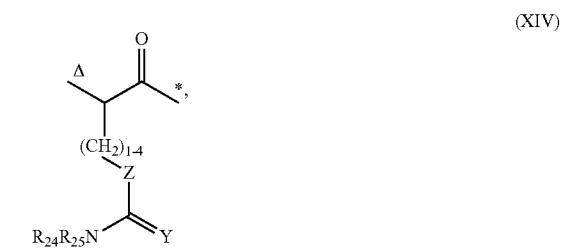

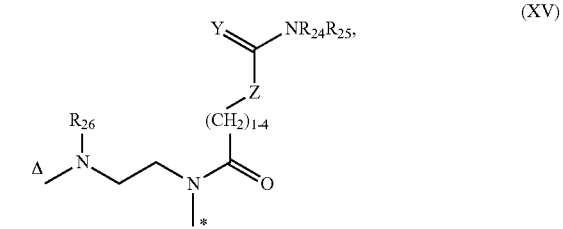

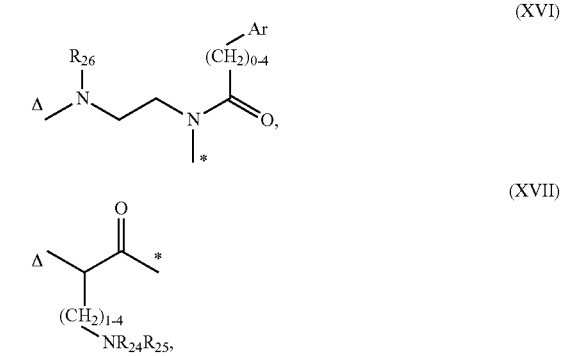

wherein:
- R$_{24}$, R$_{25}$ and R$_{26}$ independently represent a hydrogen atom or a linear or branched (C$_1$-C$_{20}$)alkyl group;
- Ar represents an aryl or heteroaryl group, optionally substituted with one or several radical(s) independently selected from the group consisting of —OH, —NH$_2$, —SH and an amide group;
- Y independently represents NH, O, S or CH$_2$;
- Z independently represents —NH—, —N(CH$_3$)—, —S— or —CH$_2$—;
- Δ represents the bound with P$_5$ and * represents the bound with P$_7$;
- P$_7$ is selected from the group consisting of the following structures of formulae (XIX) and (XX):

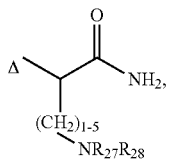

(XIX)

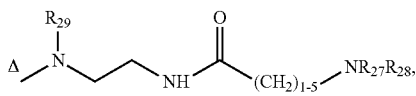

(XX)

wherein:
$R_{27}$, $R_{28}$ and $R_{29}$ independently represent a hydrogen atom or a linear or branched $(C_1-C_{20})$alkyl group, and
Δ represents the bound with $P_6$,
or one of its salts;
said compound of formula (A) being in all the possible racemic, enantiomeric and diastereoisomeric isomer forms.

In a particular embodiment, $P_1$ is such that:
$R_1$ and $R_5$ independently represent a $C_1-C_3$ alkyl group, and in particular both represent —$CH_3$; and
$R_3$ and $R_4$ represent a hydrogen atom.

In another embodiment, $P_2$ is such that:
$R_6$ represents a hydrogen atom;
$R_7$ represents a linear or branched $(C_1-C_{20})$alkyl group, in particular a linear $(C_1-C_{20})$alkyl group, optionally substituted with one or several, in particular one, radical(s) selected from the group consisting of —SH, —OH and a —C(O)NH$_2$ group; and
$R_8$ represents a $(C_1-C_3)$alkyl group, preferably substituted with one or several, in particular one, —SH group(s).

In a particular embodiment, $P_3$ is selected from the group consisting of formulae (V), (VII) or (VIII).

In an embodiment of the invention, $P_3$ is such that:
$R_9$, $R_{10}$, $R_{11}$, $R_{15}$ and $R_{16}$ represent a hydrogen atom;
Z represents —NH—;
Y represents NH; and
$R_{14}$ represents an aryl group or a heteroaryl group, in particular an indole or a pyridine group.

In a particular embodiment, $P_4$ is such that:
$R_{19}$, $R_{21}$ and $R_{22}$ represent a hydrogen atom;
$R_{20}$ represents a —NH$_2$ group, an indole group, an indoline group or a phenyl group, said indole, indoline or phenyl group being optionally substituted with one or several, in particular one, —OH group(s); and
Z represents —NH— and Y represents NH, or Z represents —CH$_2$— and Y represents O.

In a particular embodiment, $P_5$ is such that Ar represents an imidazole group.

In a particular embodiment of the invention, $P_6$ is selected from the group consisting of formulae (XIV), (XV) or (XVI).

In an embodiment of the invention, $P_6$ is such that:
$R_{24}$, $R_{25}$ and $R_{26}$ represent a hydrogen atom;
Ar represents a phenyl or an indole group, optionally substituted with a —OH or —NH$_2$ group; and
Z represents —NH— and Y represents NH, or Z represents —CH$_2$— and Y represents O.

In a particular embodiment, $P_7$ is such that $R_{27}$, $R_{28}$ and $R_{29}$ represent a hydrogen atom.

In a particular embodiment, a compound of the invention is of formula (A'):

wherein:
$P_1$ represents a structure of formula (I), with preferably $R_1$ being a hydrogen atom; and $R_2$ a —NH$_2$ group;
$P_2$ represents a structure of formula (III), with preferably $R_6$ being a hydrogen atom; and $R_7$ an alkyl group substituted with a —SH group;
$P_4$ represents the structure of formula (IX), with preferably $R_{19}$ being a hydrogen atom and $R_{20}$ being a —NH$_2$ group; $P_5$ represents a structure of formula (XII), with preferably Ar being an imidazole group;
$P_6$ represents a structure of formula (XV), with preferably $R_{24}$, $R_{25}$ and $R_{26}$ being a hydrogen atom; Y being NH—; and Z being —NH—;
$P_7$ represents a structure of formula (XIX), with preferably $R_{27}$ and $R_{28}$ being a hydrogen atom; and
$P_3$ represents a structure of:
formulae (VII), with preferably $R_{14}$ being an indole, or formula (VIII), with preferably Z being —NH—, Y being NH and $R_{15}$ and $R_{16}$ being a hydrogen atom.

In a particular embodiment, a compound according to the invention is selected from formula:

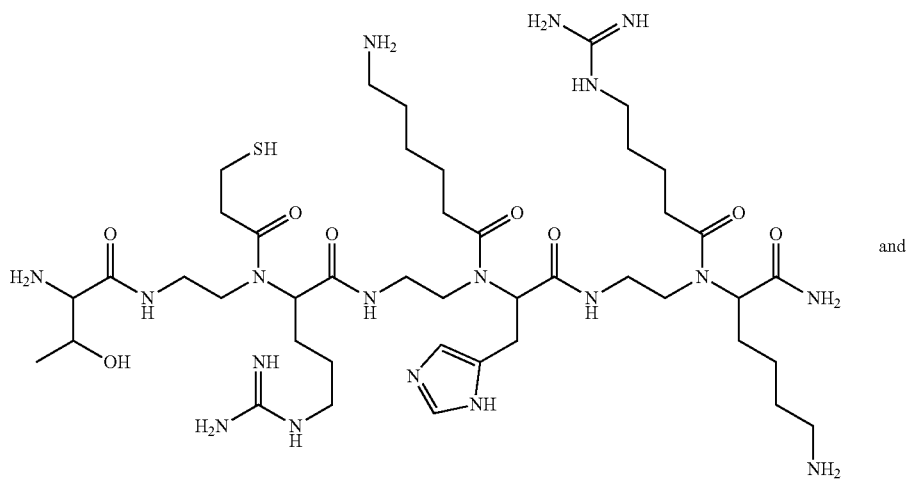

and

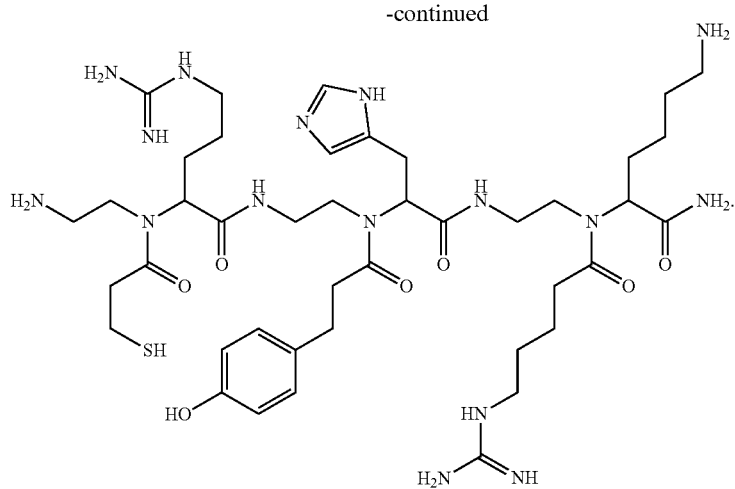
In a particular embodiment, a compound according to the invention is selected from formula:
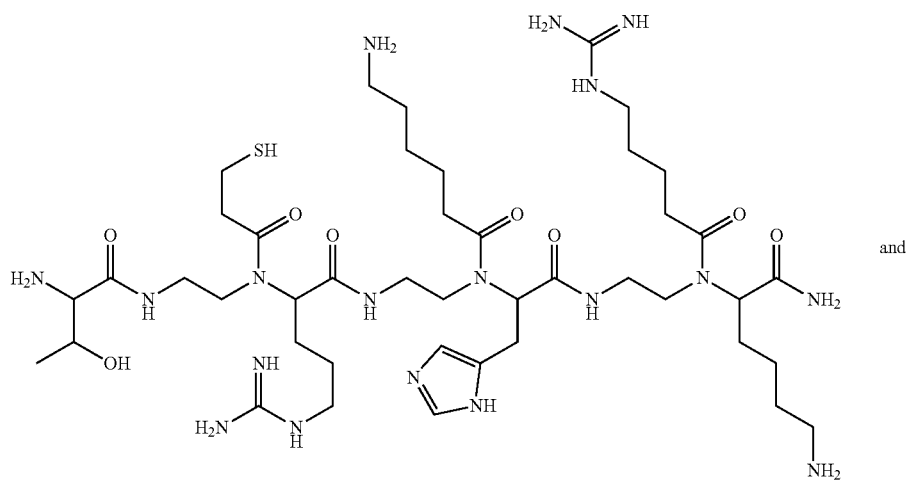
and
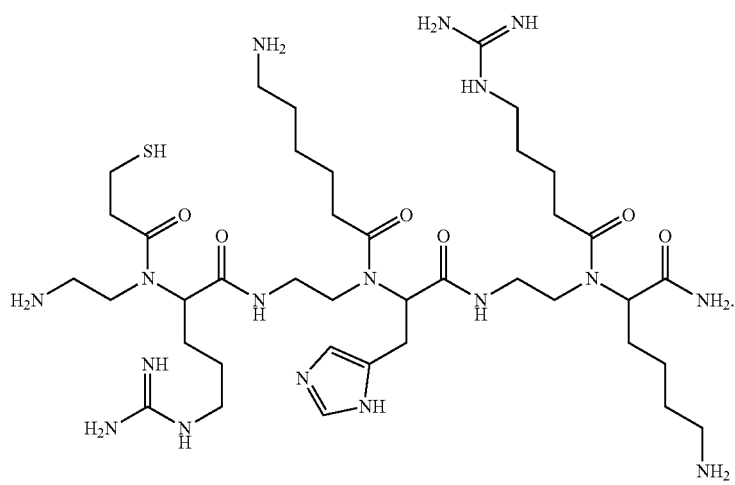

In another embodiment, a compound according to the invention is grafted with one or several element(s) selected from the group consisting of:
- a reactive moiety;
- a targeting agent, for example PEG or biotin;
- a dye, such as chromophore;
- a fluorophore, in particular rhodamine, fluorescein, BODIPY, indocyanine or 3,6-bis(1-methyl-4-vinylpyridinium);
- a chemical tag, in particular a ferrocenyl; and
- an immunomodulating agent, for example pomalidomide, in particular pomalidomide using a PEG linker.

According to another of its objects, the present invention relates to a pharmaceutical composition comprising, in a pharmaceutically acceptable medium, at least one compound according to the invention.

Another object of the present invention relates to a compound according to the invention, or a composition according to the invention, for its use as a medicament.

A further object of the present invention relates to a compound according to the invention or a composition according to the invention, for its use in the reduction of CD95-mediated cell motility in a subject in need thereof.

A further object of the present invention relates to a compound according to the invention or a composition according to the invention, for its use in the reduction of CD95-mediated cancer cell motility in a subject in need thereof.

In a particular embodiment, the compound or composition of the invention is for its use in the treatment of cancer in a subject in need thereof.

In a embodiment of the invention, the cancer is selected from neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; bronchiole-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In a particular embodiment, the subject suffers from a cancer selected from the group consisting of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers.

A further object of the present invention relates to a compound according to the invention or a composition according to the invention, for its use in the reduction of CD95-mediated lymphocyte motility and/or B cell maturation.

A further object of the present invention relates to a compound according to the invention or a composition according to the invention, for its use in the treatment of an auto-immune inflammatory disease.

In a particular embodiment, the autoimmune inflammatory disease is selected from the group consisting of Addison's Disease, Allergy, Alopecia Areata, Alzheimer's disease, Antineutrophil cytoplasmic antibodies (ANCA)-associated vasculitis, Ankylosing Spondylitis, Antiphospholipid Syndrome (Hughes Syndrome), arthritis, Asthma, Atherosclerosis, Atherosclerotic plaque, autoimmune disease (e.g., lupus, rheumatoid arthritis, multiple sclerosis, Graves' disease, etc.), Autoimmune Hemolytic Anemia, Autoimmune Hepatitis, Autoimmune inner ear disease, Autoimmune Lymphoproliferative syndrome, Autoimmune Myocarditis, Autoimmune Oophoritis, Autoimmune Orchitis, Azoospermia, Behcet's Disease, Berger's Disease, Bullous Pemphigoid, Cardiomyopathy, Cardiovascular disease, Celiac Sprue/Coeliac disease, Chronic Fatigue Immune Dysfunction Syndrome (CFIDS), Chronic idiopathic polyneuritis, Chronic Inflammatory Demyelinating, Polyradicalneuropathy (CIPD), Chronic relapsing polyneuropathy (Guillain-Barré syndrome), Churg-Strauss Syndrome (CSS), Cicatricial Pemphigoid, Cold Agglutinin Disease (CAD), chronic obstructive pulmonary disease (COPD), CREST syndrome, Crohn's disease, Dermatitis, Herpetiformus, Dermatomyositis, diabetes, Discoid Lupus, Eczema, Epidermolysis bullosa acquisita, Essential Mixed Cryoglobulinemia, Evan's Syndrome, Exopthalmos, Fibromyalgia, Goodpasture's Syndrome, Hashimoto's Thyroiditis, Idiopathic Pulmonary Fibrosis, Idiopathic Thrombocytopenia Purpura (ITP), IgA Nephropathy, immunoproliferative disease or disorder (e.g., psoriasis), Inflammatory bowel disease (IBD), including Crohn's disease and ulcerative colitis, Insulin Dependent Diabetes Mellitus (IDDM), Interstitial lung disease, juvenile diabetes, Juvenile Arthritis, juvenile idiopathic arthritis (JIA), Kawasaki's Disease, Lambert-Eaton Myasthenic Syndrome, Lichen Planus, lupus, Lupus Nephritis, Lymphoscytic Lypophisitis, Ménière's Disease, Miller Fish Syndrome/acute disseminated encephalomyeloradiculopathy, Mixed Connective Tissue Disease, Multiple Sclerosis (MS), muscular rheumatism, Myalgic encephalomyelitis (ME), Myasthenia Gravis, Ocular Inflammation, Pemphigus Foliaceus, Pemphigus Vulgaris, Pernicious Anaemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune cholangiopathy, Psoriasis, Psoriatic arthritis, Raynaud's Phenomenon, Reiter's Syndrome/Reactive arthritis, Restenosis, Rheumatic Fever, rheumatic disease, Rheumatoid Arthritis, Sarcoidosis, Schmidt's syndrome, Scleroderma, Sjörgen's Syndrome, Stiff-Man Syndrome, Systemic Lupus Erythematosus (SLE), systemic scleroderma, Takayasu Arteritis, Temporal Arteritis/Giant Cell Arteritis, Thyroiditis, Type 1 diabetes, Type 2 diabetes, Ulcerative colitis, Uveitis, Vasculitis, Vitiligo, and Wegener's Granulomatosis.

In a further embodiment, the compound or composition according to the invention, is for its use in the treatment of systemic lupus erythematosus.

A further object of the present invention relates to a compound according to the invention or a composition according to the invention, for its use in the treatment of antibody-mediated diseases. According to a particular embodiment, the antibody-mediated diseases include, but is not limited to, graft rejection, graft vs. host disease, and inflammatory-autoimmune diseases.

Another object of the present invention relates to a compound according to the invention or a composition according to the invention, for its use in the treatment of B-cell tumors, such as multiple myeloma and chronic lymphocytic leukemia.

FIGURES' LEGENDS

FIG. 1A: represents the ability of human minCID and of compound 13 of the invention to disrupt the CD95/PLCγ1 interaction without affecting the CD95/FADD interaction. SH3-PLCγ1-F1 or DD-FADD-F1 (inset) was co-transfected into HEK cells along with whole CID-CD95-F2 or DD-CD95-F2 (inset). After 24 h, cells were exposed for 4 h to the indicated drugs at different concentrations and luminescence was assessed. Luminescence being a marker of PPI activity, if the luminescence value drops, then it means that PPI is disrupted by the tested molecule. Data represent the mean±SD of three independent experiments. The Proton-pump inhibitory (PPI) activity (%) (in ordinate) is measured while varying the concentration of the tested drug (minCID or compound 13) (in abscissa).

Figure 1B:
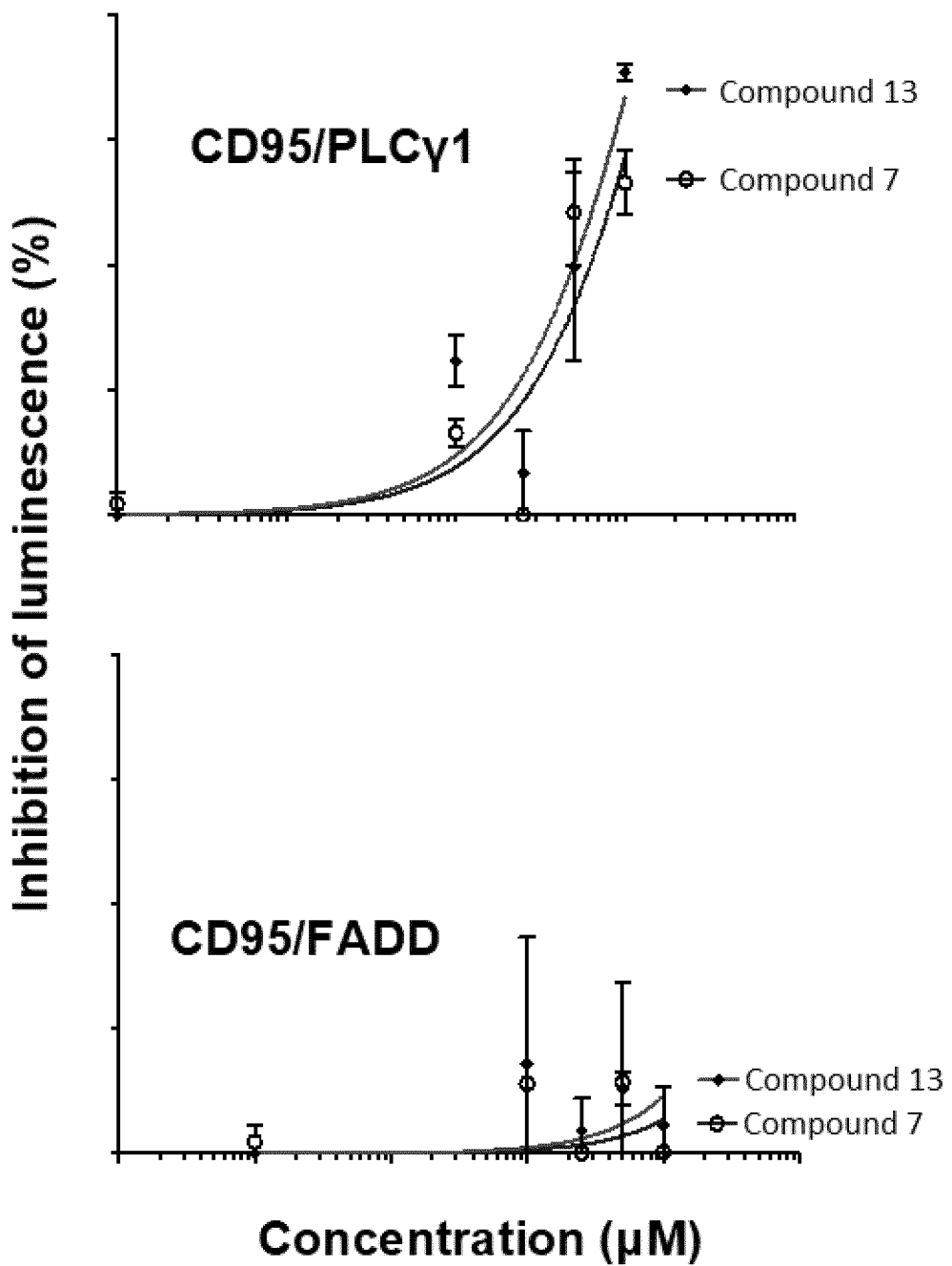

FIG. 1B: compares the ability of compound 7 and compound 13 of the invention to disrupt the CD95/PLCγ1 interaction without affecting the CD95/FADD interaction. SH3-PLCγ1-F1 or DD-FADD-F1 (inset) was co-transfected into HEK cells along with whole CID-CD95-F2 or DD-CD95-F2 (inset). After 24 h, cells were exposed for 4 h to the indicated drugs at different concentrations and luminescence was assessed.

Inhibition of luminescence (%) (in ordinate) is measured while varying the concentration of the tested drug (compound 7 or compound 13) (in abscissa). Data represent the mean±SD of three independent experiments.

Figure 1C:
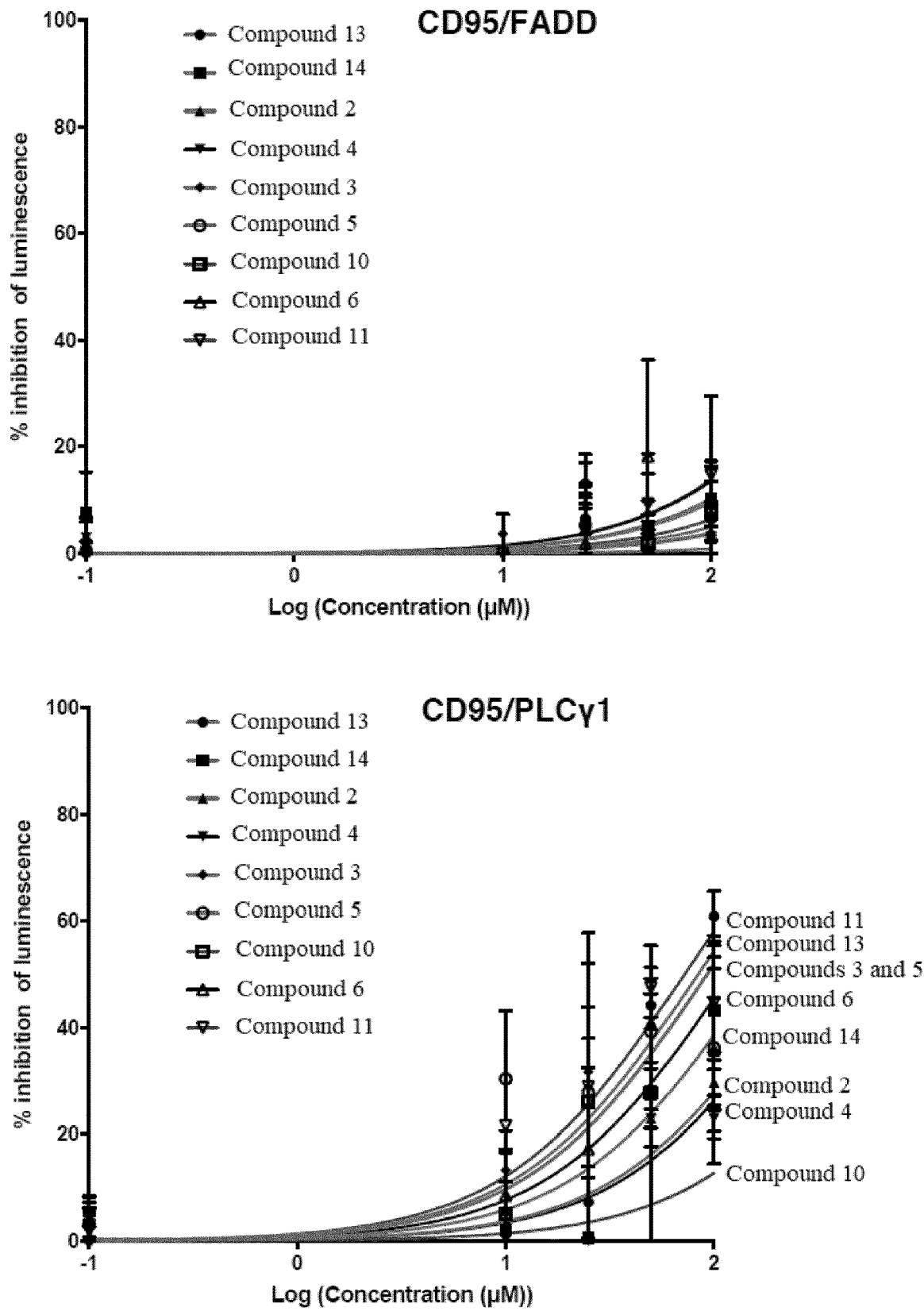

FIG. 1C: compares the ability of compounds 2, 3, 4, 5, 6, 10, 11, 13 and 14 of the invention to disrupt the CD95/PLCγ1 interaction without affecting the CD95/FADD interaction. SH3-PLCγ1-F1 or DD-FADD-F1 (inset) was co-transfected into HEK cells along with whole CID-CD95-F2 or DD-CD95-F2 (inset). After 24 h, cells were exposed for 4 h to the indicated drugs at different concentrations and luminescence was assessed.

Inhibition of luminescence (%) (in ordinate) is measured while varying the concentration of the tested drug (Concentration μM (in Log)) (in abscissa). Data represent the mean±SD of three independent experiments.

Figure 2:
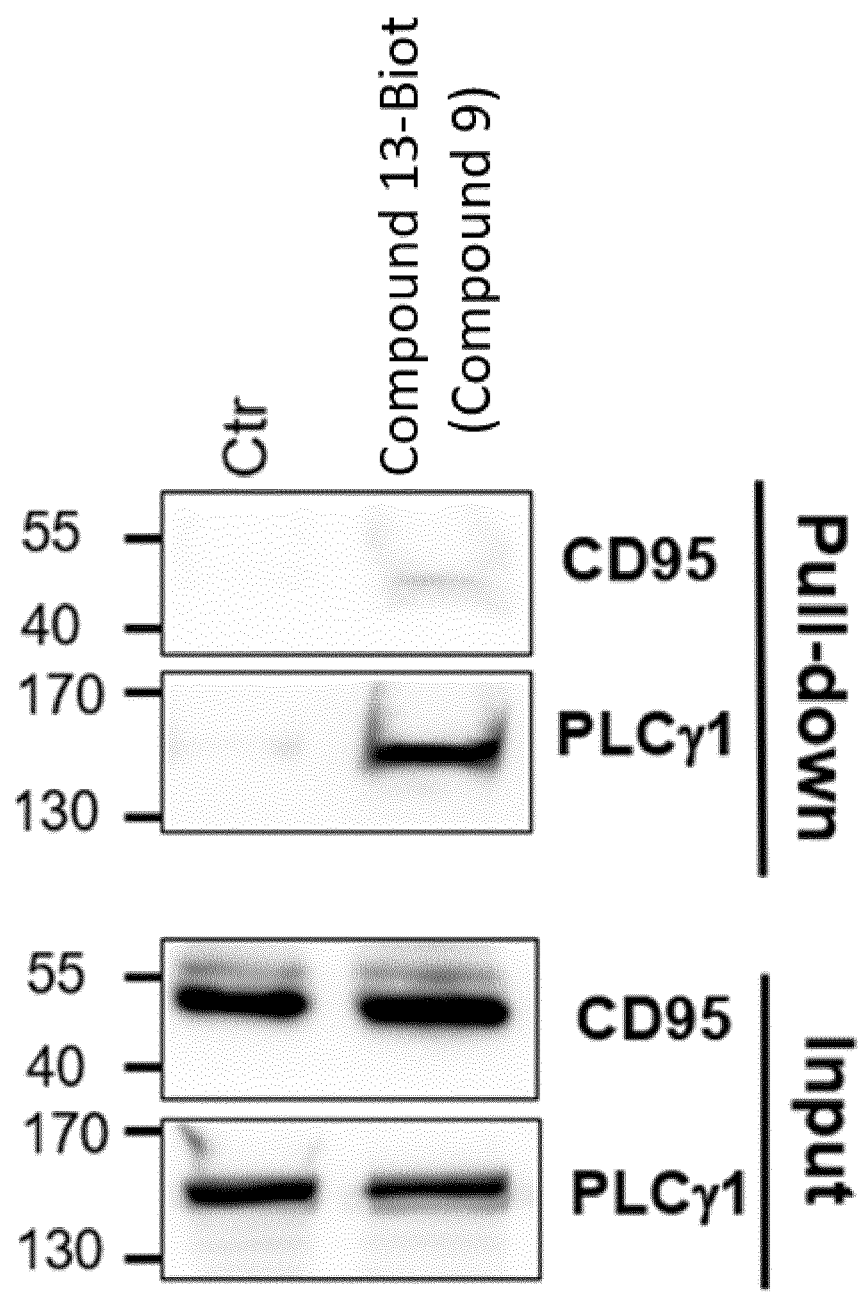

FIG. 2: displays a Western Blot showing the specific interaction of compound 13 with PLCγ1 but not with CD95. Compound 13 was conjugated to biotin and performed a pull-down assay. HEK cells were transfected with CD95 and PLCγ1. After 24 h, cells were lysed and treated for 30 min with/without 50 μM biotin-conjugated compound 13, followed by precipitation with streptavidin magnetic beads. The precipitated complex was then resolved in SDS-PAGE gels and immunoblotted with appropriate antibodies. Biotin-conjugated compound 13 interacted with endogenous PLCγ1.

Figure 3A:
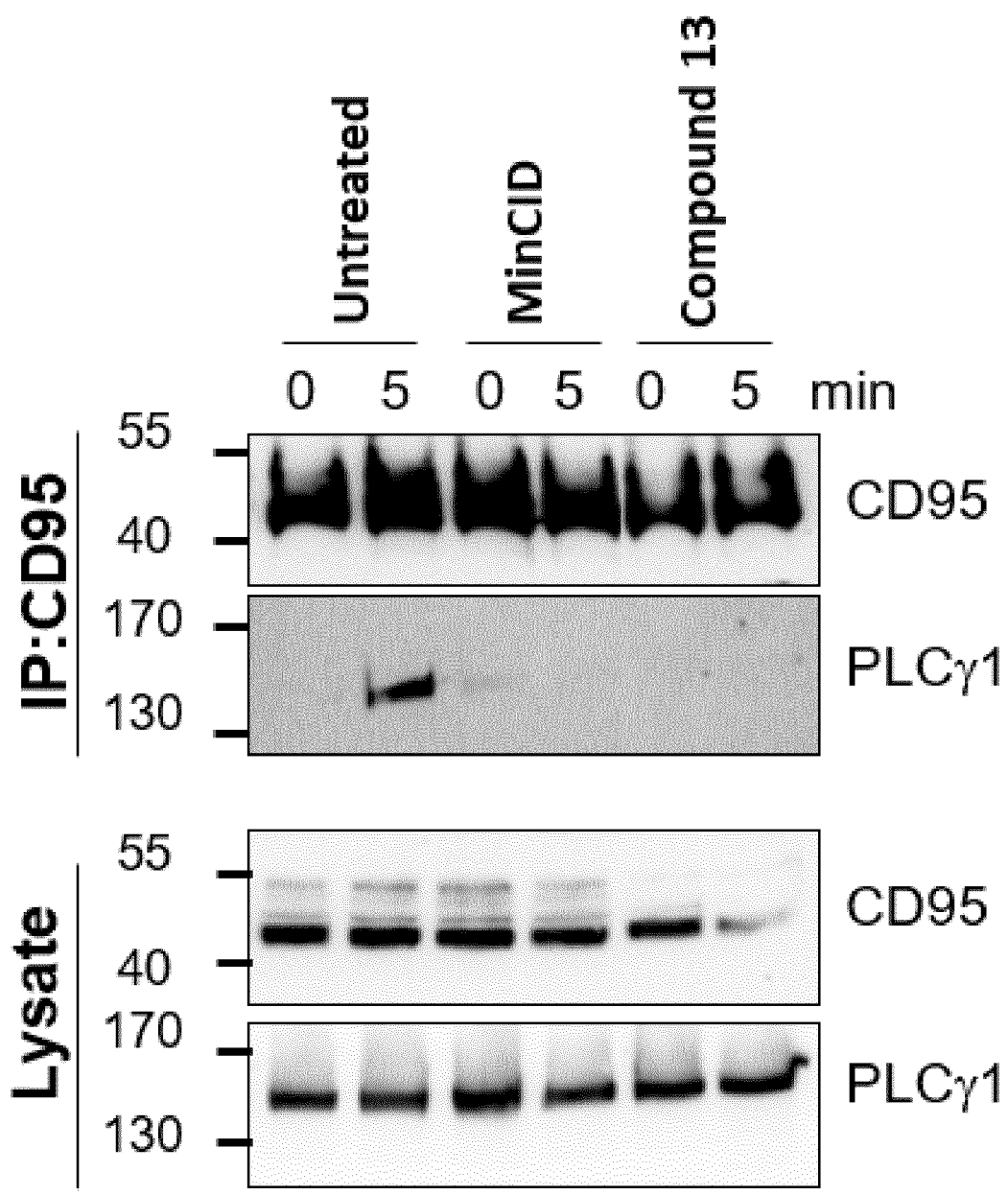

FIG. 3A: displays a Western Blot showing the specific inhibition of the interaction between PLCγ1 and CD95 by compound 13 of the invention in cells exposed to cl-CD95L. HEK cells were transfected with CD95 and PLCγ1. Cells were then pre-incubated for 1 h with compound 13 (at 50 μM), followed by stimulation for 5 min with cl-CD95L (100 ng/mL). CD95 was immunoprecipitated and the immune complex was resolved in SDS-PAGE gels prior to immunoblotting as indicated. Total lysate served as a control.

Figure 3B:
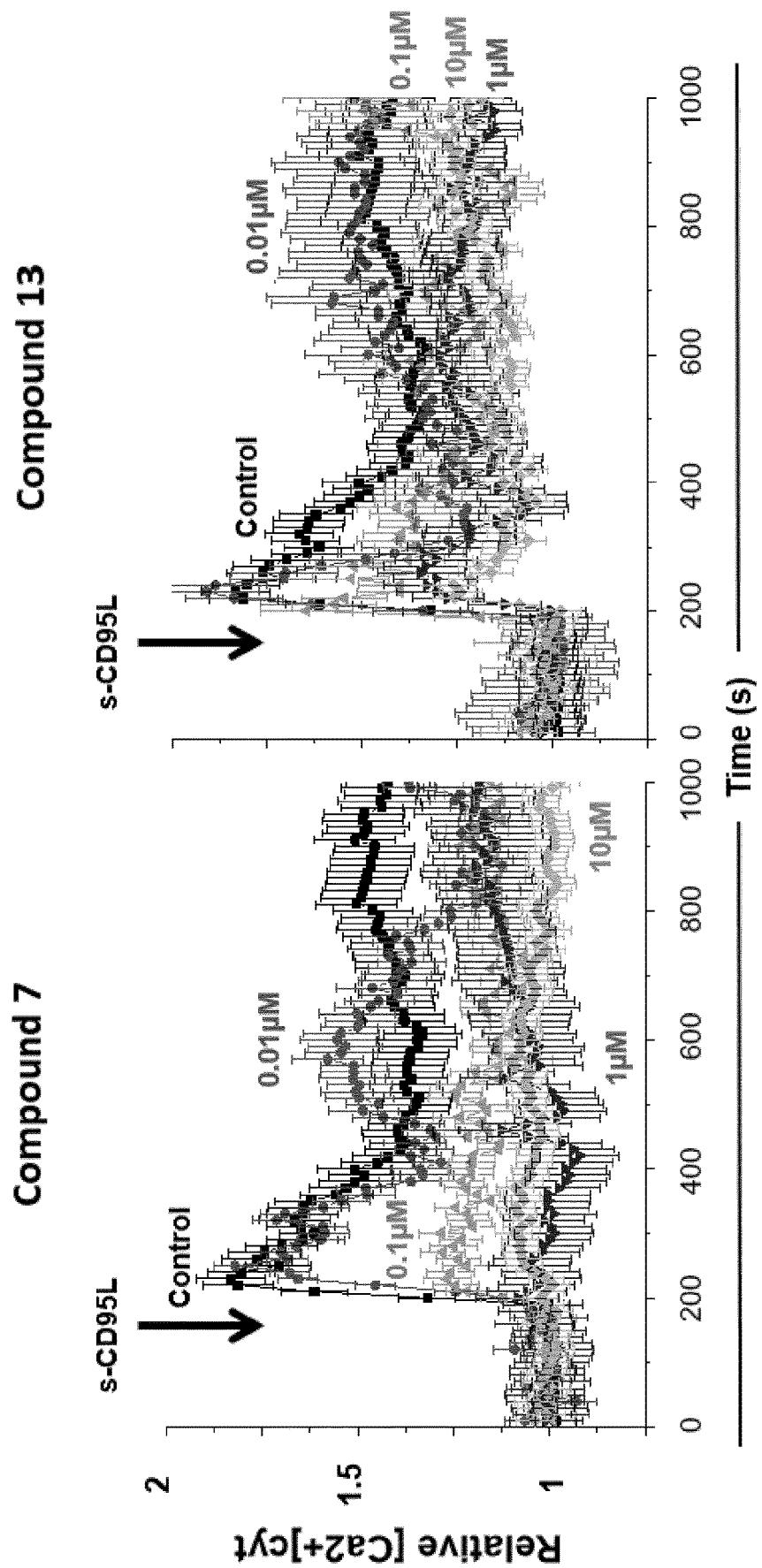

FIG. 3B: represents the ability of compounds 7 and 13 to abrogate binding of PLCγ1 to CD95 in cells exposed to cl-CD95L.

Mouse PBLs were loaded with Fluo2 LR-AM (2 μM) and pre-treated for 1 h with non-toxic concentrations of compound 7 or compound 13. T cells were then stimulated with cl-CD95L (100 ng/mL; arrow). Ratio values (R) were normalized to pre-stimulated values (R0) to yield R/R0 values. Data represent the mean±SD.

Relative $[Ca^{2+}]_{cyt}$ in ordinate and time in abscissa (seconds).

Figure 4:
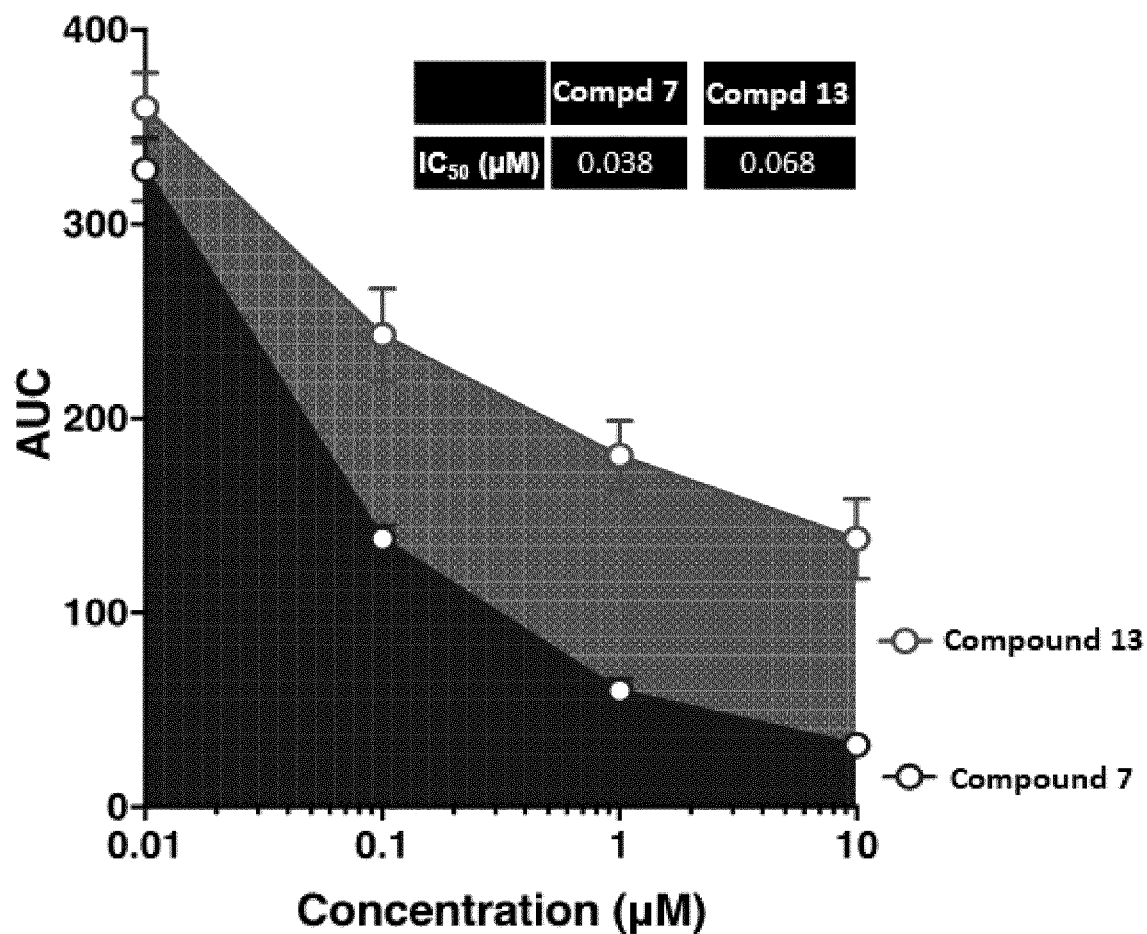

FIG. 4: is a graphic representing the area under the curve (AUC) measured from the CD95-mediated $Ca^{2+}$ responses shown in FIG. 3B, along with the corresponding $IC_{50}$ (inset), representing intracellular $Ca^{2+}$ concentration ($IC_{50}$=38 nM for compound 7 vs. 68 nM for compound 13).

AUC in ordinate and concentration of compound 7 or compound 13 in abscissa.

Figure 5:
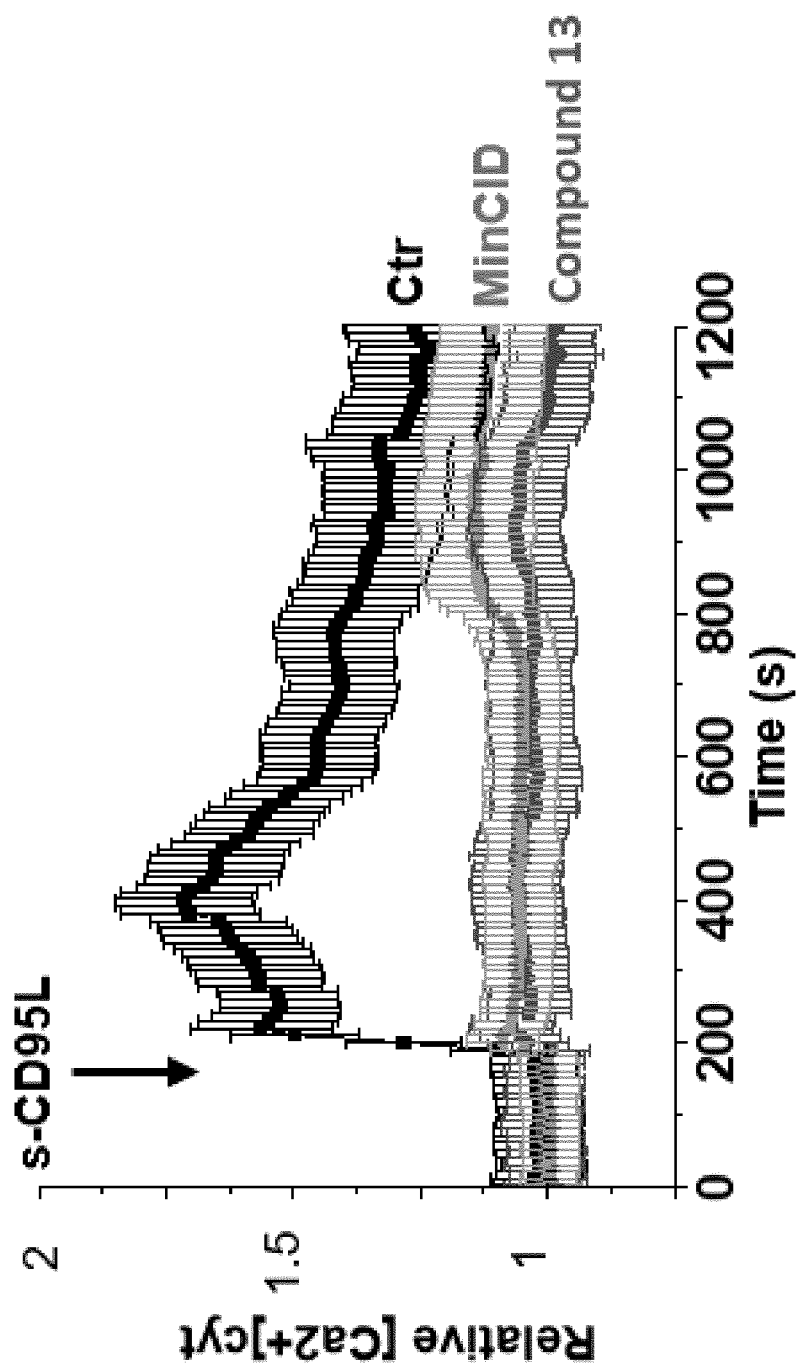

FIG. 5: illustrates the ability of compound 13 to inhibit the CD95-mediated $Ca^{2+}$ response in a manner similar to human minCID. Th17 cells were pre-incubated for 1 h with TAT-control, minCID, or compound 13 (each at 1 μM), and then stimulated with cl-CD95L (100 ng/mL). $[Ca^{2+}]_{CYT}$ was assessed in Fluo2 LR-AM (2 μM)-loaded cells. Data represent the mean±SD of three independent experiments.

Relative $[Ca^{2+}]_{CYT}$ in ordinate and time (in seconds) in abscissa.

Figure 6:
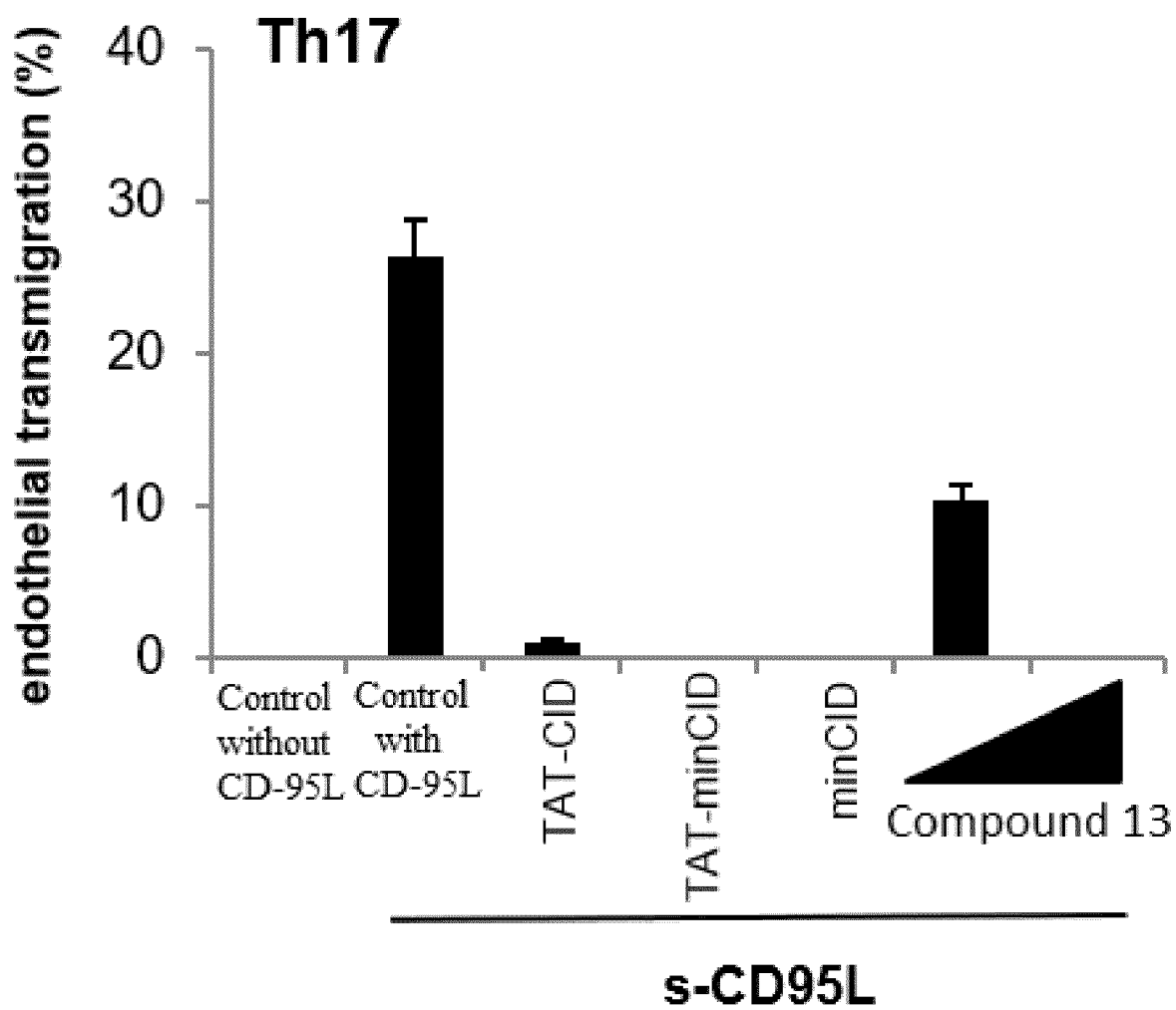

FIG. 6: illustrates the ability of compound 13 to prevent Th17 trafficking across endothelial cells. Th17 cells were pre-incubated for 1 h with TAT-control, TAT-CID, TAT-minCID, or minCID (each at 1 μM), or with compound 13 (at 1 or 10 μM), and then stimulated with cl-CD95L (100 ng/mL). Transendothelial migration of T cells was assessed in a Boyden chamber. Data represent the mean±SD of three independent experiments.

The endothelial transmigration (%) is represented in ordinate and the different tested controls (one negative control without CD95L and one positive control with CD95L), TAT-CID, TAT-minCID, minCID and compound 13 (at 1 or 10 μM) are represented in abscissa.

Figure 7:
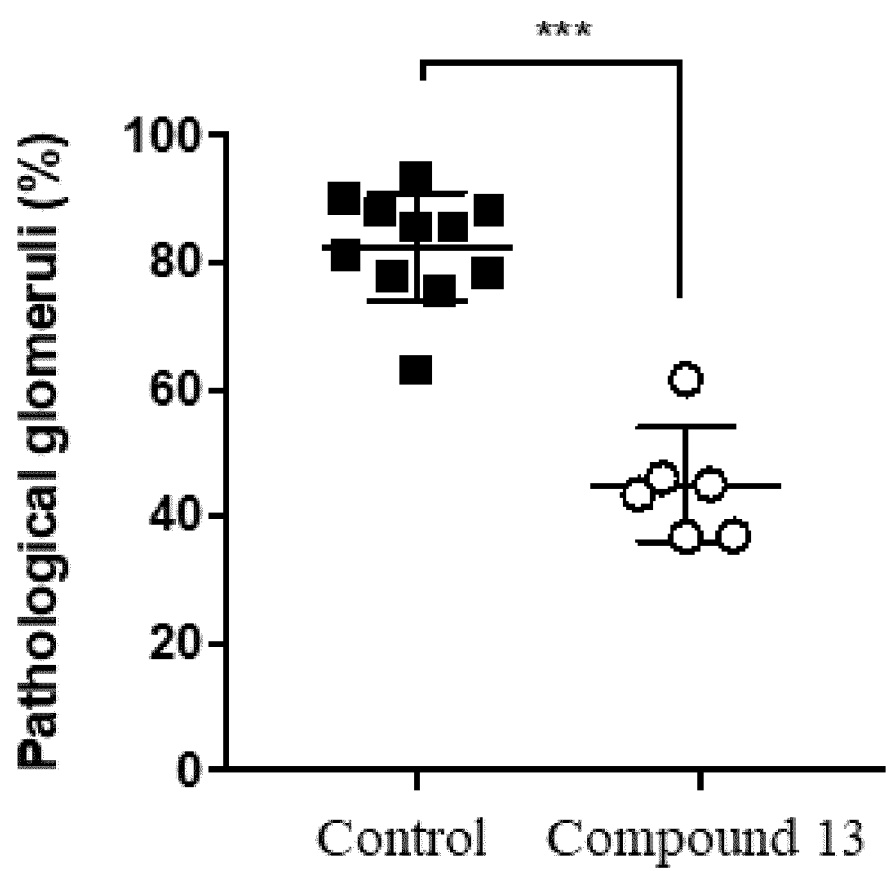

FIG. 7: illustrates the ability of compound 13 to alleviate clinical symptoms in lupus mice and thus to exhibit therapeutic activity in lupus-prone mice. After the first onset of the disease (i.e., increased proteinuria and detection of serum anti-dsDNA Ig), lupus mice received compound 13 or vehicle (control) three times per week for 5 weeks. $MRL^{Lpr/+}$ mice injected with compound 13 showed a significant reduction in the number of mesangial proliferation and adhesion of the Bowman's capsule as compared to control mice. Pathologic Glomerular damage scores were calculated for each kidney in control or compound 13-treated mice.

The percentage of pathological glomeruli is represented in ordinate and the abscissa represents percentage obtained for the control or the compound 13.

Figure 8:
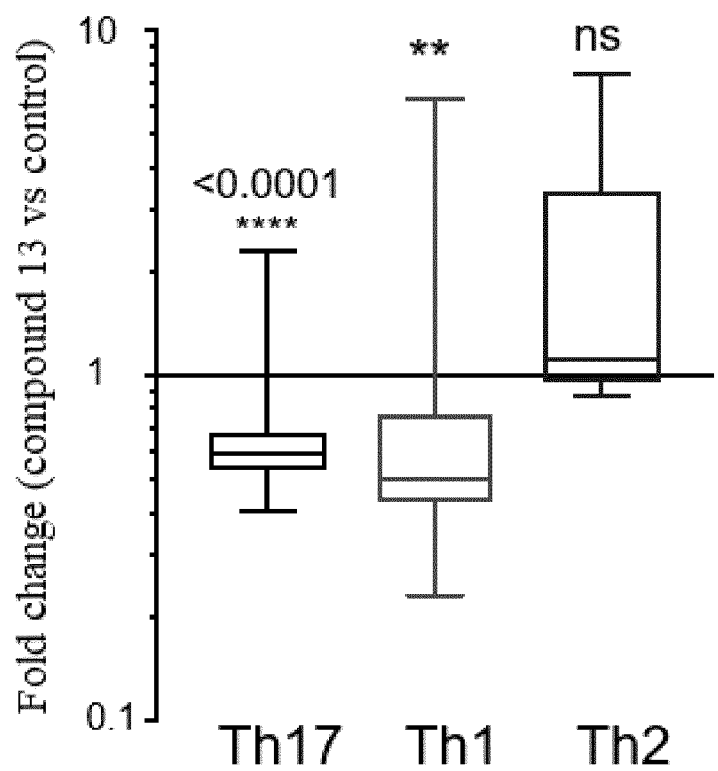

FIG. 8: compares the expression of mRNAs typical of Th17 (ror-γt, it-23r, IL17F), Th1 (TBX21, CXCR3, and INFG), or Th2 (GATA3, CCR4, and IL4) signatures in compound 13-treated kidneys with that in untreated mice. * p<0.05,  p<0.01, * p<0.001. The expression of Th17 markers (RORγt, IL-23R, and IL17F) in the kidneys of compound 13-treated mice was significantly lower than that in control mice (P=0.0013).

The fold change of compound 13 versus control is represented in ordinate while the abscissa indicates whether the results represented concerns Th17, Th1 or Th2.

Figure 9:
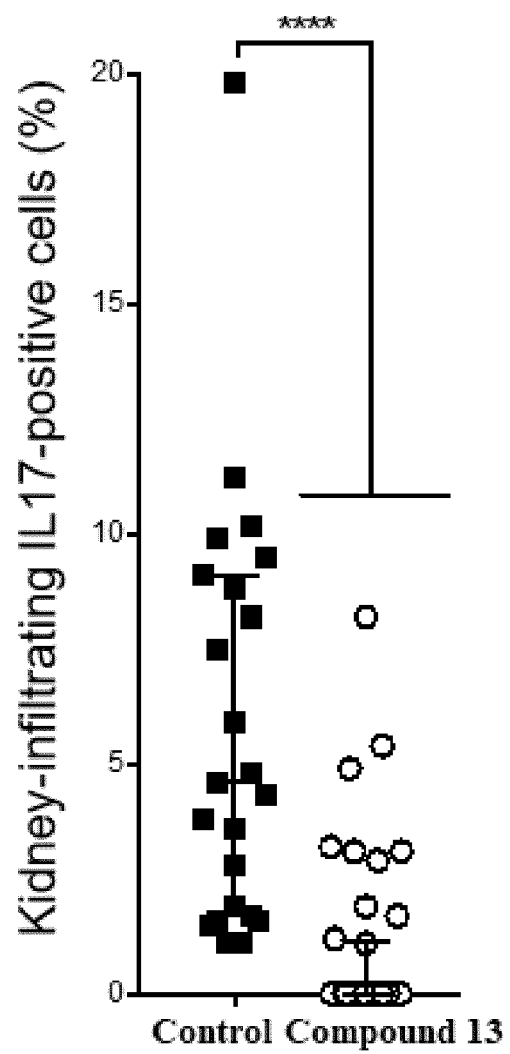

FIG. 9: illustrates the fact that accumulated IL17-expressing CD4+ cells in the inflamed kidneys of MRL1pr/+ mice were absent from those of compound 13-treated mice. IL17-positive cells was assessed in kidneys of indicated mice by densitometry. **** stands for p<0.0001 using were calculated using unpaired Student t-test.

The percentage of kidney-infiltrating IL17-positive cells is represented in ordinate while the abscissa indicates whether the results represented concerns control or compound-13 treated mice.

DETAILED DESCRIPTION OF THE INVENTION

As used herein:

"inhibition" or "inhibit" means totally or partially reducing the manifestation of a given phenomenon, i.e., the CD95-mediated cell motility in a subject; the CD95-mediated cancer cell motility in a subject; CD95-mediated lymphocyte motility and/or B cell maturation, in particular in a subject;

"pharmaceutically acceptable medium" refers to a carrier medium which does not interfere with the effectiveness of the biological activity of the active ingredient(s) and which is not excessively toxic to the host at the concentration at which it is administered. The use of such media for pharmaceutically active substances is well known in the art (see for example "Remington's Pharmaceutical Sciences", E. W. Martin, 18th Ed., 1990, Mack Publishing Co.: Easton, Pa.).

"subject" or "individual" is intended for an animal, including human beings, affected or likely to be affected with a disease or disorder that can be treated through reducing CD95-mediated cell motility. Said animal can in particular be intended for livestock, such as cattle, pigs and poultry; other non-human mammals such as pet, zoo or sports animals; or human beings, affected or likely to be affected with a virus infection according to the invention. Said individual is preferably a human being.

"treating" or "treatment" means totally or partially decrease, minimize or reduce, a particular disease or disorder, i.e. in particular in the present text, a cancer, an auto-immune inflammatory disease, in particular systemic lupus erythematosus, antibody-mediated diseases or B-cells tumors. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment.

the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may be treated by compounds and compositions of the present invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of histological type illustrated in the present text.

in the present invention, the term "Ar" represents an aryl or heteroaryl group, and is a mono or polycyclic aromatic or a mono or polycyclic heteroaromatic group which can be optionally substituted with one or more of the group consisting of:

a halo group; an azido group; a cyano group; a hydroxy group and a nitro group;

a linear or branched ($C_1$-$C_{20}$)alkyl group; a linear or branched ($C_1$-$C_6$)alkoxy group; a ($C_1$-$C_{20}$)alkylsulfanyl group; a linear or branched ($C_1$-$C_{20}$)alkenyl group; a linear or branched ($C_1$-$C_{20}$)alkynyl group; a linear or branched ($C_1$-$C_{20}$)alkenyloxy group; a linear or branched ($C_1$-$C_{20}$)alkenyloxy group; a linear or branched ($C_1$-$C_{20}$)alkenylsulfanyl group; a linear or branched ($C_1$-$C_{20}$)alkynylsulfanyl group; a ($C_1$-$C_{20}$) cycloalkoxy group and a ($C_1$-$C_{20}$)cycloalkylalkyl group;

whose alkyl, alkenyl, alkynyl or cycloalkyl group can be substituted with one or more of halo, hydroxy, polyhydroxy, alkoxy, hydroxyalkoxy, cyano, amino, aminoalkyl, alkylamino, dialkylamino, aminoalkylamino, aminoalkylaminocarbonyl, alkoxycarbonylamino, diarylmethylimino (where aryl is optionally substituted with one or more of hydroxy or halo), cycloalkenylimino (where cylalkenyl is optionally substituted with one or more of alkyl, OH), alkylsulfanyl, alkylsulfinyl, alkylsulfonyl, cycloalkyl, polycycloalkyl, cycloalkenyl, polycycloalkenyl, guanidino, alkylcarbonylguanidino, acylguanidino, cyanoguanidino, alkoxycarbonylguanidino, alkoxycarbonyl, alkoxycarbonylalkylamino, alkoxycarbonylalkylcycloalkyl, alkoxycarbonylheterocyclyl, aminocarbonyl, alkylaminocarbonyl, alkylcarbonyl, alkylcarbonylalkoxy, aryloxy, arylsulfanyl, arylsulfinyl, arylsulfonyl, heteroaryl, heterocyclyl (heterocyclyl being optionally substituted with one or more of oxo, amino, imino), heteroaryloxy, heterocyclyloxy, heteroarylamino, heterocyclylamino, hydrazinocarbonyl, hydroxyalkylcycloalkyl, N-alkyl(thioureido), phtalimido, ureido, oxocycloalkenylamino substituted with amino or carbamimidoylheterocyclyl;

an amino group; a linear or branched ($C_1$-$C_{20}$)alkylamino group; a linear or branched ($C_1$-$C_{20}$)alkylcarbonyl group; a linear or branched ($C_1$-$C_{20}$)alkoxycarbonyl group; a linear or branched ($C_1$-$C_{20}$)alkylsulfanyl group; a linear or branched ($C_1$-$C_{20}$)alkylsulfinyl group; a linear or branched ($C_1$-$C_{20}$)alkylsulfonyl group; and a linear or branched ($C_1$-$C_{20}$)alkylsulfonyloxy group, whose alkyl can be substituted with one or more halo group;

an aminocarbonyl group which can be N-substituted with one or two of linear or branched ($C_1$-$C_{20}$)alkyl, aryl or arylalkyl group;

an aryl group; an arylalkyl group; an aryloxy group; an arylalkoxy group; an arylalkylamino group; an arylalkylsulfanyl group; a heteroaryl group and a heteroaryloxy group, whose (hetero)aryl part can be substituted with one or more of amino, halo, linear or branched ($C_1$-$C_{20}$)alkyl, (poly)haloalkyl, hydroxyalkyl, alkoxy, (poly)haloalkoxy, alkoxycarbonylamino, alkylcarbonyl, alkylsulfanyl, alkylsulfinyl, alkylsulfonyl, nitro or cyanoalkyl, or fused with a non-aromatic heterocycle;

a heterocyclyl group; a heterocyclyloxy group and a heterocyclylalkoxy group, whose heterocycle can be substituted with one or more of halogenoalkyl, acylamino, acyloxy, amino, alkyl, alkylamino, dialkylamino, aminoalkyl, oxo, carbamimidoyl, halo, hydroxy, hydroxyalkyl, hydroxymethyl or alkoxcarbonyl;

and fused with a non-aromatic heterocycle (optionally substituted with one or more halogen) or a carbocycle group; as well as their enantiomers, diastereomers, mixtures thereof and pharmaceutically acceptable salts, tautomers, hydrates and solvates.

In the present invention, the term "Ar" according to the invention can in particular designate:

a cyclic, in particular mono-cyclic, aromatic group comprising between 6 and 10 carbon atoms. By way of examples of aryl groups, mention may be made of phenyl or naphthyl groups, in particular phenyl group;

an aromatic mono- or polycyclic group, preferably a mono- or bicyclic group, having from 5 to 10 ring members containing from 1 to 4 heteroatoms, in particular 1 or 2 heteroatoms, selected from O, S or N. By way of nonlimiting example, mention may be made of imidazolyl, thiazolyl, oxazolyl, furanyl, thiophenyl, oxadiazolyl, tetrazolyl, pyridinyl, pyrazinyl, pyrimidinyl, pyridazinyl, indolyl, indolinyl, benzofuranyl, benzothiophenyl, benzoxazolyl, benzimidazolyl, indazolyl, imidazolyl, benzothiazolyl, isobenzothiazolyl, benzotriazolyl, quinolinyl, isoquinolinyl or quinoxalinyl groups.

In the present invention, the term "Ar" preferably designates in a compound according to formula (A) of the invention a group selected from a phenyl, indolyl, indolinyl, imidazolyl or pyridinyl group.

In the present invention, the term "Halo" or "halogen" refers to fluorine, chlorine, bromine or iodine atom.

In the present invention, the term "alkyl" or "alkyl group" is intended to mean a linear or branched, saturated aliphatic group containing from 1 to 20 carbons. In particular, "alkyl" according to the invention can designate a ($C_1$-$C_{17}$)alkyl group, a ($C_2$-$C_{17}$)alkyl group, a ($C_1$-$C_{10}$)alkyl group, a ($C_1$-$C_6$)alkyl group, a ($C_1$—$O_5$) alkyl group, a ($C_1$-$C_4$)alkyl group, a ($C_1$-$C_3$)alkyl group or a ($C_1$-$C_2$)alkyl group, and can more particularly designate a ($C_1$-$C_{20}$)alkyl linear group, a ($C_1$-$C_{17}$)alkyl linear group, a ($C_2$-$C_{17}$)alkyl linear group, a ($C_1$-$C_{10}$) alkyl linear group, a ($C_1$-$C_6$)alkyl linear group, a ($C_1$-$C_5$)alkyl linear group, a ($C_1$-$C_4$)alkyl linear group, a ($C_1$-$C_3$)alkyl linear group or a ($C_1$-$C_2$)alkyl linear group.

By way of examples of an alkyl group according to the invention, mention may be made of methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, etc groups.

In the present invention, the term "a alkoxy group" is intended to mean: an —O-alkyl radical where the alkyl group is as defined above. It can in particular designate a ($C_1$-$C_6$)alkoxy group.

In the present invention, the term "amide" may be a primary amide, a secondary amide, a tertiary amide, a bis amide. Moreover, the amide may be saturated or may include one or more sites of unsaturation, such as at least one, and possibly several, double bonds that are substantially all trans, substantially all cis, or a mixture of cis and trans double bonds.

The present inventors have performed a huge amount of work with the view of identifying novel compounds endowed with the ability to reduce CD95-mediated cell motility in a subject and consequently to reduce CD95-mediated cancer motility and/or reduce CD95-mediated lymphocyte motility and/or B cell maturation.

Compounds of the Invention

The present invention relates to a compound of formula (A):

$$P_1-(P_2)_i-P_3-P_4-P_5-P_6-P_7 \quad (A)$$

These compounds are defined as follows:

i represents 0 or 1, with the proviso that when i represents 0, $P_1$ is directly bounded to $P_3$.

$P_1$ is selected from the group consisting of a hydrogen atom, a —$NH_2$ group and the following structures of formulae (I) and (II):

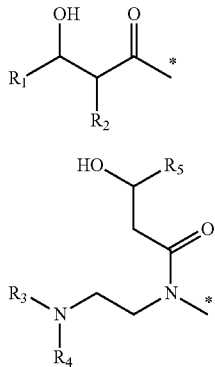

wherein:

$R_1$, $R_3$, $R_4$ and $R_5$ independently represent a hydrogen atom, a linear or branched ($C_1$-$C_{20}$)alkyl group, an aryl group or a linear or branched ($C_1$-$C_6$)alkoxy group;

$R_2$ represents a hydrogen atom or a —$NH_2$ group; and

* represents the bound with $P_2$ or, when i represents 0, with $P_3$.

In a particular embodiment, $R_1$ represents a hydrogen atom or a linear or branched ($C_1$-$C_{20}$)alkyl group, in particular a ($C_1$-$C_4$)alkyl group, and more preferably represents a —$CH_3$.

In a particular embodiment, $R_3$ and $R_4$ independently represent a hydrogen atom or a linear or branched ($C_1$-$C_{20}$) alkyl group, in particular a hydrogen atom or a ($C_1$-$C_4$)alkyl group. In an embodiment, at least one of $R_3$ and $R_4$ represents a hydrogen atom, and preferably $R_3$ and $R_4$ represent a hydrogen atom.

In an embodiment of the invention, $R_5$ represents a hydrogen atom or a linear or branched ($C_1$-$C_{20}$)alkyl group, in particular a ($C_1$-$C_4$)alkyl group, and more preferably represents a —$CH_3$.

In a particular embodiment, $P_1$ is selected from the group consisting of a hydrogen atom, a —$NH_2$ group and the following structures of formulae (I) and (II):

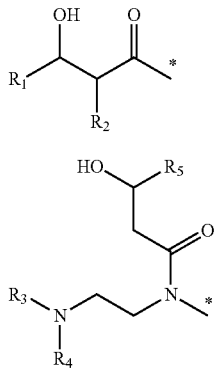

wherein:

$R_1$ and $R_5$ represent a —$CH_3$;

$R_2$ represents a hydrogen atom or a —$NH_2$ group;

$R_3$ and $R_4$ represent a hydrogen atom; and

* represents the bound with $P_2$ or, when i represents 0, with $P_3$.

In a particular embodiment, $P_1$ is selected from the group consisting of a hydrogen atom, a —$NH_2$ group and the three following structures:

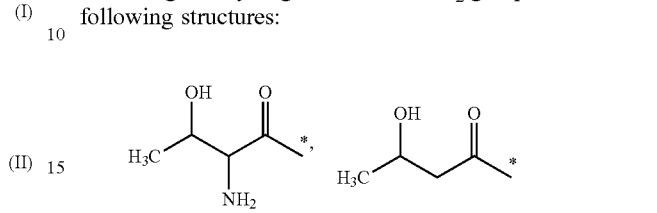

and wherein * represents the bound with $P_2$ or, when i represents 0, with $P_3$.

$P_2$ is selected from the group consisting of the following structures of formulae (III) and (IV):

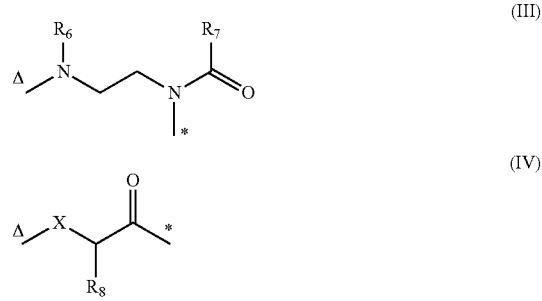

wherein:

$R_6$ represents an hydrogen atom or a linear or branched ($C_1$-$C_{20}$)alkyl group;

$R_7$ represents a linear or branched ($C_1$-$C_{20}$)alkyl group, a linear or branched ($C_1$-$C_6$)alkoxy group, or an aryl group, $R_7$ being optionally substituted with one or several, in particular 1, 2, 3 or 4, preferably 1, radical independently selected from the group consisting of —OH, —$NH_2$, —SH and an amide group;

$R_8$ represents a linear or branched ($C_1$-$C_{20}$)alkyl group, a linear or branched ($C_1$-$C_6$)alkoxy group, or an aryl group, $R_8$ being optionally substituted with one or several, in particular 1, 2, 3 or 4, preferably 1, radical independently selected from the group consisting of —OH, —SH, —$NH_2$ and an amide group;

X represents a single bond or —N($R_6$)—, $R_6$ being as defined previously;

Δ represents the bound with $P_1$ and * represents the bound with $P_3$;

In a particular embodiment, $R_6$ represents a hydrogen atom or a ($C_1$-$C_4$)alkyl group, and is preferably a hydrogen atom.

In a particular embodiment, $R_7$ represents a linear or branched ($C_1$-$C_{20}$)alkyl group, in particular a $C_1$-$C_{20}$ linear alkyl group, $R_7$ being optionally substituted with one or several radical(s), in particular 1, 2, 3 or 4, preferably 1 radical, independently selected from the group consisting of —OH, —SH and an amide group.

In a further embodiment, $R_7$ is selected from the group consisting of:
- a linear or branched, in particular linear, $C_{17}$ alkyl group; and
- a $C_2$ alkyl group, optionally substituted with one or several radical(s), in particular 1, 2, 3 or 4, preferably 1 radical, independently selected from the group consisting of —OH, —SH and an amide group.

In a particular embodiment, $R_7$ is selected from the group consisting of:
- a linear or branched, in particular linear, $C_{17}$ alkyl group;
- a $C_2$ alkyl group;
- a $C_2$ alkyl group substituted with a —OH group;
- a $C_2$ alkyl group substituted with a —SH group; and
- a $C_2$ alkyl group substituted with a —C(O)NH$_2$.

In a particular embodiment, $R_8$ represents a linear or branched $(C_1$-$C_{20})$alkyl group optionally substituted with one or several radical(s), in particular 1, 2, 3 or 4, preferably 1, independently selected from the group consisting of —OH, —SH, —NH$_2$ and an amide group.

In a particular embodiment, $R_8$ represents an $(C_1$-$C_4)$alkyl group optionally substituted with one or several radical(s), in particular 1, 2, 3 or 4, preferably 1 radical, independently selected from the group consisting of —OH, —SH, —NH$_2$ and an amide group and preferably represents a $(C_1$-$C_4)$alkyl group substituted with one or several radical(s), in particular 1, 2, 3 or 4, preferably 1 radical, independently selected from the group consisting of —OH, —SH, —NH$_2$ and an amide group, and preferably one radical —SH.

More particularly, $R_8$ represents a $C_1$ alkyl group substituted with —SH.

In an embodiment of the invention, in a structure of formula (III), $R_6$ represents a hydrogen atom and $R_7$ is selected from the group consisting of:
- a linear or branched, in particular linear, $C_{17}$ alkyl group;
- a $C_2$ alkyl group;
- a $C_2$ alkyl group substituted with a —OH group;
- a $C_2$ alkyl group substituted with a —SH group; and
- a $C_2$ alkyl group substituted with a —C(O)NH$_2$.

In an embodiment of the invention, in a structure of formula (IV), X represents —N($R_6$)—, $R_6$ representing a hydrogen atom, and $R_8$ represents a $C_1$ alkyl group substituted with —SH.

In another embodiment, in a structure of formula (IV), X represents single bound and $R_8$ represents a $C_1$ alkyl group substituted with —SH.

In a particular embodiment, a compound of formula (A) according to the invention is such that $P_1$ represents a hydrogen atom and i represents 0.

In another embodiment, a compound of formula (A) according to the invention is such that $P_1$ represents a —NH$_2$ group and i represents 0.

In another embodiment, a compound of formula (A) according to the invention is such that $P_1$ represents a hydrogen atom and $P_2$ is selected from:
(i) a structure of formula (III), wherein
$R_6$ represents a hydrogen atom; and
$R_7$ is selected from the group consisting of:
a linear or branched, in particular linear, $C_{17}$ alkyl group;
a $C_2$ alkyl group;
a $C_2$ alkyl group substituted with a —OH group;
a $C_2$ alkyl group substituted with a —SH group;
a $C_2$ alkyl group substituted with a —C(O)NH$_2$; and
Δ represents the bound with $P_1$ and * represents the bound with $P_3$;
and (ii) a structure of formula (IV), wherein:
X represents —N($R_6$)—, $R_6$ representing a hydrogen atom, and $R_8$ represents a $C_1$ alkyl group substituted with —SH; or
X represents single bound and $R_8$ represents a $C_1$ alkyl group substituted with —SH;
with Δ representing the bound with $P_1$ and * representing the bound with $P_3$.

In another embodiment, a compound of formula (A) according to the invention is such that
$P_1$ is selected from the structures of formulae (I) and (II):

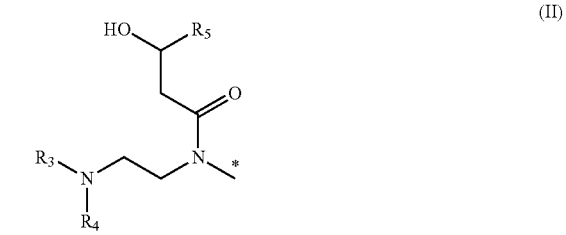

wherein:
$R_1$ and $R_5$ represent a —CH$_3$;
$R_2$ represents a hydrogen atom or a —NH$_2$ group;
$R_3$ and $R_4$ represent a hydrogen atom; and
* represents the bound with $P_2$;
and
$P_2$ is selected from:
(i) a structure of formula (III),

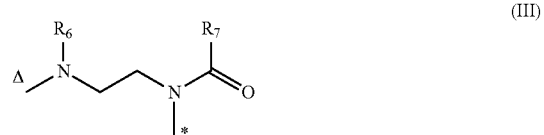

wherein
$R_6$ represents an hydrogen atom; and
$R_7$ represents a $C_2$ alkyl group substituted with a —SH group;
and
(ii) a structure of formula (IV),

wherein:
X represents —N($R_6$)—, $R_6$ representing a hydrogen atom, and $R_8$ represents a $C_1$ alkyl group substituted with —SH; or
X represents single bound and $R_8$ represents a $C_1$ alkyl group substituted with —SH.

In a particular embodiment, P₂ is selected from the group consisting of:

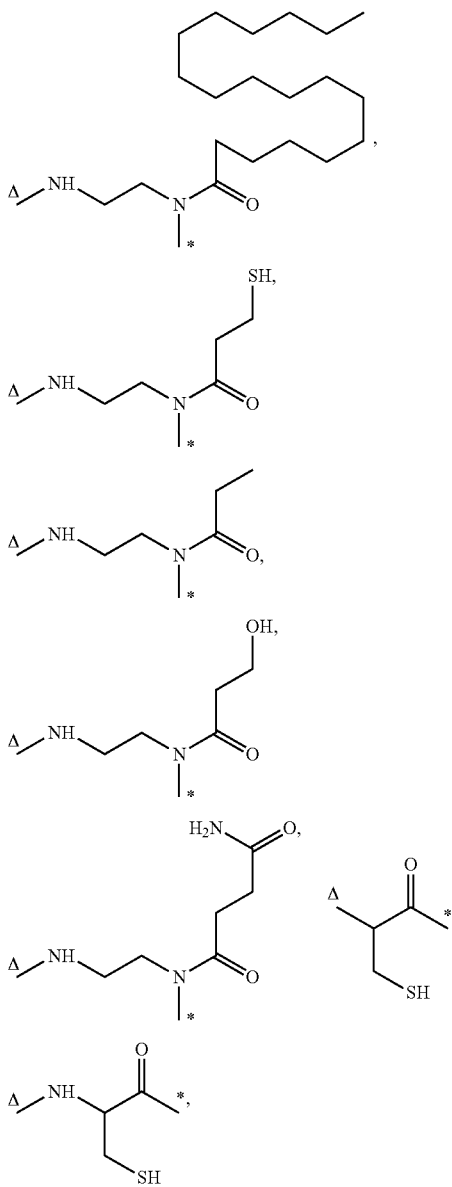

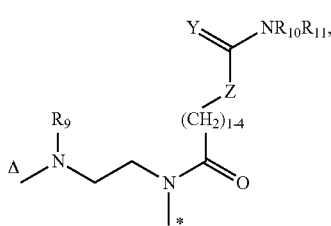

wherein Δ represents the bound with P₁ and * represents the bound with P₃.

P₃ is selected from the group consisting of the following structures of formulae (V), (VI), (VII) and (VIII):

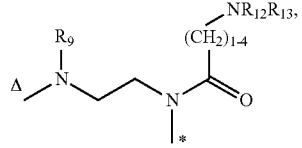
(V)

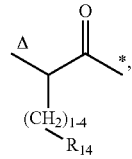
(VI)

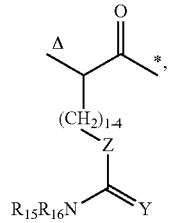
(VII)

(VIII)

wherein:
R₉ represents a hydrogen atom or a linear or branched $(C_1-C_{20})$alkyl group;
R₁₀, R₁₁, R₁₂, R₁₃, R₁₅ and R₁₆ independently represent a hydrogen atom or a linear or branched $(C_1-C_{20})$alkyl group;
R₁₄ represents an aryl group, a heteroaryl group or a —NR₁₇R₁₈ group, wherein R₁₇ and R₁₈ independently represent a hydrogen atom or a linear or branched $(C_1-C_{20})$alkyl group;
Y independently represents NH, O, S or CH₂;
Z independently represents —NH—, —N(CH₃)—, —S— or —CH₂—;
Δ represents the bound with P₂ when i represent 1 or with P₁ when i represents 0, and * represents the bound with P₄.

In a particular embodiment, P₃ is selected from the group consisting of formulae (V), (VII) or (VIII).

In a particular embodiment, R₉, R₁₀, R₁₁, R₁₅ and R₁₆ represent a hydrogen atom or a $(C_1-C_4)$alkyl group, and preferably represent a hydrogen atom.

In a particular embodiment, R₁₂ and R₁₃ represent a hydrogen atom or a $(C_1-C_4)$alkyl group, and preferably represent a hydrogen atom.

In particular embodiment, R₁₄ represents an aryl group or a heteroaryl group, in particular an indole or a pyridine group.

In an embodiment of P₃, Z represents —NH—.
In an embodiment of P₃, Y represents NH.
In an embodiment of P₃, (CH₂)₁₋₄ in formula (V) represents —(CH₂)₄—.
In an embodiment of P₃, (CH₂)₁₋₄ in formula (VII) represents —(CH₂)—.
In an embodiment of P₃, (CH₂)₁₋₄ in formula (VIII) represents —(CH₂)₃—.

In a particular embodiment, P₃ is selected from the group consisting of formulae (V), (VII) or (VIII) wherein:
R₉, R₁₀, R₁₁, R₁₅ and R₁₆ represent a hydrogen atom;
R₁₄ represents an aryl group or a heteroaryl group, in particular an indole or a pyridine group;

Z represents —NH—;

Y represents NH; and

Δ represents the bound with $P_2$ when i represent 1 or with $P_1$ when i represents 0, and * represents the bound with $P_4$.

In a preferred embodiment, when i represents 1 and $P_2$ is a structure of formula (III) as defined previously, $P_3$ is selected from the group consisting of the structures of formula (VII) and (VIII) as defined previously.

In another embodiment, when i represents 1 $P_2$ is a structure of formula (IV) as defined previously, $P_3$ is selected from the group consisting of the structures of formula (V) and (VI) as defined previously and is more particularly a structure of formula (V) as defined previously.

In a particular embodiment, $P_3$ is selected from the group consisting of:

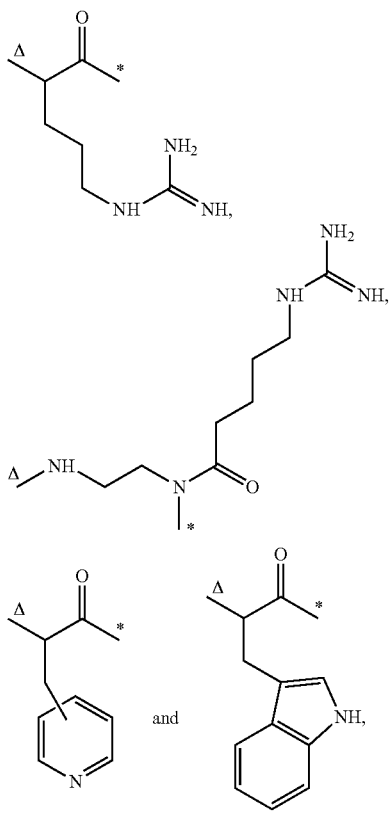

wherein Δ represents the bound with $P_2$ when i represent 1 or with $P_1$ when i represents 0, and * represents the bound with $P_4$.

More particularly, $P_3$ is selected from the group consisting of:

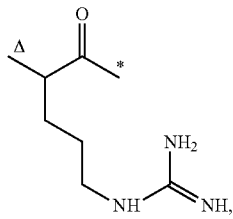

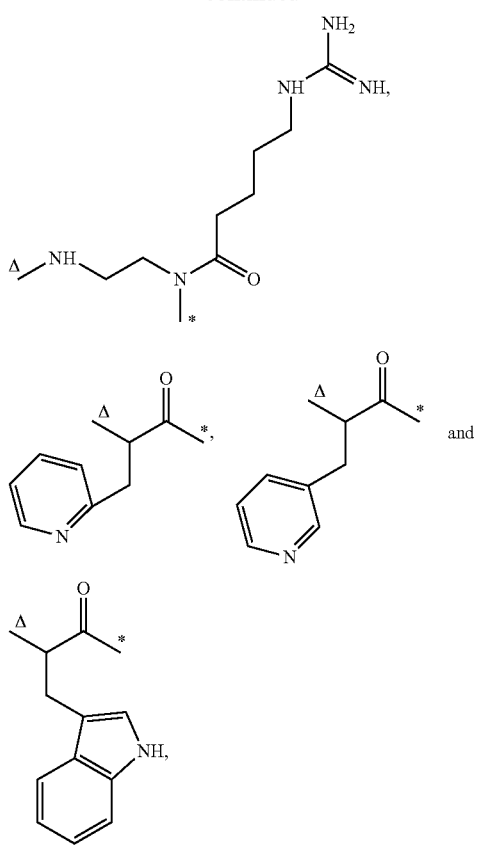

$P_4$ is selected from the group consisting of the following structures of formulae (IX), (X) and (XI):

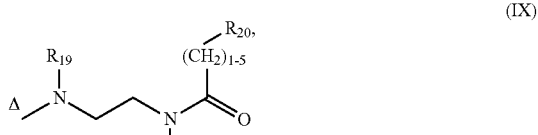

(IX)

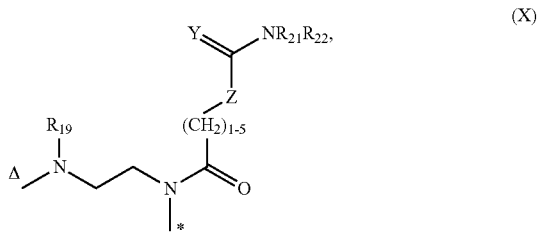

(X)

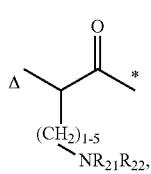

(XI)

wherein:

$R_{19}$ independently represents a hydrogen atom or a linear or branched ($C_1$-$C_{20}$)alkyl group;

$R_{20}$ represents an aryl group, a heteroaryl group or a —$NR_{21}R_{22}$ group, the aryl or heteroaryl group being optionally substituted with one or several, preferably one, —OH group;

$R_{21}$ and $R_{22}$ independently represent a hydrogen atom or a linear or branched $(C_1-C_{20})$alkyl group;

Y independently represents NH, O, S or $CH_2$;

Z independently represents —NH—, —N(CH$_3$)—, —S— or —CH$_2$—;

Δ represents the bound with $P_3$ and * represents the bound with $P_5$.

In a particular embodiment, $R_{19}$, $R_{21}$ and $R_{22}$ represent a hydrogen atom or a $(C_1-C_4)$alkyl group, and preferably $R_{19}$, $R_{21}$ and $R_{22}$ represent a hydrogen atom.

In a particular embodiment, $R_{20}$ represents:

a —$NH_2$ group;

an phenyl group substituted with one or several, in particular one, —OH group; or an indol group.

In an embodiment of $P_4$, Y represents NH or O.

In an embodiment of $P_4$, Z represents —NH— or —CH$_2$—.

In a particular embodiment of $P_4$, $(CH_2)_{1-5}$ in formula (IX) represents —$(CH_2)_2$— or —$(CH_2)_5$—.

In a particular embodiment of $P_4$, $(CH_2)_{1-5}$ in formula (X) represents —$(CH_2)_4$—.

In a particular embodiment of $P_4$, $(CH_2)_{1-5}$ in formula (XI) represents —$(CH_2)_4$—.

In a particular embodiment of $P_4$, Z represents —NH— and Y represents NH.

In a particular embodiment of $P_4$, Z represents —CH$_2$— and Y represents O.

In a particular embodiment of $P_4$, Z represents —CH$_2$—, Y represents O and $(CH_2)_{1-5}$ in formula (X) represents —$(CH_2)_4$—.

In a preferred embodiment of $P_4$:

$R_{19}$, $R_{21}$ and $R_{22}$ represent a hydrogen atom;

$R_{20}$ represents:

a —$NH_2$ group;

an phenyl group substituted with one or several, in particular one, —OH group;

an indoline group; or an indol group,

Z represents —NH— and Y represents NH or Z represents —CH$_2$— and Y represents O.

In a particular embodiment, $P_4$ is selected from the group consisting of:

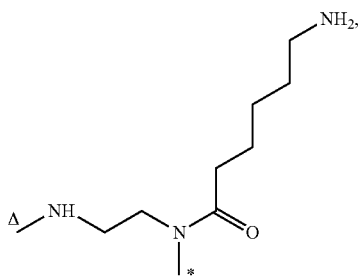

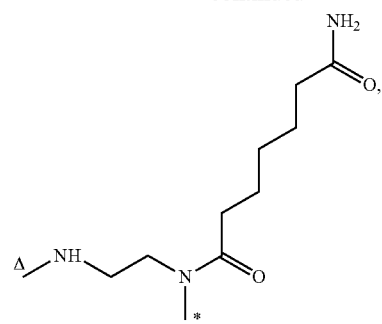

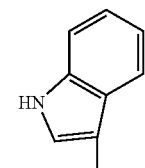

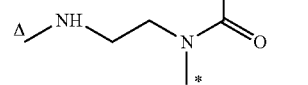

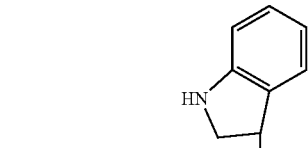

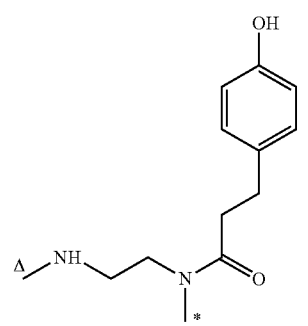 and 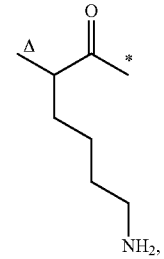

wherein Δ represents the bound with $P_3$ and * represents the bound with $P_5$.

$P_5$ is selected from the group consisting of the following structures of formulae (XII) and (XIII):

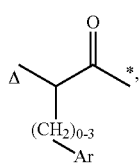

(XII)

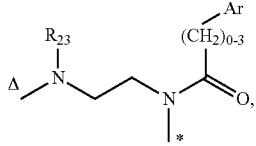
(XIII)

wherein:

R$_{23}$ represents a hydrogen atom or a linear or branched (C$_1$-C$_{20}$)alkyl group;

Ar represents an aryl or heteroaryl group, optionally substituted with one or several radical(s), in particular 1, 2, 3 or 4, preferably 1 radical, independently selected from the group consisting of —OH, —SH, —NH$_2$ and an amide group; and Δ represents the bound with P$_4$ and * represents the bound with P$_6$.

In a particular embodiment of P$_5$, (CH$_2$)$_{0-3}$ in formula (XII) represents —(CH$_2$)—.

In a particular embodiment of P$_5$, (CH$_2$)$_{0-3}$ in formula (XIII) represents —(CH$_2$)—.

In a particular embodiment of P$_5$, Ar in formulae (XII) and (XIII) represents an imidazole group.

In a preferred embodiment, R$_{23}$ represents a hydrogen atom.

In a particular embodiment, P$_5$ is selected from the group consisting of the structures of formulae (XII) and (XIII) wherein:

R$_{23}$ represents a hydrogen atom,

Ar represents an imidazole group, (CH$_2$)$_{0-3}$ in formulae (XII) and (XIII) represents —(CH$_2$)—; and Δ represents the bound with P$_4$ and * represents the bound with P$_6$.

In a particular embodiment, P$_5$ is selected from the group consisting of:

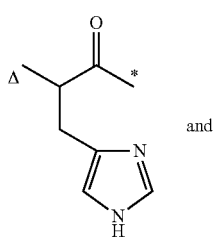

and

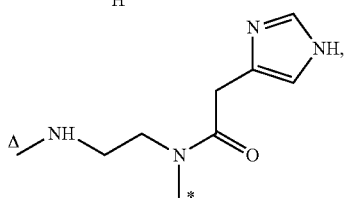

wherein Δ represents the bound with P$_4$ and * represents the bound with P$_6$.

P$_6$ is selected from the group consisting of the following structures of formulae (XIV), (XV), (XVI), (XVII) and (XVIII):

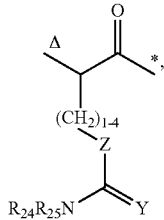
(XIV)

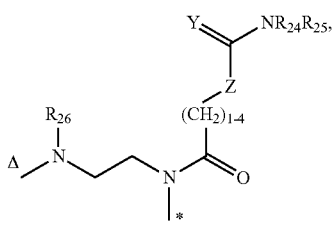
(XV)

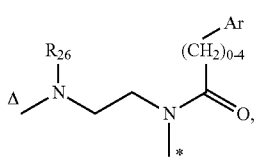
(XVI)

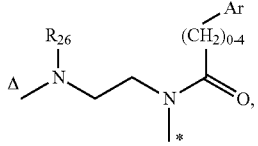
(XVII)

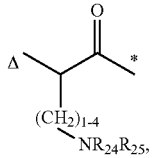
(XVIII)

wherein:

R$_{24}$, R$_{25}$ and R$_{26}$ independently represent a hydrogen atom or a linear or branched (C$_1$-C$_{20}$)alkyl group;

Ar represents an aryl or heteroaryl group, optionally substituted with one or several radical(s), in particular 1, 2, 3 or 4, preferably 1 radical, independently selected from the group consisting of —OH, —NH$_2$, —SH and an amide group;

Y independently represents NH, O, S or CH$_2$;

Z independently represents —NH—, —N(CH$_3$)—, —S— or —CH$_2$—; and

Δ represents the bound with P$_5$ and * represents the bound with P$_7$.

In a particular embodiment, P$_6$ is selected from the group consisting of formulae (XIV), (XV) or (XVI).

In a particular embodiment, R$_{24}$, R$_{25}$ and R$_{26}$ represent a hydrogen atom.

In a particular embodiment of P$_6$, Ar represents a phenyl or an indole group, optionally substituted with one or several radical(s) in particular 1, 2, 3 or 4, preferably 1 radical, independently selected from the group consisting of —OH, —NH$_2$, —SH and an amide group.

According to this embodiment, of P$_6$, Ar can represent a phenyl or an indole group, optionally substituted with one or several radical(s) in particular 1, 2, 3 or 4, preferably 1 radical, independently selected from the group consisting of —OH and —NH$_2$, in particular represent:
- a phenyl group substituted by one —OH or —NH$_2$ group; or
- an indole group.

In a particular embodiment of P$_6$, Y independently represents NH or O.

In a particular embodiment of P$_6$, Z independently represents —NH—, or —CH$_2$—.

In a particular embodiment of P$_6$, (CH$_2$)$_{1-4}$ in formula (XIV) represents —(CH$_2$)$_3$—.

In a particular embodiment of P$_6$, (CH$_2$)$_{1-4}$ in formula (XV) represents —(CH$_2$)$_4$—.

In a particular embodiment of P$_6$, (CH$_2$)$_{0-4}$ in formula (XVI) represents —(CH$_2$)$_2$—.

In a preferred embodiment, P$_6$ is selected from the group consisting of the structures of formulae (XIV), (XV) and (XVI), wherein:
- R$_{24}$, R$_{25}$ and R$_{26}$ represent a hydrogen atom;
- Ar represents:
  - a phenyl group substituted by one —OH or —NH$_2$ group; or
  - an indole group;
- Y independently represents NH or O;
- Z independently represents —NH—, or —CH—;
- (CH$_2$)$_{1-4}$ in formula (XIV) represents —(CH$_2$)$_3$—;
- (CH$_2$)$_{1-4}$ in formula (XV) represents —(CH$_2$)$_4$—;
- (CH$_2$)$_{0-4}$ in formula (XVI) represents —(CH$_2$)$_2$—; and
- Δ represents the bound with P$_5$ and * represents the bound with P$_7$.

In a particular embodiment, P$_6$ is selected from the group consisting of:

wherein Δ represents the bound with P$_5$ and * represents the bound with P$_7$.

P$_7$ is selected from the group consisting of the following structures of formulae (XIX) and (XX):

(XIX)

(XX)

wherein:
R$_{27}$, R$_{28}$ and R$_{29}$ independently represent a hydrogen atom or a linear or branched (C$_1$-C$_{20}$)alkyl group; and
Δ represents the bound with P$_6$.

In a particular embodiment, R$_{27}$ and R$_{28}$ represent a hydrogen atom.

In a particular embodiment, R$_{29}$ represents a hydrogen atom.

In a particular embodiment of P$_7$, (CH$_2$)$_{1-5}$ in formula (XIX) represents —(CH$_2$)$_4$—.

In a particular embodiment of $P_7$, $(CH_2)_{1-5}$ in formula (XX) represents —$(CH_2)_5$—.

In a preferred embodiment, $P_7$ is selected from the group consisting of the structures of formulae (XIX) and (XX), wherein:

$R_{27}$, $R_{28}$ and $R_{29}$ represent a hydrogen atom;
$(CH_2)_{1-5}$ in formula (XIX) represents —$(CH_2)_4$—;
$(CH_2)_{1-5}$ in formula (XX) represents —$(CH_2)_5$—; and
Δ represents the bound with $P_6$.

In a particular embodiment, $P_7$ is selected from the group consisting of:

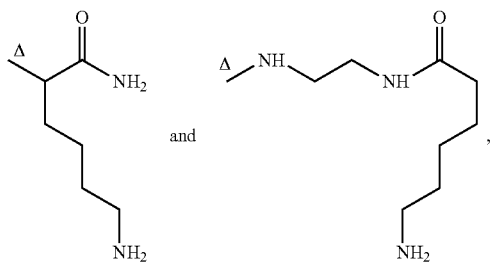

wherein Δ represents the bound with $P_6$.

In a particular embodiment, a compound of formula (A) according to the invention is such that when $P_1$ is a hydrogen atom or a structure of formula (I) as defined above, then $P_2$ is of formula (III) as defined above.

In a particular embodiment, a compound of formula (A) according to the invention is such that when $P_2$ is of formula (III) as defined above, then $P_3$ is of formula (VII) or (VIII) as defined above.

In a particular embodiment, a compound of formula (A) according to the invention is such that when $P_3$ is of formula (VII) or (VIII) as defined above, then $P_4$ is of formula (IX) or (X) as defined above.

In a particular embodiment, a compound of formula (A) according to the invention is such that when $P_4$ is of formula (IX) or (X) as defined above, then $P_5$ is of formula (XII) as defined above.

In a particular embodiment, a compound of formula (A) according to the invention is such that when $P_5$ is of formula (XII) as defined above, then $P_6$ is of formula (XV), (XVI) or (XVIII) as defined above.

In a particular embodiment, a compound of formula (A) according to the invention is such that when $P_6$ is of formula (XV), (XVI) or (XVIII) as defined above, then $P_7$ is of formula (XIX) as defined above.

In a particular embodiment, a compound of formula (A) according to the invention is such that:
$P_1$ is a hydrogen atom or a structure of formula (I) as defined above;
$P_2$ is of formula (III) as defined above;
$P_3$ is of formula (VII) or (VIII) as defined above;
$P_4$ is of formula (IX) or (X) as defined above;
$P_5$ is of formula (XII) as defined above;
$P_6$ is of formula (XV), (XVI) or (XVIII) as defined above; and
$P_7$ is of formula (XIX) as defined above.

In a particular embodiment, a compound of formula (A) according to the invention is such that when $P_1$ is a hydrogen atom, a —$NH_2$ group or a structure of formula (II) as defined above, then $P_2$ is of formula (IV) as defined above.

In a particular embodiment, a compound of formula (A) according to the invention is such that when $P_2$ is of formula (IV) as defined above, then $P_3$ is of formula (V) or (VI) as defined above.

In a particular embodiment, a compound of formula (A) according to the invention is such that when $P_3$ is of formula (V) or (VI) as defined above, then $P_4$ is of formula (XI) as defined above.

In a particular embodiment, a compound of formula (A) according to the invention is such that when $P_4$ is of formula (XI) as defined above, then $P_5$ is of formula (XIII) as defined above.

In a particular embodiment, a compound of formula (A) according to the invention is such that when $P_5$ is of formula (XIII) as defined above, then $P_6$ is of formula (XIV) or (XVII) as defined above.

In a particular embodiment, a compound of formula (A) according to the invention is such that when $P_6$ is of formula (XIV) or (XVII) as defined above, then $P_7$ is of formula (XX) as defined above.

In a particular embodiment, a compound of formula (A) according to the invention is such that:
$P_1$ is a hydrogen atom, a —$NH_2$ group or a structure of formula (II) as defined above;
$P_2$ is of formula (IV) as defined above;
$P_3$ is of formula (V) or (VI) as defined above;
$P_4$ is of formula (XI) as defined above;
$P_5$ is of formula (XIII) as defined above;
$P_6$ is of formula (XIV) or (XVII) as defined above; and
$P_7$ is of formula (XX).

In a particular embodiment, when i represents O and $P_3$ is selected from the group consisting of structures (V) and (VI), $P_1$ is preferably a hydrogen atom.

In a particular embodiment, when i represents O and $P_3$ is selected from the group consisting of structures (VII) and (VIII), $P_1$ is preferably a —$NH_2$ group.

Particularly preferred compounds of formula (A) according to the invention are selected from the group consisting of:

| Compound | Structure | LC-MS Rt (min) m/z (uma) |
|---|---|---|
| Compound 1 | 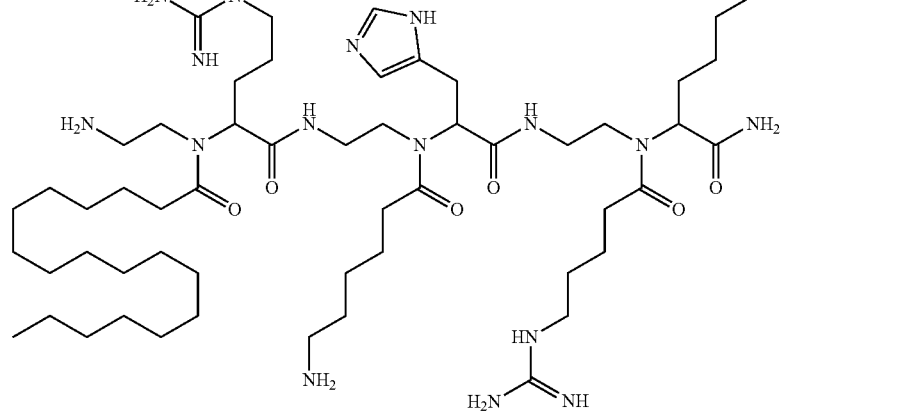 | 27.88  545.4 |
| Compound 2 | 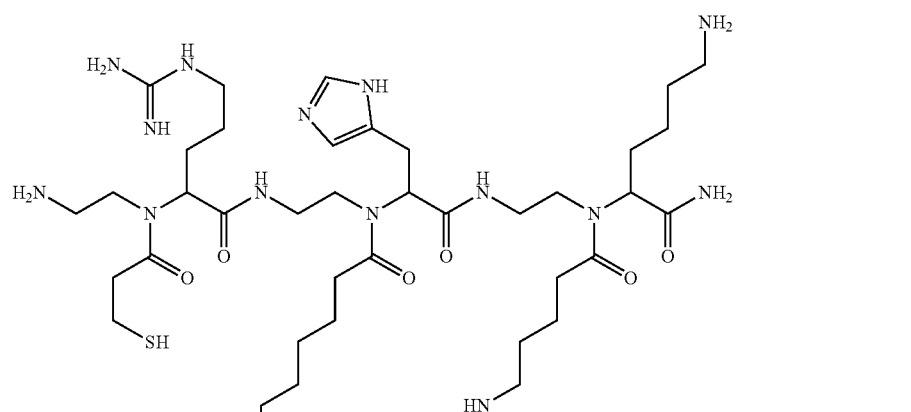 | 12.76  470.3 |
| Compound 3 | 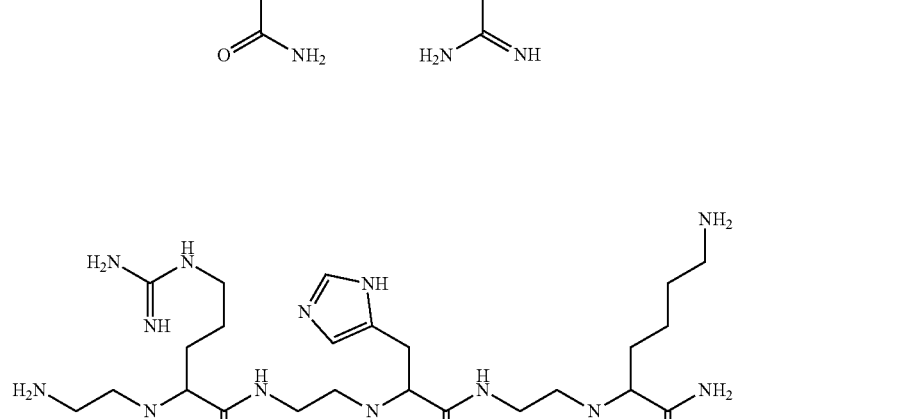 | 16.9  485.3 |

| Compound | Structure | LC-MS Rt (min) m/z (uma) |
|---|---|---|
| Compound 4 | 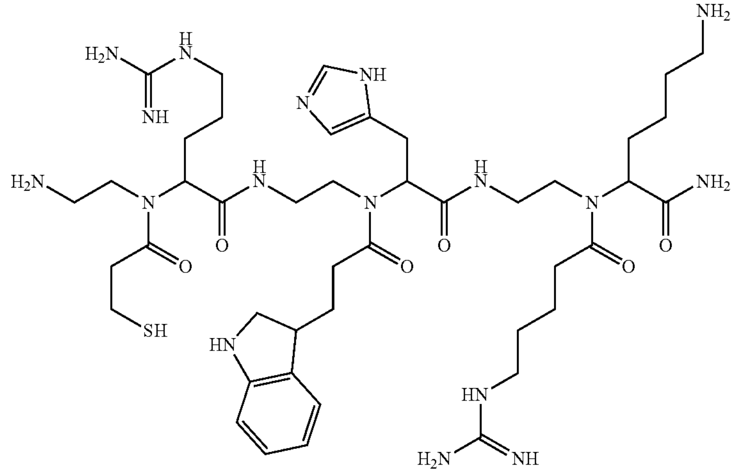 [SMILES: N=C(N)NCCCCC(=O)N(CCNC(=O)C(Cc1cnc[nH]1)N(CCNC(=O)C(CCCNC(=N)N)N(CCN)C(=O)CCS)C(=O)CCC1CNc2ccccc21)C(CCCCN)C(N)=O] | 14.06<br>486.3 |
| Compound 5 | 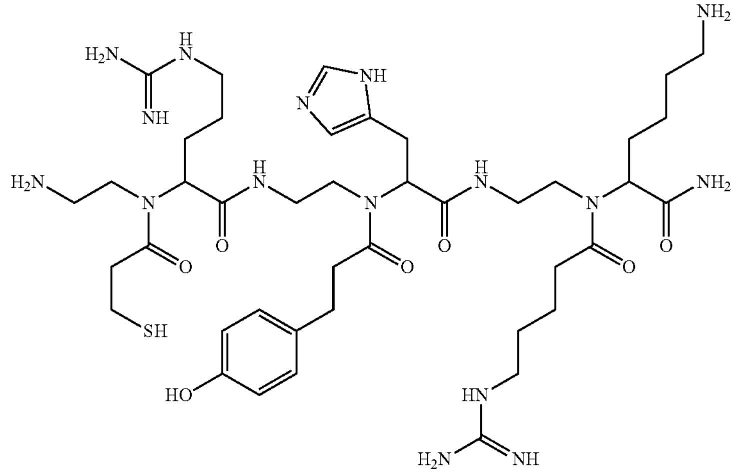 [SMILES: N=C(N)NCCCCC(=O)N(CCNC(=O)C(Cc1cnc[nH]1)N(CCNC(=O)C(CCCNC(=N)N)N(CCN)C(=O)CCS)C(=O)CCc1ccc(O)cc1)C(CCCCN)C(N)=O] | 14.54<br>473.8 |
| Compound 6 | 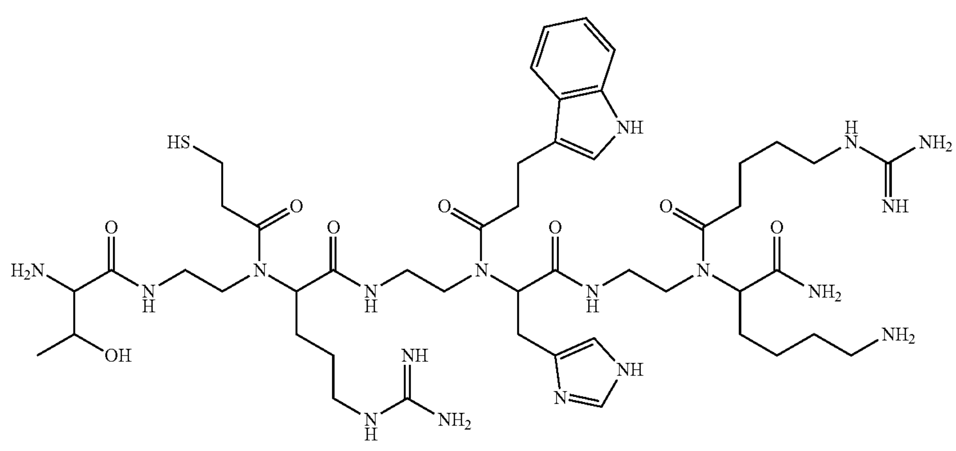 [SMILES: CC(O)C(N)C(=O)NCCN(C(=O)CCS)C(CCCNC(=N)N)C(=O)NCCN(C(=O)CCc1c[nH]c2ccccc12)C(Cc1c[nH]cn1)C(=O)NCCN(C(=O)CCCCNC(=N)N)C(CCCCN)C(N)=O] | 16.99<br>535.8 |

-continued
| Compound | Structure | LC-MS Rt (min) m/z (uma) |
|---|---|---|
| Compound 7 | 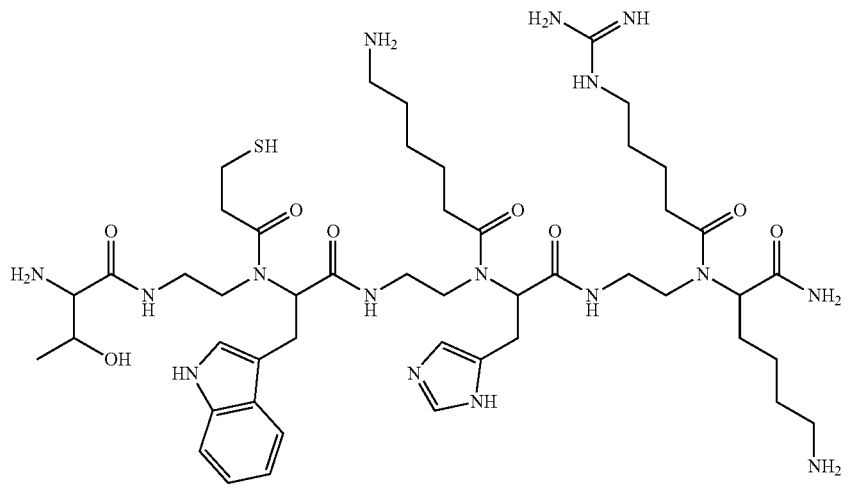 [SMILES: CC(O)C(N)C(=O)NCCN(C(=O)CCS)C(Cc1c[nH]c2ccccc12)C(=O)NCCN(C(=O)CCCCCN)C(Cc1cnc[nH]1)C(=O)NCCN(C(=O)CCCCNC(=N)N)C(CCCCN)C(N)=O] | 16.95 521.8 |
| Compound 8 | 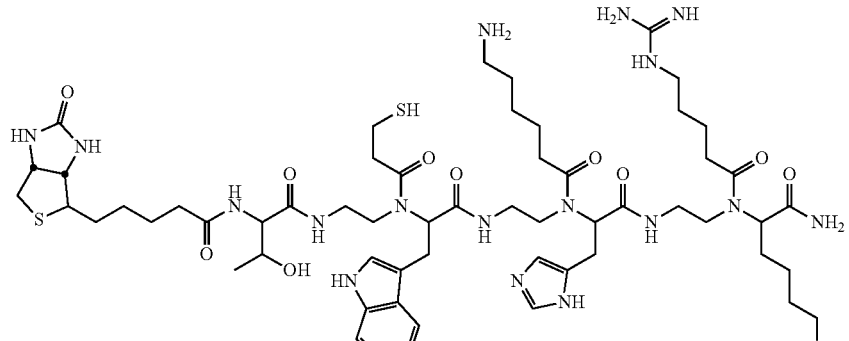 | 18.49 634.8 |
| Compound 9 | 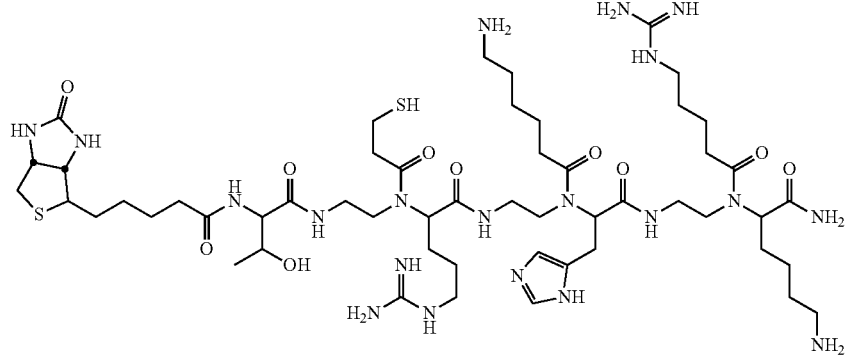 [SMILES: CC(O)C(NC(=O)CCCCC1SC[C@@H]2NC(=O)N[C@H]12)C(=O)NCCN(C(=O)CCS)C(CCCNC(=N)N)C(=O)NCCN(C(=O)CCCCCN)C(Cc1cnc[nH]1)C(=O)NCCN(C(=O)CCCCNC(=N)N)C(CCCCN)C(N)=O] | 15.96 619.9 |
| Compound 10 | 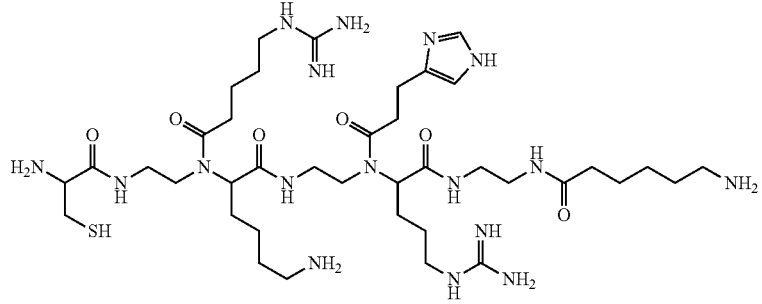 [SMILES: N=C(N)NCCCCC(=O)N(CCNC(=O)C(N)CS)C(CCCCN)C(=O)NCCN(C(=O)CCc1c[nH]cn1)C(CCCNC(=N)N)C(=O)NCCNC(=O)CCCCCN] | 11.85 456.3 |

-continued

| Compound | Structure | LC-MS Rt (min) m/z (uma) |
|---|---|---|
| Compound 11 | 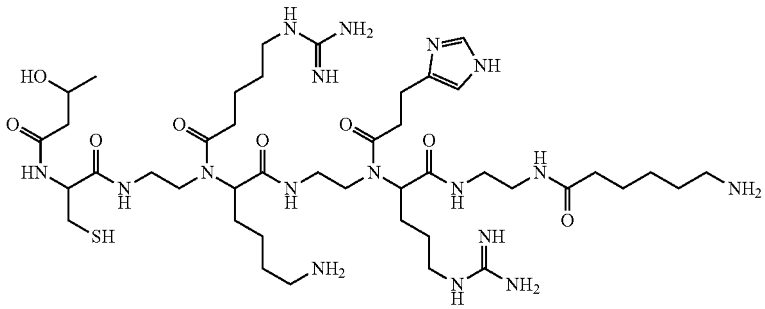 [SMILES: CC(O)CC(=O)NC(CS)C(=O)NCCN(C(=O)CCCCNC(=N)N)C(CCCCN)C(=O)NCCN(C(=O)CCc1c[nH]cn1)C(CCCNC(=N)N)C(=O)NCCNC(=O)CCCCCN] | 12.90<br>499.3 |
| Compound 12 | 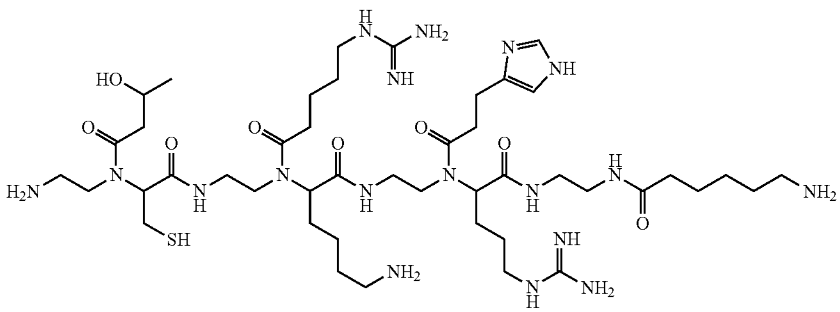 [SMILES: CC(O)CC(=O)N(CCN)C(CS)C(=O)NCCN(C(=O)CCCCNC(=N)N)C(CCCCN)C(=O)NCCN(C(=O)CCc1c[nH]cn1)C(CCCNC(=N)N)C(=O)NCCNC(=O)CCCCCN] | 12.85<br>520.4 |
| Compound 13 | 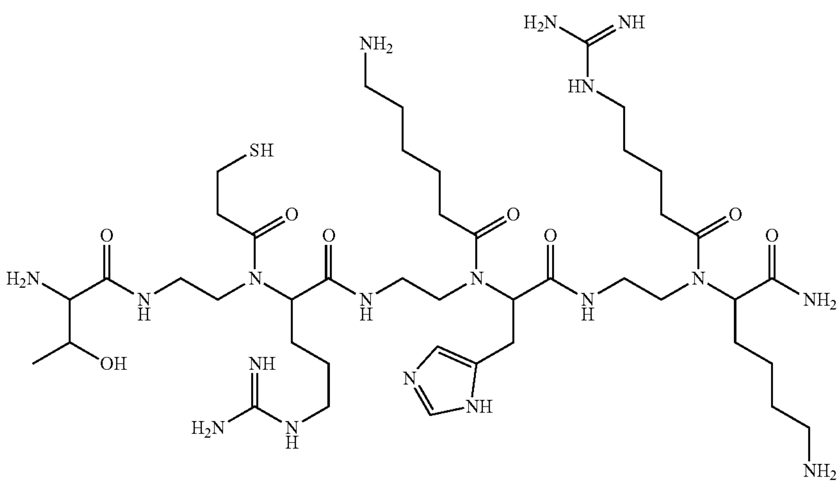 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCCCNC(=N)N)C(CCCCN)C(N)=O] | 12.56<br>506.8 |
| Compound 14 | 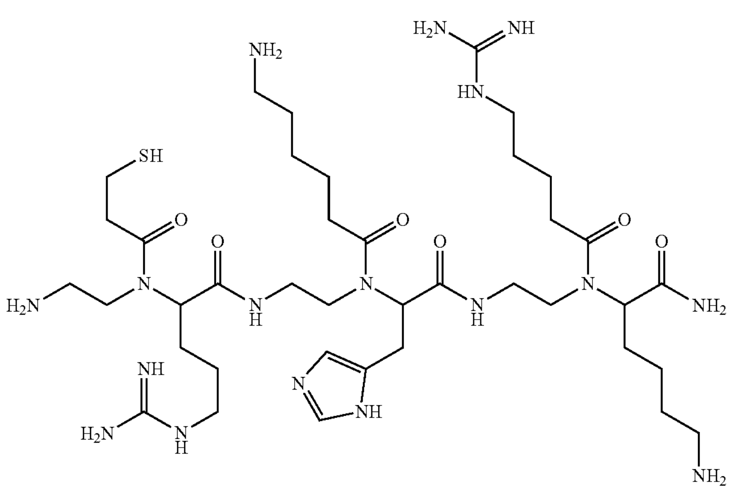 [SMILES: N=C(N)NCCCCC(=O)N(CCNC(=O)C(Cc1cnc[nH]1)N(CCNC(=O)C(CCCNC(=N)N)N(CCN)C(=O)CCS)C(=O)CCCCCN)C(CCCCN)C(N)=O] | 11.83<br>456.3 |

| Compound | Structure | LC-MS Rt (min) m/z (uma) |
|---|---|---|
| Compound 15 | 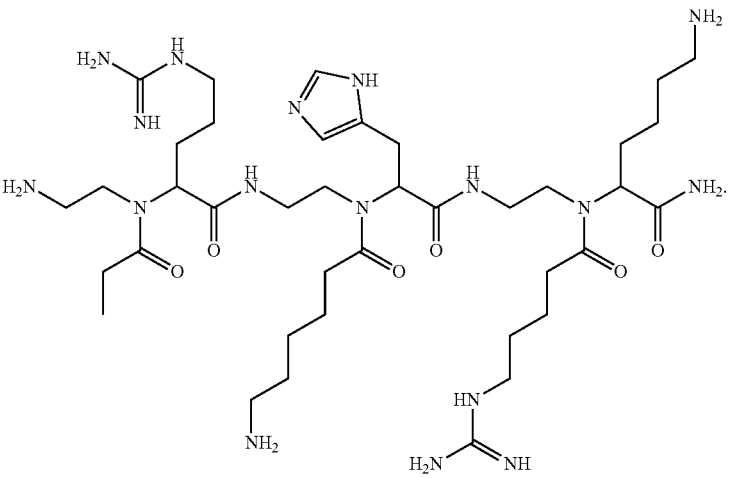 [SMILES: CCC(=O)N(CCN)C(CCCNC(=N)N)C(=O)NCCN(C(=O)CCCCCN)C(Cc1cnc[nH]1)C(=O)NCCN(C(=O)CCCCNC(=N)N)C(CCCCN)C(N)=O] | 11.86<br>440.3 |
| Compound 16 | 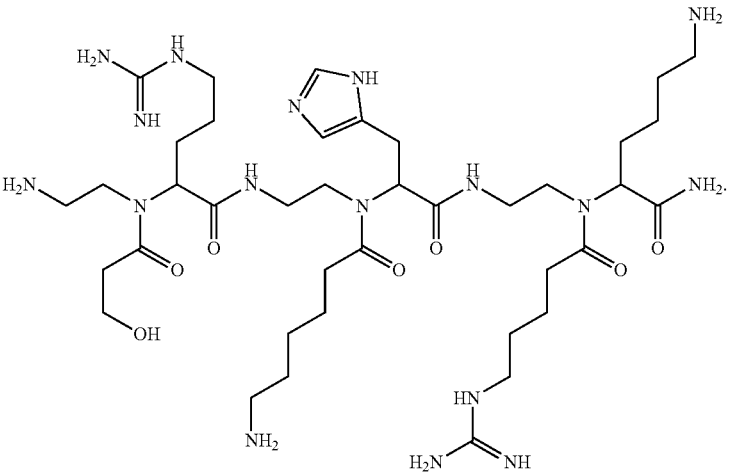 [SMILES: N=C(N)NCCCCC(=O)N(CCNC(=O)C(Cc1cnc[nH]1)N(CCNC(=O)C(CCCNC(=N)N)N(CCN)C(=O)CCO)C(=O)CCCCCN)C(CCCCN)C(N)=O] | 11.01<br>448.8 |
| Compound 17 | 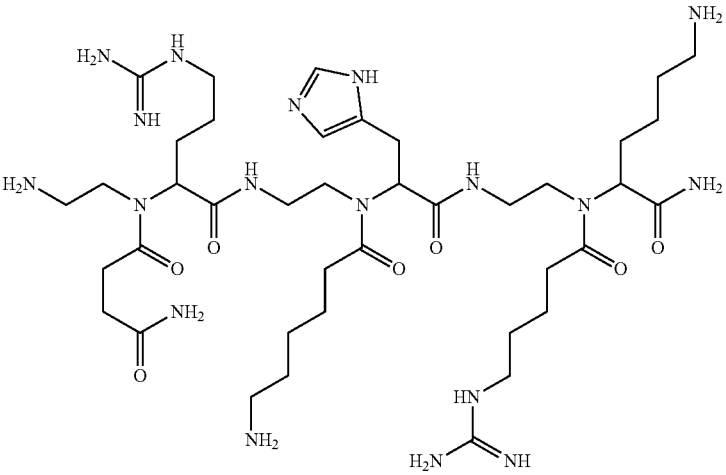 [SMILES: N=C(N)NCCCCC(=O)N(CCNC(=O)C(Cc1cnc[nH]1)N(CCNC(=O)C(CCCNC(=N)N)N(CCN)C(=O)CCC(N)=O)C(=O)CCCCCN)C(CCCCN)C(N)=O] | 10.96<br>461.8 |

-continued
| Compound | Structure | LC-MS Rt (min) m/z (uma) |
|---|---|---|
| Compound 18 | 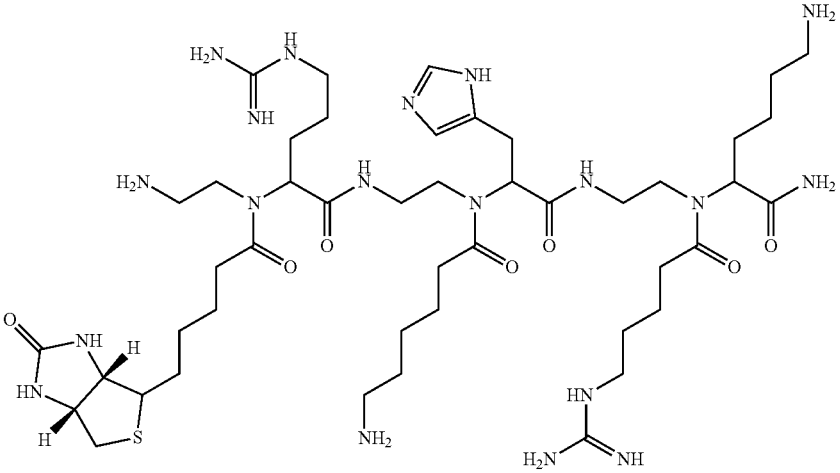 [SMILES: N=C(N)NCCCCC(=O)N(CCNC(=O)C(Cc1cnc[nH]1)N(CCNC(=O)C(CCCNC(=N)N)N(CCN)C(=O)CCCCC1SC[C@@H]2NC(=O)N[C@H]12)C(=O)CCCCCN)C(CCCCN)C(N)=O] | 13.27 525.3 |
| Compound 19 | 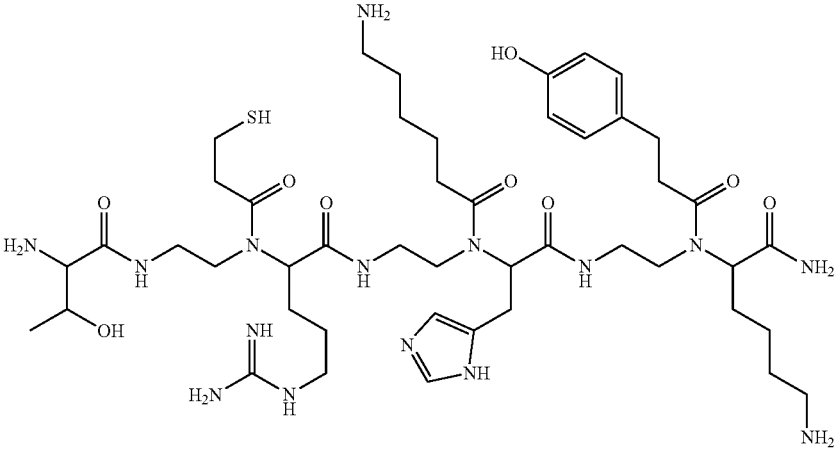 | |
| Compound 20 | 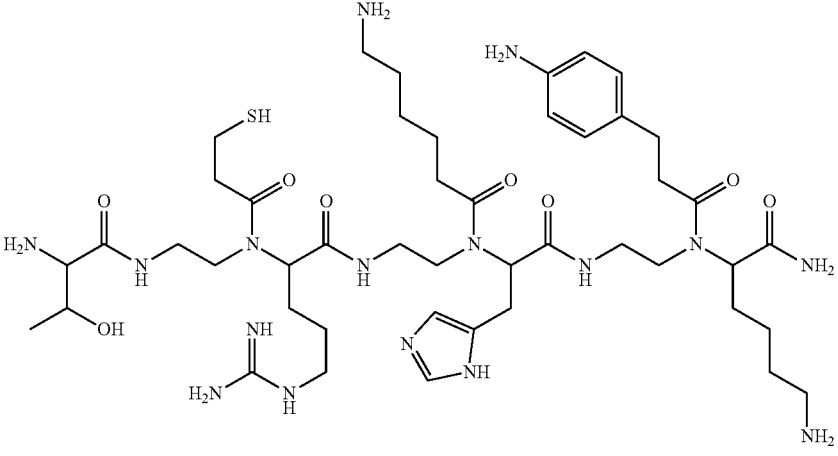 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCc1ccc(N)cc1)C(CCCCN)C(N)=O] | |

| Compound | Structure | LC-MS Rt (min) m/z (uma) |
|---|---|---|
| Compound 21 | 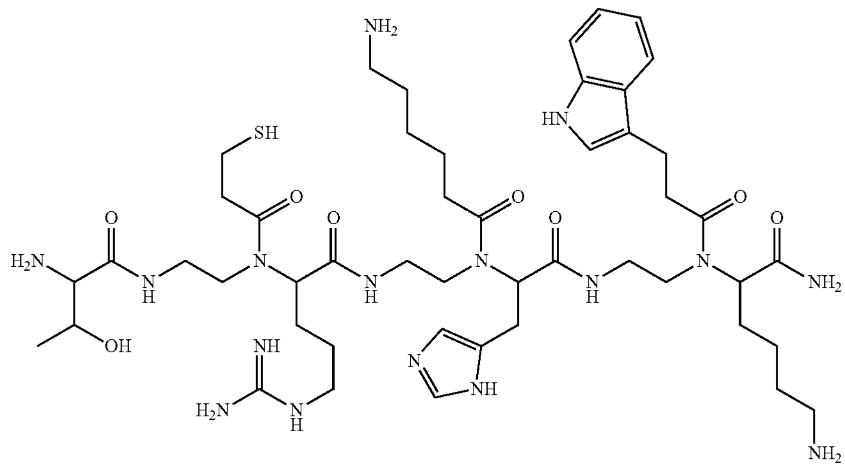 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCc1c[nH]c2ccccc12)C(CCCCN)C(N)=O] | |
| Compound 22 | 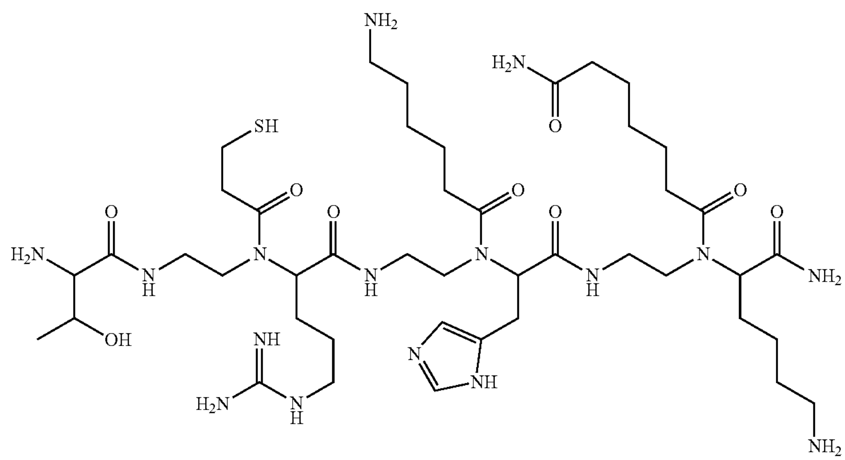 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCCCCC(N)=O)C(CCCCN)C(N)=O] | |
| Compound 23 | 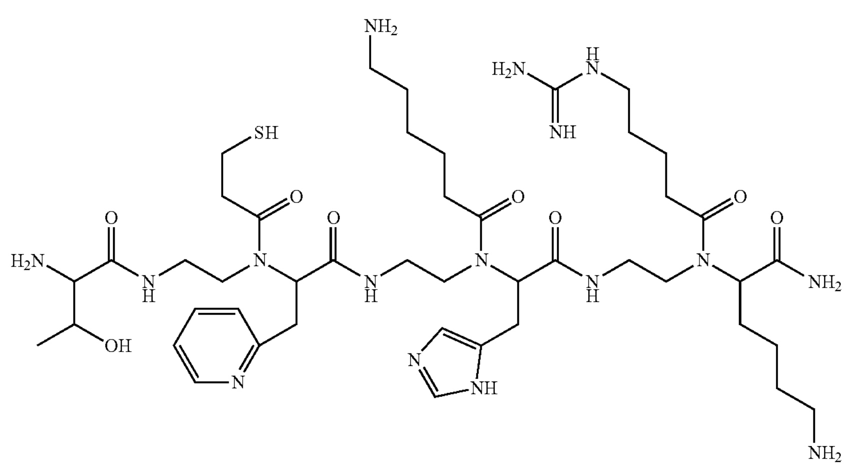 [SMILES: CC(O)C(N)C(=O)NCCN(C(=O)CCS)C(Cc1ccccn1)C(=O)NCCN(C(=O)CCCCCN)C(Cc1cnc[nH]1)C(=O)NCCN(C(=O)CCCCNC(=N)N)C(CCCCN)C(N)=O] | |

| Compound | Structure | LC-MS Rt (min) m/z (uma) |
|---|---|---|
| Compound 24 | 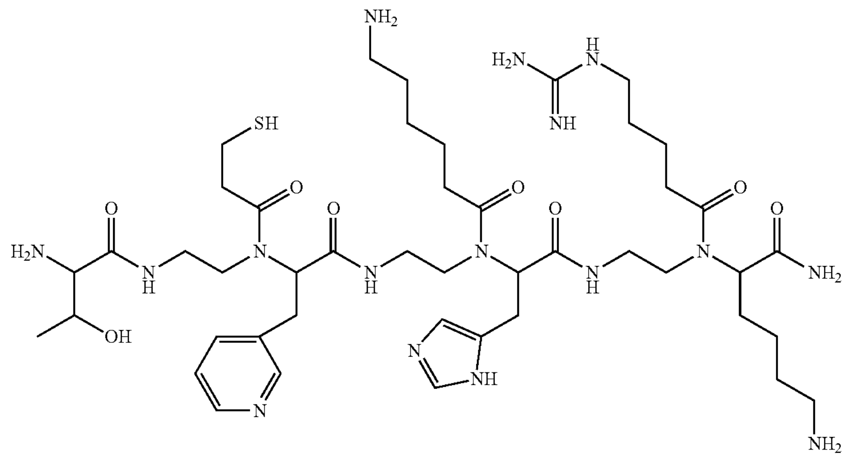 [SMILES: CC(O)C(N)C(=O)NCCN(C(=O)CCS)C(Cc1cccnc1)C(=O)NCCN(C(=O)CCCCCN)C(Cc1cnc[nH]1)C(=O)NCCN(C(=O)CCCCNC(=N)N)C(CCCCN)C(N)=O] | |
| Compound 25 | 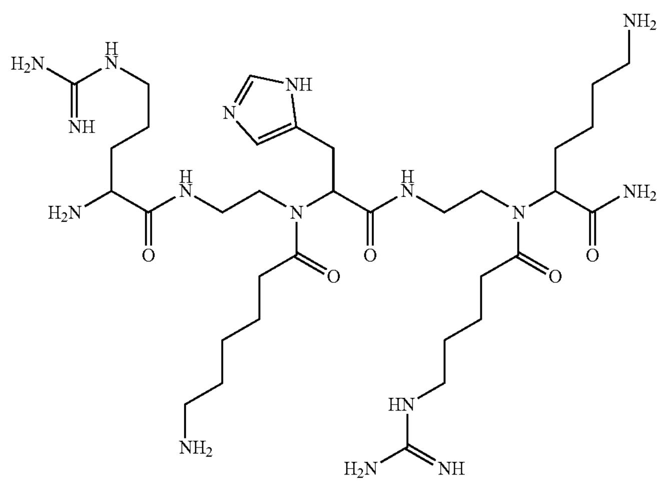 [SMILES: N=C(N)NCCCCC(=O)N(CCNC(=O)C(Cc1cnc[nH]1)N(CCNC(=O)C(N)CCCNC(=N)N)C(=O)CCCCCN)C(CCCCN)C(N)=O] | |
| Compound 26 | 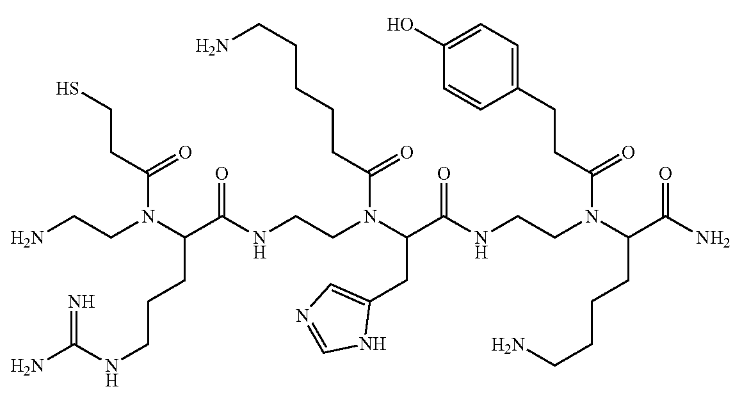 | 14.61 459.8 |

| Compound | Structure | LC-MS Rt (min) m/z (uma) |
|---|---|---|
| Compound 27 | 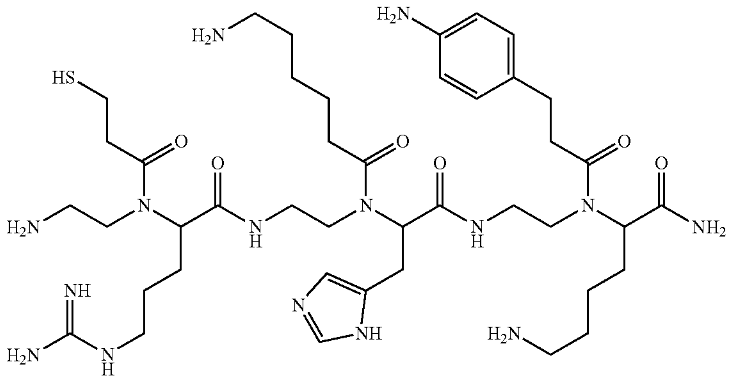 [SMILES: N=C(N)NCCCC(C(=O)NCCN(C(=O)CCCCCN)C(Cc1cnc[nH]1)C(=O)NCCN(C(=O)CCc1ccc(N)cc1)C(CCCCN)C(N)=O)N(CCN)C(=O)CCS] | 12.66 459.3 |
| Compound 28 | 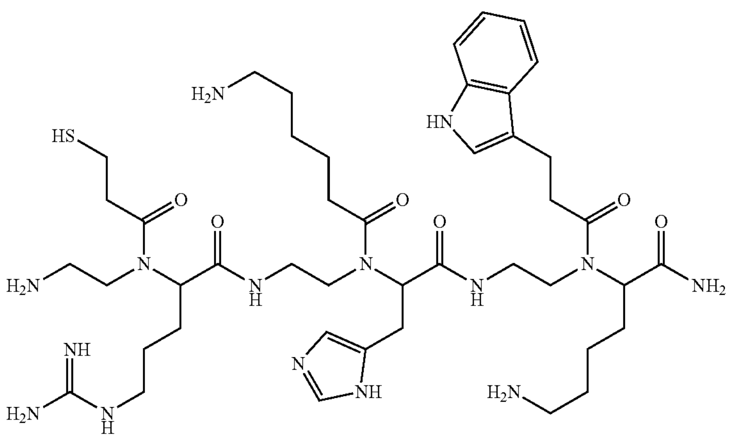 [SMILES: N=C(N)NCCCC(C(=O)NCCN(C(=O)CCCCCN)C(Cc1cnc[nH]1)C(=O)NCCN(C(=O)CCc1c[nH]c2ccccc12)C(CCCCN)C(N)=O)N(CCN)C(=O)CCS] | 17.21 471.3 |
| Compound 29 | 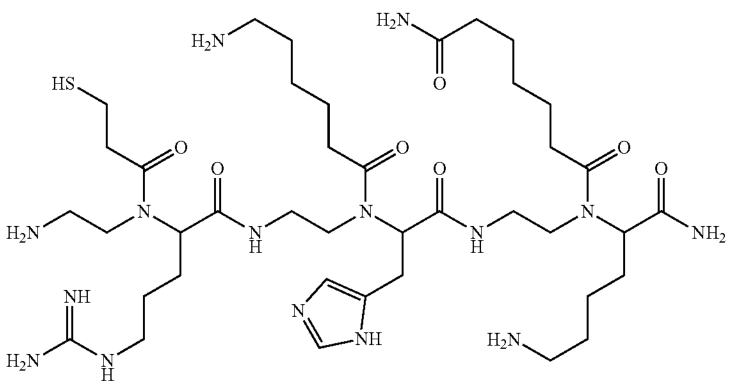 [SMILES: N=C(N)NCCCC(C(=O)NCCN(C(=O)CCCCCN)C(Cc1cnc[nH]1)C(=O)NCCN(C(=O)CCCCCC(N)=O)C(CCCCN)C(N)=O)N(CCN)C(=O)CCS] | 12.56 456.3 |
| Compound 30 | 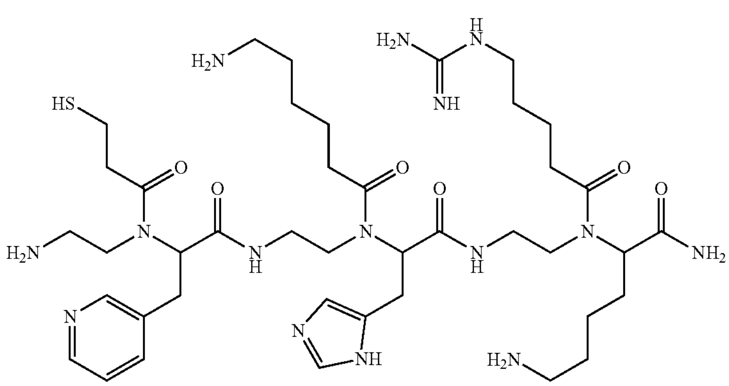 [SMILES: N=C(N)NCCCCC(=O)N(CCNC(=O)C(Cc1cnc[nH]1)N(CCNC(=O)C(Cc1cccnc1)N(CCN)C(=O)CCS)C(=O)CCCCCN)C(CCCCN)C(N)=O] | 15.08 452.3 |

| Compound | Structure | LC-MS Rt (min) m/z (uma) |
|---|---|---|
| Compound 31 | 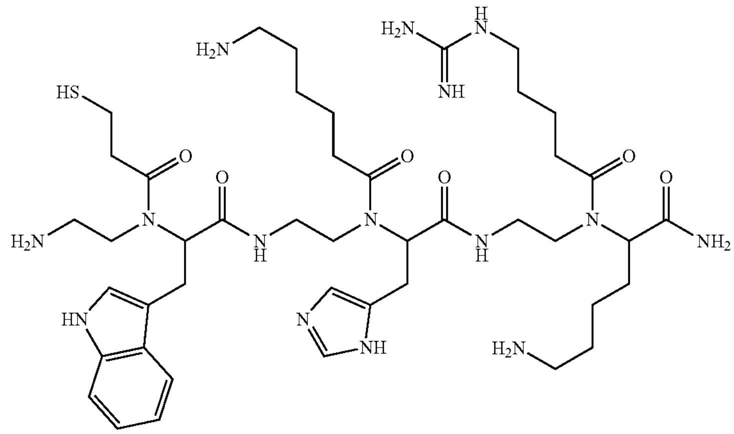 [SMILES: N=C(N)NCCCCC(=O)N(CCNC(=O)C(Cc1cnc[nH]1)N(CCNC(=O)C(Cc1c[nH]c2ccccc12)N(CCN)C(=O)CCS)C(=O)CCCCCN)C(CCCCN)C(N)=O] | 16.91 471.3 |

Compound 8 corresponds to compound 7 biotinylated on $P_1$.

Compound 9 corresponds to compound 13 biotinylated on $P_1$.

Compound 18 corresponds to compound 14 (or 15, 16, 17) biotinylated on $P_3$.

In a particular embodiment, a compound of the invention is of formula (A') according to the invention:

$$P_1—P_2—P_3—P_4—P_5—P_6—P_7 \quad (A')$$

wherein:
$P_1$ represents a hydrogen atom or a structure of formula (I), with preferably $R_1$ being a hydrogen atom; and $R_2$ a —$NH_2$ group;

$P_2$ represents a structure of formula (III), with preferably $R_6$ being a hydrogen atom; and $R_7$ a alkyl group substituted with a —SH group;

$P_4$ represents the structure of formula (IX), with preferably $R_{19}$ being a hydrogen atom and $R_{20}$ being a —$NH_2$ group;

$P_5$ represents a structure of formula (XII), with preferably Ar being an imidazole group; $P_6$ represents a structure of formula (XV), with preferably $R_{24}$, $R_{25}$ and $R_{26}$ being a hydrogen atom; Y being NH—; and Z being —NH—;

$P_7$ represents a structure of formula (XIX), with preferably $R_{27}$ and $R_{28}$ being a hydrogen atom; and $P_3$ represents a structure of:
formulae (VII), with preferably $R_{10}$ being an indole, or formula (VIII), with preferably Z being —NH—, Y being NH and $R_{15}$ and $R_{16}$ being a hydrogen atom.

A compound according to the invention is in particular selected from compound 7 or compound 13.

A compound of the invention can be grafted with one or several, preferably one, element(s) selected from the group consisting of:
a reactive moiety;
a targeting agent, for example PEG or biotin;
a dye, such as chromophore;
a fluorophore, in particular rhodamine, fluorescein, BODIPY, indocyanine or 3,6-bis(1-methyl-4-vinylpyridinium);
a chemical tag, in particular a ferrocenyl; and
an immunomodulating agent, for example pomalidomide, in particular pomalidomide using a PEG linker.

Said element can in particular be grafted in any of parts $P_1$, $P_2$, $P_3$, $P_4$, $P_5$, $P_6$ and/or $P_7$ of the compounds of formula (A), and in particular on any free $NH_2$ group present in any of parts $P_1$, $P_2$, $P_3$, $P_4$, $P_5$, $P_6$ and/or $P_7$ of the compounds of formula (A).

Compounds 8 and 9 above illustrate for example the presence of a biotin element grafted on $P_1$ and compound 18 illustrates for example the presence of a biotin element grafted on $P_3$.

The compounds of the invention are peptides which can be synthesized in a simple and highly efficient way by standard solid phase synthesis similarly to the synthesis of conventional peptides, i.e. by assembling amino acids and transposed amino acids building blocks. Transposed amino acids are N-acylated-N-aminoethyl amino acids.

Composition According to the Invention and their Use Thereof

In a preferred embodiment, the compounds of the present invention can be used in a pharmaceutically acceptable medium of a composition.

The present invention thus further relates to a pharmaceutical composition comprising, in a pharmaceutically acceptable medium, one or several compound(s) according to the invention.

The routes of administration and dosage vary depending on a variety of parameters, for example depending on the individual's condition, the type of disease and the severity of the disease to be treated or of the compound(s) of the invention used. The compound according to the invention and the composition according to the invention are especially capable of being administered to an individual in dry, solid (in particular cachet, powder, capsule, pill, granule, suppository, or tablet polymer capsule, specifically accelerated release tablet, enteric tablet or prolonged-release tablets), under gelatinous form, or as a solution, or a liquid suspension (in particular syrup, injectable solution, or oral infusible, microvesicles, liposomes).

These compounds can also be in the form of doses in dry form (powder, lyophilizate, etc.) for reconstitution at the time of use using an appropriate diluent know to the man skilled in the art.

Depending on their dosage form, a composition of the invention may be administered enterally, parenterally (intravenously, intramuscularly or subcutaneous), transdermally (or percutaneous or transdermal), cutaneously, orally, mucosally, in particular transmucosally, buccally, nasally, ophthalmically, otologically (in the ear), esophageally, vaginally, rectally, or intragastrically, intracardiacally, intraperitoneally, intrapulmonaryly or intratracheally.

Furthermore, the compound of the invention or the composition of the invention may be packaged for administration as a single dose (single dose) or multiple (multidose).

To enhance the effects of treatment, it is possible to proceed with an administration in the form of several successive administrations, repeated at one or more occasions after a particular time interval. One can, for example, carry out several administrations per day, per week, per month or per year.

The amount of compound administered to an individual is in a therapeutically effective amount.

A "therapeutically effective amount" is an amount sufficient to produce a significant effect, especially bring a significant benefit to said individual as part of an administration for the prophylaxis or treatment as defined previously.

A therapeutically effective amount is an amount for which the beneficial effects outweigh any toxic or detrimental effect of or ingredient(s) active(s). The therapeutically effective amount will vary depending on factors such as the state of infection, age, sex or weight of the individual.

Dosage regimens may be adjusted to obtain an optimum therapeutic effect.

The daily dosage of the compound of the invention may be varied over a wide range from 0.01 to 1,000 mg per adult per day.

More specifically, a therapeutically effective amount of compound of formula (A) of the invention may be between 40 mg/day and 1600 mg/day, in particular between 80 mg/day and 1200 mg/day, more particularly between 100 mg/day and 800 mg/day, preferably between 200 mg/day and 500 mg/day, administered for example in 1 to 3 doses.

In a particular embodiment, a compound according to the invention is administered in a content of 0.01, 0.05, 0.1, 0.5, 1, 2.5, 5, 10, 15, 25, 50, 100, 250 or 500 mg per day to the subject to be treated.

A pharmaceutical composition, or medicament, of the invention can contain from about 0.01 mg to 500 mg of the compound of the invention, in particular from 1 mg to 100 mg of the compound.

In an embodiment, the present invention indeed relates to a compound or a composition according to the invention for its use as a medicament.

As mentioned above, the present invention more particularly relates to a compound or a composition according to the invention for its use in the reduction of CD95-mediated cell motility in a subject in need thereof.

According to an embodiment, the invention relates to a method for the reduction of CD95-mediated cell motility in a subject in need thereof in a subject comprising administering the subject with a compound or a composition according to the invention.

The invention further relates to a compound or a composition according to the invention for its use in the reduction of CD95-mediated cell motility in a subject in need thereof.

The invention further relates to a compound or a composition according to the invention for its use I the treatment of cancer in a subject in need thereof.

Such cancer can in particular be selected from neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; bronchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

According to this use and methods, the subject or individual can suffer from a cancer selected from the group consisting of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers.

Said use or method can furthermore comprise the sequential or concomitant administration of one or more therapeutic active agent such as chemotherapeutic or radiotherapeutic agents. Examples of chemotherapeutics include but are not limited to fludarabine, gemcitabine, capecitabine, methotrexate, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, epipodophyllotoxins such as etoposide and teniposide, camptothecins such as irinotecan and topotecan, bleomycin, doxorubicin, idarubicin, dactinomycin, plicamycin, mitoxantrone, L-asparaginase, doxorubicin, epirubicin, 5-fluorouracil and 5-fluorouracil combined with leucovorin, taxanes such as docetaxel and paclitaxel, levamisole, estramustine, nitrogen mustards, nitrosoureas such as carmustine and lomustine, *vinca* alkaloids such as vinblastine, vincristine, vindesine and vinorelbine, imatinib mesylate, hexamethylmelamine, kinase inhibitors, phosphatase inhibitors, ATPase inhibitors, tyrphostins, protease inhibitors, inhibitors herbimycin A, genistein, erbstatin, and lavendustin A. In some embodiments, additional therapeutic active agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxins, hormonal therapies, retinoids, photosensitizers or photodynamic therapies, angiogenesis inhibitors, antimitotic agents, isoprenylation inhibitors, cell cycle inhibitors, actinomycin, bleomycin, anthracyclines, MDR inhibitors and Ca2+ ATPase inhibitors. The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

In some embodiments, the compounds or compositions of the present invention are particularly suitable for the treatment of triple negative breast cancer. As used herein the expression "Triple negative breast cancer" has its general meaning in the art and means that said breast cancer lacks or expresses low levels of receptors for the hormones estrogen (ER-negative) and progesterone (PR-negative), and for the protein HER2.

In some embodiments, the compounds and compositions of the present invention are particularly suitable for the prevention of metastases (e.g. in a subject suffering from a triple negative breast cancer).

In some embodiments, the compounds and compositions of the present invention are particularly suitable for enhancing therapeutic efficacy of cancer treatment in a subject in need thereof.

In some embodiments, the compounds and compositions of the present invention are particularly suitable for inhibiting the B-cell maturation and thus the antibody production. As used herein, the term "B-cell" refers to lymphocytes that are capable of producing antibodies. These cells are the primary cell type involved in humoral acquired immunity.

The invention thus further relates to a compound or composition according to the invention for its use in the reduction of CD95-mediated lymphocyte motility and/or B cell maturation.

The invention also relates to a compound or composition according to the invention for its use in the treatment of an auto-immune inflammatory disease.

Said autoimmune inflammatory disease can in particular be selected from the group consisting of Addison's Disease, Allergy, Alopecia Areata, Alzheimer's disease, Antineutrophil cytoplasmic antibodies (ANCA)-associated vasculitis, Ankylosing Spondylitis, Antiphospholipid Syndrome (Hughes Syndrome), arthritis, Asthma, Atherosclerosis, Atherosclerotic plaque, autoimmune disease (e.g., lupus, (rheumatoid arthritis), multiple sclerosis, Graves' disease, etc.), Autoimmune Hemolytic Anemia, Autoimmune Hepatitis, Autoimmune inner ear disease, Autoimmune Lymphoproliferative syndrome, Autoimmune Myocarditis, Autoimmune Oophoritis, Autoimmune Orchitis, Azoospermia, Behcet's Disease, Berger's Disease, Bullous Pemphigoid, Cardiomyopathy, Cardiovascular disease, Celiac Sprue/Coeliac disease, Chronic Fatigue Immune Dysfunction Syndrome (CFIDS), Chronic idiopathic polyneuritis, Chronic Inflammatory Demyelinating, Polyradicalneuropathy (CIPD), Chronic relapsing polyneuropathy (Guillain-Barré syndrome), Churg-Strauss Syndrome (CSS), Cicatricial Pemphigoid, Cold Agglutinin Disease (CAD), chronic obstructive pulmonary disease (COPD), CREST syndrome, Crohn's disease, Dermatitis, Herpetiformus, Dermatomyositis, diabetes, Discoid Lupus, Eczema, Epidermolysis bullosa acquisita, Essential Mixed Cryoglobulinemia, Evan's Syndrome, Exopthalmos, Fibromyalgia, Goodpasture's Syndrome, Hashimoto's Thyroiditis, Idiopathic Pulmonary Fibrosis, Idiopathic Thrombocytopenia Purpura (ITP), IgA Nephropathy, immunoproliferative disease or disorder (e.g., psoriasis), Inflammatory bowel disease (IBD), including Crohn's disease and ulcerative colitis, Insulin Dependent Diabetes Mellitus (IDDM), Interstitial lung disease, juvenile diabetes, Juvenile Arthritis, juvenile idiopathic arthritis (JIA), Kawasaki's Disease, Lambert-Eaton Myasthenic Syndrome, Lichen Planus, lupus, Lupus Nephritis, Lymphoscytic Lypophisitis, Ménière's Disease, Miller Fish Syndrome/acute disseminated encephalomyeloradiculopathy, Mixed Connective Tissue Disease, Multiple Sclerosis (MS), muscular rheumatism, Myalgic encephalomyelitis (ME), Myasthenia Gravis, Ocular Inflammation, Pemphigus Foliaceus, Pemphigus Vulgaris, Pernicious Anaemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune cholangiopathy, Psoriasis, Psoriatic arthritis, Raynaud's Phenomenon, Reiter's Syndrome/Reactive arthritis, Restenosis, Rheumatic Fever, rheumatic disease, Rheumatoid Arthritis, Sarcoidosis, Schmidt's syndrome, Scleroderma, Sjörgen's Syndrome, Stiff-Man Syndrome, Systemic Lupus Erythematosus (SLE), systemic scleroderma, Takayasu Arteritis, Temporal Arteritis/Giant Cell Arteritis, Thyroiditis, Type 1 diabetes, Type 2 diabetes, Ulcerative colitis, Uveitis, Vasculitis, Vitiligo, and Wegener's Granulomatosis.

In some embodiments, the compounds and compositions of the present invention are particularly suitable for the treatment of systemic lupus erythematosus.

In some embodiments, the compounds and compositions of the present invention are particularly suitable for the treatment of antibody-mediated diseases, including but not limited to graft rejection, graft vs. host disease, and inflammatory-autoimmune diseases (as described above). In addition, the compounds and compositions of the present invention are particularly suitable for the treatment B-cell tumors, such as multiple myeloma and chronic lymphocytic leukemia.

Accordingly, the present invention also relates to compounds and composition according to the invention for its use:
  in the treatment of antibody-mediated diseases, including but not limited to graft rejection, graft vs. host disease, and inflammatory-autoimmune diseases; and/or
  in the treatment of B-cell tumors, such as multiple myeloma and chronic lymphocytic leukemia.

The pharmaceutical compositions according to the invention can in particular contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions.

In all cases, the form must be sterile and must be fluid to the extent that easy syringability exists. It must be stable under the conditions of manufacture and storage and must be preserved against the contaminating action of microorganisms, such as bacteria and fungi. Sterile injectable solutions are prepared by incorporating the compound at the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The invention will be further illustrated by the following figures and examples. However, these examples and figures should not be construed in any way as limiting the scope of the present invention.

EXAMPLES

Materials and Methods

Patients

All human volunteers/patients were enrolled in this study after they signed a written inform consent. Only patients with plasma HIV-RNA copy number below 40 per mL and a CD4+ T cell count stable for one year were included in this study.

Cell Lines and Peripheral Blood Lymphocytes.

All cells were purchased from ATCC (Molsheim Cedex, France). The T cell lines H9 and CEM were cultured in RPMI supplemented with 8% heat-inactivated FCS (v/v) and 2 mM L-glutamine at 37° C./5% $CO_2$. HEK293T cells were cultured at 37° C./5% $CO_2$ in DMEM supplemented with 8% heat-inactivated FCS and 2 mM L-glutamine. PBMCs were isolated from buffy-coat by density gradient centrifugation on lymphocyte separation medium (Eurobio, Les Ulis, France). Th17 cells (CD4+CCR6+CXCR3−) were sorted from PBMCs using a Th17 Enrichment kit (StemCell Technologies, Grenoble, France). Human umbilical vein endothelial cells (HUVEC) were grown in Endothelial Growth Medium (EGM) supplemented with 2% FCS and EGM-2 Bullet Kit (Lonza, Levallois-Perret, France).

Reagents and Antibodies

The anti-CD95 mAb (clone APO1.3) was from Enzo Life Sciences (Villeurbanne, France). The anti-CD95 (C-20) mAbs were purchased from Santa Cruz Biotechnology (Heidelberg, Germany) and anti-PLCγ1 was from Millipore (Molsheim, France). Anti-CCR6 (G034E3) and anti-CXCR3 (G025H7) were purchased from BioLegend (ThermoFisher Scientific, Cergy-Pontoise, France).

Transendothelial Migration of Activated T Lymphocytes

Boyden chamber membranes (3 μm pore size) were hydrated with sterile D-PBS (Millipore, Molsheim, France). To form a monolayer of HUVEC ($2·10^5$ cells), cells were placed on the upper side of Boyden chamber membrane and cultured for 24 h. Thereafter, T lymphocytes ($3·10^5$ cells) were added to the top chamber in a low serum (1%)-containing medium and the bottom chamber was filled with low serum (1%)-containing medium complemented with or without cl-CD95L (100 ng/mL). Cells were cultured for 24 h at 37° C. in a 5% $CO_2$, humidified incubator. Transmigrating cells present in the lower chamber were stained using a fluorescent marker (CyQUANT-Dye®, Millipore, Molsheim, France) and lyzed for quantification.

Pull-Down Assay

HEK-293T cells co-transfected with PLCγ1 and CD95-containing vectors. After 24 h, transfected cells were lysed in Hepes Buffer (Hepes 25 mM, NaCl 150 mM, NaDF 2 mM, NaVO$_4$ 1 mM, EGTA 2 mM). Cell lysates were incubated for 30 min at 4° C. with or without 50 mM of biotin-conjugated drugs and then overnight at 4° C. with 30 μl of streptavidin magnetic beads (Ademtech, Pessac, France). After extensive washing in Hepes buffer, the precipitated complex was resolved by SDS-PAGE and immunoblotting was performed with the indicated antibodies.

Statistical Analyses

Statistical tests were calculated in GraphPad Prism (unpaired Mann-Whitney or Student's t tests). The details of the statistical tests carried out are indicated in respective figure legends. Mice were randomized in different groups before being assayed.

Chemistry

α-AApeptides were synthesized according to the Fmoc/Bn or Fmoc/All strategy. Building blocks consisting in a dipeptide mimetic, were prepared from Fmoc-protected natural amino acids via a sequence involving chain extension and N-acylation. These building blocks were then assembled in solution phase through iterative peptide coupling and deprotection steps. Building block corresponding to $P_6$-$P_7$ was prepared as followed: The Fmoc-protected amino acid was coupled to tritylamine through the formation of a mixte anhydride using methyl chloroformate in tetrahydrofurane in the presence of a base. Then the Fmoc protecting group was removed using piperidine in tetrahydrofurane or DBU in dichloromethane. Reductive amination of the resulting primary amine with Fmoc-glycinaldehyde was performed with sodium triacetoxyborohydride in 1,2-dichloroethane. The N-acylation allowing the introduction of the $P_6$ mimic was carried out with the latter secondary amine and the corresponding carboxylic acid using one of the following conditions: COMU ((1-cyano-2-ethoxy-2-oxoethylidenaminooxy)dimethylamino-morpholino-carbenium hexafluorophosphate), DEPBT (3-(diethoxyphosphoryloxy)-1,2,3-benzotriazin-4(3H)-one) or T3P® (propylphosphonic anhydride) in the presence of a base in ethyl acetate or DMF, or EEDQ (2-ethoxy-1-ethoxycarbonyl-1,2-dihydroquinoline) in THF. Finally, the Fmoc protecting group was removed in a classical fashion. For building blocks consisting in P4-P5 or P2-P3, the synthesis was the same unless the first step (benzyl or allyl esterification of the Fmoc protected amino acid to produce the corresponding ester), and the last step (ester deprotection=hydrogenolysis for benzyl ester and Tsuji-Trost reaction for allyl ester). Finally, the building blocks were assembled via peptide coupling with COMU in the presence of Hunig's base and global deprotection of the protected α-AApeptides was achieved with 90:5:5 $CF_3CO_2H/H_2O/Et_3SiH$ (or 90:3.3:3.3:3.3 $CF_3CO_2H/H_2O/iPr_3SiH/CH_2C_{12}$ for mimetics containing indol). Purifications were done by semiprepaprative LC on a Shimadzu Prominence system using Hypersil Gold aQ column chromatography (5μ, 250×20 mm) [method: binary gradient, solvent A=$H_2O$+0.1% TFA, solvent B=MeCN+0.1% TFA, λ=215 nm, flow=10 mL/min, 0→5 min 100% A, 5→15 min 0→30% B/A, 15→20 min 30% B/A, 20→25 min 30→100% B/A, 25→35 min 100% B, 35→40 min 100→0% B/A, 40→50 min 100% A]. LC-MS analysis were performed on a Shimadzu Prominence system couple to an Advion ESI mass spectrometer using Thermoscientific Hypersil Gold aQ column chromatography (5μ, 250×4.6 mm) [method: binary gradient, solvent A=$H_2O$+0.1% TFA, solvent B=MeCN+0.1% TFA, flow=1 mL/min, 0→0.5 min 100% A, 0.5→20 min 0→32% B/A, 20→30 min 32→100% B/A, 30→40 min 100% B, 40→45 min 100→0% B/A, 45→60 min 100% A].

Example 1

Compounds of the Invention Inhibit CD95-Mediated PLCγ1 Recruitment, Calcium Signaling, and Endothelial Transmigration of Th17 T Cells.

A. $SH_3$—PLCγ1-F1 or DD-FADD-F1 (inset) was co-transfected into HEK293T cells along with whole CID-CD95-F2 or DD-CD95-F2 (inset). After 24 h, cells were exposed for 4 h to different compounds according to the invention at different concentrations and luminescence was assessed. The tested compounds were the compounds number 2, 3, 4, 5, 6, 7, 10, 11, 13 and 14.

F1 corresponds to the N-terminal domain of Renilla luciferase enzyme split into two fragments (F1 and F2, F2 being the C-terminal domain—see Stefan, E. et al. Proc Natl Acad Sci USA 104, 16916-21 (2007)). These F1 and F2 domains were co-expressed in HEK cells, whereupon the interaction between CD95-CID and PLCγ1, or CD95-DD and DD-FADD, allowed protein refolding and subsequent recovery of Renilla luciferase activity.

CID corresponds to amino acids 175 to 210 of CD95; DD corresponds to amino acids 210 to 303 of CD95.

Similar experiments were performed using the minimum domain of CID (called minCID) that is required for interaction with PLCγ1 as positive control instead of compound 13. Computer modeling estimated that minCID corresponds to the amino acids 182-188 (TCRKHRK) (SEQ ID NO: 1) of human CD95.

Renilla luciferase-based protein-fragment complementation assay (PCA): HEK293T cells were electroporated with 10 μg DNA using a BTM-830 electroporation generator (BTX Instrument Division, Harvard Apparatus). Transfected cells were cultured for 24 h prior to PCA analyses as previously described (Poissonnier, A. et al., Immunity. 2016, 45, 209-223). Briefly, transfected cells ($10^6$) were washed and resuspended in 100 μL PBS and placed in OptiPlate-96 plates (Perkin-Elmer, Waltham, Mass., USA). Coelenterazine-h (5 μM, Sigma-Aldrich) was added to each well and Renilla luciferase activity was monitored for the first 10 seconds using Infinite200Pro (Tecan, Männedorf, Switzerland).

The results obtained are represented in FIGS. 1A, 1B and 1C. Data represent the mean±SD of three independent experiments.

As observed in FIGS. 1A, 1B and 1C, compounds 2 to 6, 10, 11, 13 and 14 indicated above disrupt the CD95/PLCγ1 interaction without affecting the CD95/FADD interaction. The same applies with the other compounds indicated above (data not shown).

The $IC_{50}$ values obtained with compounds 1 to 7, 10 to 17, 26 to 28, 30 and 31 are represented in the following Table 1.

TABLE 1

| Compound | IC50 SH3-PLCg1/ CID-CD95 (μM) | IC50 DD-FADD/ DD-CD95 (μM) |
|---|---|---|
| 1 | 34.68 | 33.18 |
| 2 | 315.10 | 310.80 |
| 3 | 185.40 | 245.70 |
| 4 | 203.20 | 244.60 |
| 5 | 196.30 | 212.80 |
| 6 | 356.30 | 276.90 |
| 7 | 78.63 | 324.90 |
| 10 | 399.80 | 447.80 |
| 11 | 308.50 | 628.80 |
| 12 | 229.40 | 318.80 |
| 13 | 77.24 | ns |
| 14 | 75.15 | 3800.00 |
| 15 | 60.94 | 163.60 |
| 16 | 78.99 | 3926.00 |
| 17 | 342.60 | 720.50 |
| 26 | 655.00 | 872478.00 |
| 27 | 855.80 | 919761436125.00 |
| 28 | 343.30 | 2647.00 |
| 30 | 906.80 | 4252.00 |
| 31 | 85.55 | 173.40 |

It can be seen that the compounds according to the invention are highly specific for the interaction CD95/PLCγ1 compared to the interaction between CD95/FADD and are thus able to disrupt the CD95/PLCγ1 interaction without affecting the CD95/FADD interaction.

In particular, compounds 7, 11, 13, 14 to 17 and 26 to 30 appear to be particularly specific for the interaction CD95/PLCγ1 compared to the interaction between CD95/FADD.

Moreover, compounds 1, 7, 13, 14, 15, 16, and 31 have a particularly low IC50 values regarding the CD95/PLCγ1 interaction.

B. To establish that compound 13 targeted PLCγ1, we conjugated it to biotin (compound 9) and performed a pull-down assay. HEK cells were transfected with CD95 and PLCγ1. After 24 h, cells were lysed and treated for 30 min with/without 50 µM biotin-conjugated compound 13 (i.e. compound 9), followed by precipitation with streptavidin magnetic beads. The precipitated complex was then resolved in SDS-PAGE gels and immunoblotted with appropriate antibodies.

The result obtained is represented in FIG. 2.

As observed in FIG. 2, biotin-conjugated compound 13 interacts with endogenous PLCγ1.

C. To determine the ability of compounds 7 and 13 to abrogate the binding of PLCγ1 to CD95, HEK cells were transfected with CD95 and PLCγ1. Cells were then pre-incubated for 1 h with the indicated compounds (each at 50 µM), followed by stimulation for 5 min with cl-CD95L (100 ng/mL). CD95 was immunoprecipitated and the immune complex was resolved in SDS-PAGE gels prior to immunoblotting as indicated. Total lysate served as a control.

The results obtained are represented in FIG. 3A. Data represent the mean±SD.

Mouse PBLs were moreover loaded with Fluo2 LR-AM (2 µM) and pre-treated for 1 h with non-toxic concentrations of compound 7 or compound 13. T cells were then stimulated with cl-CD95L (100 ng/mL; arrow in the Figure). Ratio Values® were normalized to pre-stimulated values (R0) to yield R/R0 values.

The results obtained are represented in FIG. 3B. Data represent the mean±SD.

As observed in FIGS. 3A and 3B, compounds 7 and 13 abrogate binding of PLCγ1 to CD95 in cells exposed to cl-CD95L, compound 7 more efficiently than compound 13.

D. In order to assess the superior ability of compound 7 compared to compound 13 to abrogate binding of PLCγ1 to CD95 in cells exposed to cl-CD95L, a graph representing the area under the curve (AUC) measured from the CD95-mediated $Ca^{2+}$ responses show in FIG. 4 was generated. See FIG. 4.

This graph confirms the more efficient ability of compound 7 to abrogate binding of PLCγ1 to CD95 in cells exposed to cl-CD95L, compared to compound 13.

E. The ability of compound 13 to inhibit the CD95-mediated $Ca^{2+}$ response as also be assessed.

Th17 cells were pre-incubated for 1 h with TAT-control, minCID, or compound 13 (each at 1 µM), and then stimulated with cl-CD95L (100 ng/mL). $[Ca^{2+}]_{CYT}$ was assessed in Fluo2 LR-AM (2 µM)-loaded cells.

The results obtained are represented in FIG. 5. Data represent the mean±SD of three independent experiments.

As observed in FIG. 5, pre-incubation of Th17 cells with a non-toxic dose of compound 13 inhibited the CD95-mediated $Ca^{2+}$ response in a manner similar to human minCID.

F. The ability of compound 13 to prevent Th17 trafficking across endothelial cells as also been assessed.

Th17 cells were pre-incubated for 1 h with TAT-control, TAT-CID, TAT-minCID, or minCID (each at 1 µM), or with compound 13 (at 1 or 10 µM), and then stimulated with cl-CD95L (100 ng/mL). Transendothelial migration of T cells was assessed in a Boyden chamber.

The data obtained are represented in FIG. 6. Data represent the mean±SD of three independent experiments.

As observed in FIG. 6, pre-incubation of Th17 cells with a non-toxic dose of compound 13 prevented Th17 trafficking across endothelial cells.

Example 2

Compounds of the Invention Alleviate Clinical Symptoms in Lupus Mice

Next, we asked whether compound 13 exhibited therapeutic activity in lupus-prone mice.

Patients with autoimmune lymphoproliferative syndrome (ALPS) type Ia harbor heterozygous germline variants of CD95 and rarely experience loss of heterozygosity (LOH). Because these patients exhibit SLE-like autoimmunity, we studied the effect of compound 13 in lupus-prone mice harboring a heterozygous CD95 mutation (Lpr).

Similar to ALPS type Ia patients, MRL1pr/+ mice show reduced expression of CD95 due to insertion of a retrotransposon into intron 2 of the CD95 gene; thus the mice develop lupus and lupus-like symptoms, including glomerulonephritis and kidney failure. After the first onset of the disease (i.e., increased proteinuria and detection of serum anti-dsDNA Ig), lupus mice received compound 13 or vehicle (control) three times per week for 5 weeks.

MRLLpr/+ mice injected with compound 13 (n=6) showed a significant reduction in the number of mesangial proliferation and adhesion of the Bowman's capsule as compared to control mice and showed a marked reduction in the severity of pathological lesions in the glomeruli (See FIG. 7). Pathologic Glomerular damage scores were calculated for each kidney in control and compound 13-treated mice.

Accumulation of C3 in kidney sections of MRL, MRL.Faslpr/lpr, and MRL.Faslpr/+ mice treated (or not) with compound 13 was assessed by microscopy. Improved kidney architecture in compound 13-treated mice was associated with reduced deposition of $C_3$ (data not shown).

In agreement with these findings, we observed a marked increase in serum $C_3$ concentration in compound 13-treated mice compared with control-treated mice.

Moreover, the expression of Th17 markers (RORγt, IL23R, and IL17F) in the kidneys of compound 13-treated mice was significantly lower than that in control mice (P=0.0013). FIG. 8 shows that expression of mRNAs typical of Th17 (ror-γt, i123r, IL17F), Th1 (TBX21, CXCR3, and INFG), or Th2 (GATA3, CCR4, and IL4) signatures in compound 13-treated kidneys compared with that in untreated mice. * p<0.05,  p<0.01, * p<0.001.

Furthermore, it has been observed that accumulated IL17-expressing CD4+ cells in the inflamed kidneys of MRL1pr/+ mice were absent from those of compound 13-treated mice (FIG. 9). IL17-positive cells were assessed in kidneys of indicated mice by densitometry. **** stands for p<0.0001 using were calculated using unpaired Student t-test.

The invention claimed is:
1. A compound comprising N-acylated-N-aminoethyl amino acids, selected from the group consisting of:

| Compound | Structure |
|---|---|
| Compound 1 | 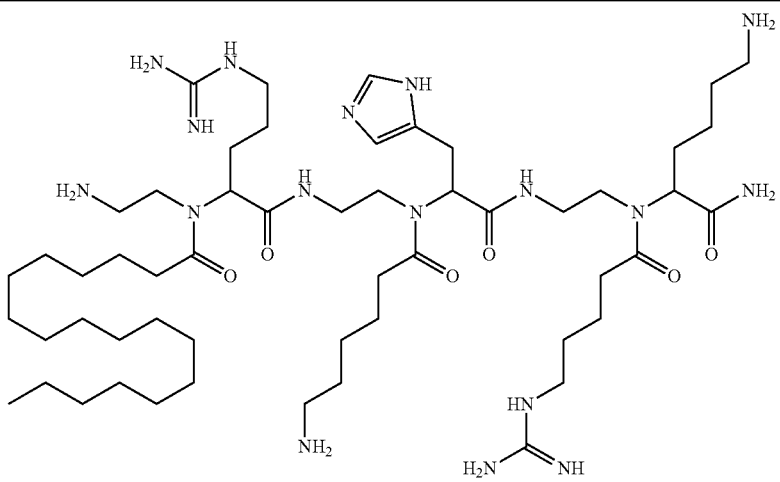 |
| Compound 2 | 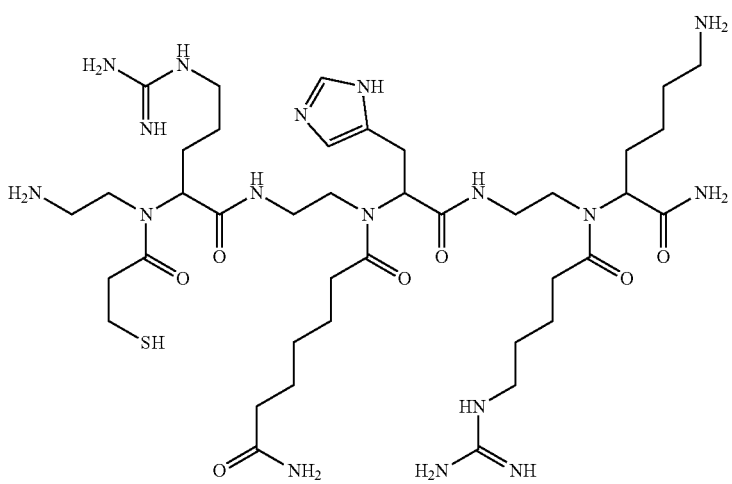 [SMILES: N=C(N)NCCCCC(=O)N(CCNC(=O)C(Cc1cnc[nH]1)N(CCNC(=O)C(CCCNC(=N)N)N(CCN)C(=O)CCS)C(=O)CCCCCC(N)=O)C(CCCCN)C(N)=O] |

-continued
| Compound | Structure |
|---|---|
| Compound 3 | 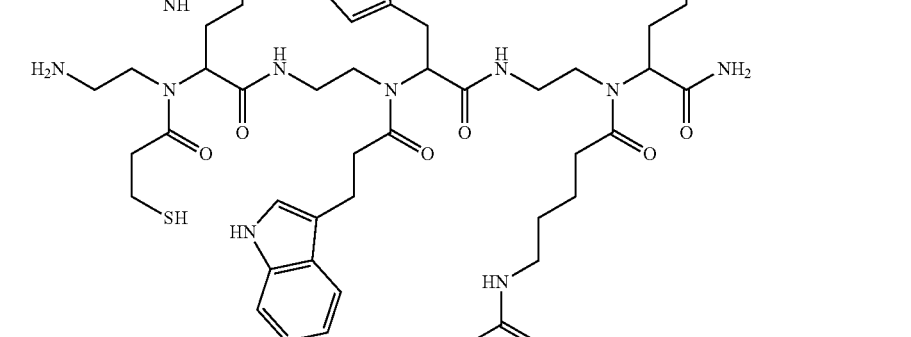 |
| Compound 4 | 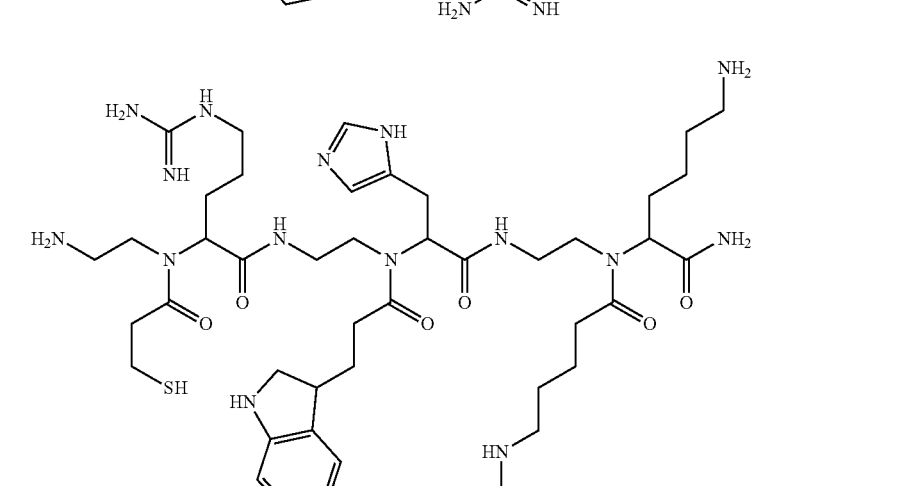 |
| Compound 5 | 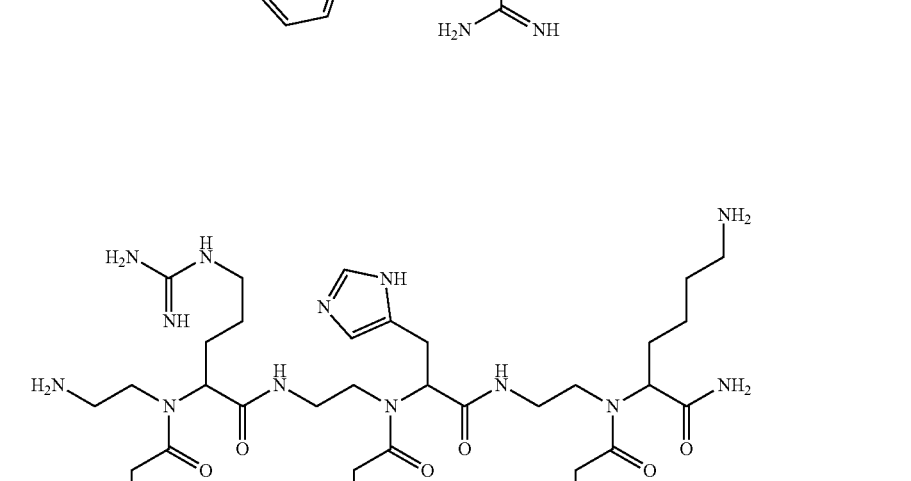 |

-continued

| Compound | Structure |
|---|---|
| Compound 6 | 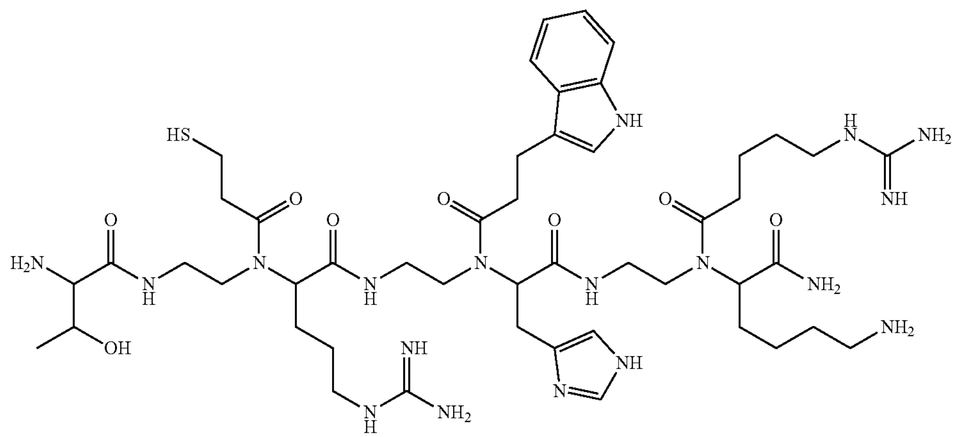 [SMILES: CC(O)C(N)C(=O)NCCN(C(=O)CCS)C(CCCNC(=N)N)C(=O)NCCN(C(=O)CCc1c[nH]c2ccccc12)C(Cc1c[nH]cn1)C(=O)NCCN(C(=O)CCCCNC(=N)N)C(CCCCN)C(N)=O] |
| Compound 7 | 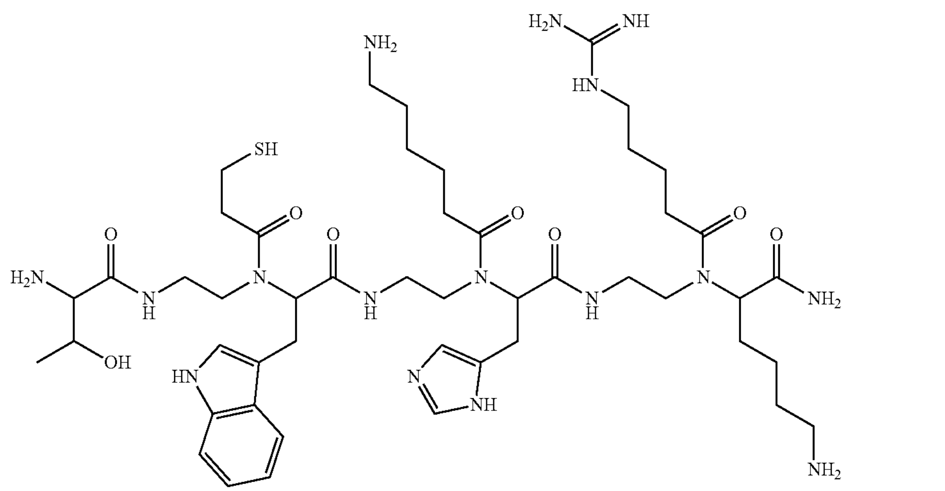 [SMILES: CC(O)C(N)C(=O)NCCN(C(=O)CCS)C(Cc1c[nH]c2ccccc12)C(=O)NCCN(C(=O)CCCCCN)C(Cc1cnc[nH]1)C(=O)NCCN(C(=O)CCCCNC(=N)N)C(CCCCN)C(N)=O] |
| Compound 8 | 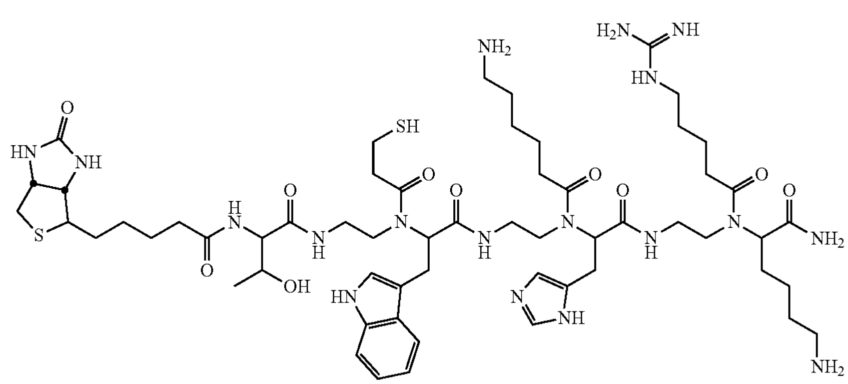 [SMILES: CC(O)C(NC(=O)CCCCC1SC[C@@H]2NC(=O)N[C@H]12)C(=O)NCCN(C(=O)CCS)C(Cc1c[nH]c2ccccc12)C(=O)NCCN(C(=O)CCCCCN)C(Cc1cnc[nH]1)C(=O)NCCN(C(=O)CCCCNC(=N)N)C(CCCCN)C(N)=O] |

| Compound | Structure |
|---|---|
| Compound 9 | 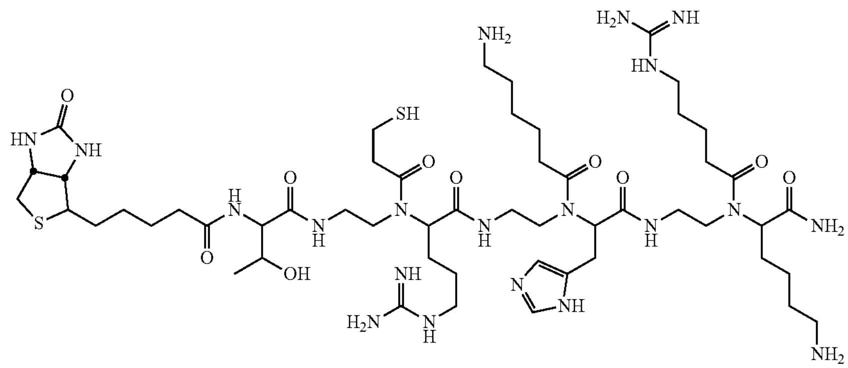 [SMILES: CC(O)C(NC(=O)CCCCC1SC[C@@H]2NC(=O)N[C@H]12)C(=O)NCCN(C(=O)CCS)C(CCCNC(=N)N)C(=O)NCCN(C(=O)CCCCCN)C(Cc1cnc[nH]1)C(=O)NCCN(C(=O)CCCCNC(=N)N)C(CCCCN)C(N)=O] |
| Compound 10 | 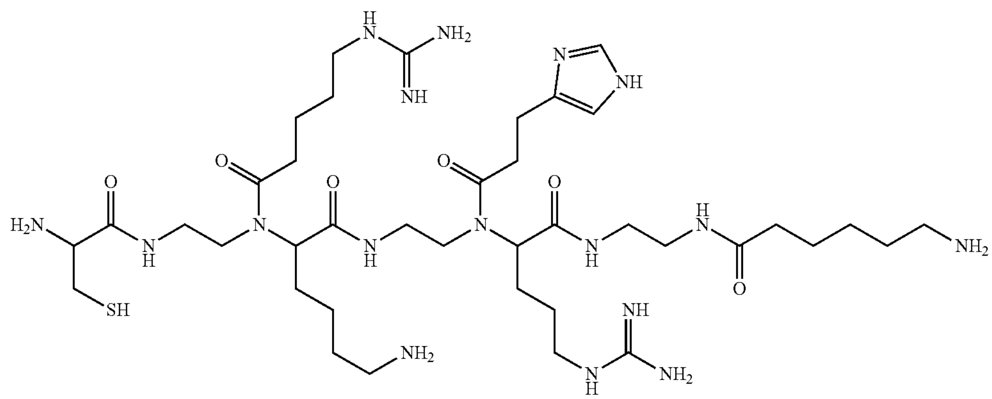 [SMILES: N=C(N)NCCCCC(=O)N(CCNC(=O)C(N)CS)C(CCCCN)C(=O)NCCN(C(=O)CCc1c[nH]cn1)C(CCCNC(=N)N)C(=O)NCCNC(=O)CCCCCN] |
| Compound 11 | 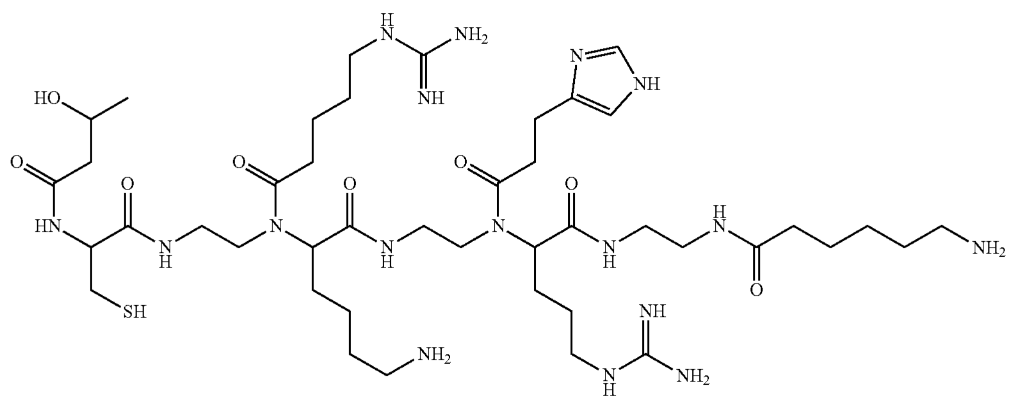 [SMILES: CC(O)CC(=O)NC(CS)C(=O)NCCN(C(=O)CCCCNC(=N)N)C(CCCCN)C(=O)NCCN(C(=O)CCc1c[nH]cn1)C(CCCNC(=N)N)C(=O)NCCNC(=O)CCCCCN] |
| Compound 12 | 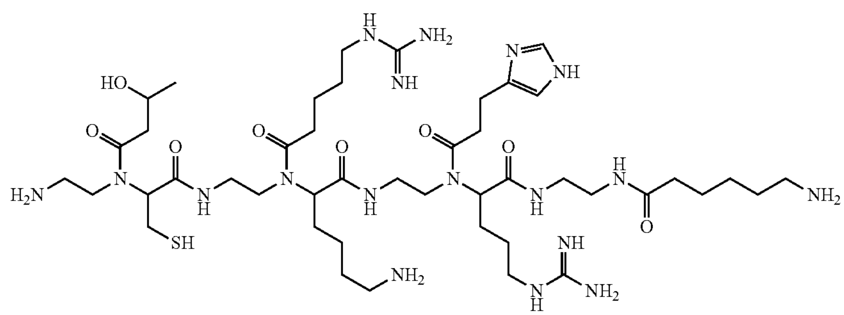 [SMILES: CC(O)CC(=O)N(CCN)C(CS)C(=O)NCCN(C(=O)CCCCNC(=N)N)C(CCCCN)C(=O)NCCN(C(=O)CCc1c[nH]cn1)C(CCCNC(=N)N)C(=O)NCCNC(=O)CCCCCN] |

| Compound | Structure |
|---|---|
| Compound 13 | 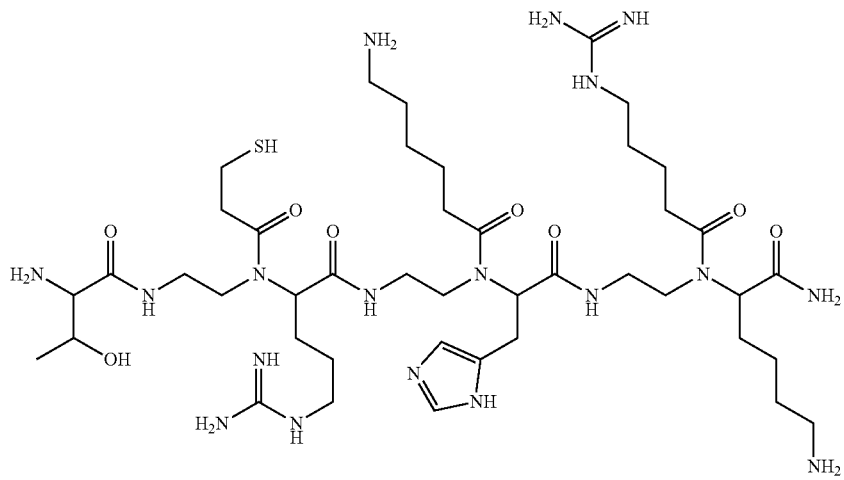 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCCCNC(=N)N)C(CCCCN)C(N)=O] |
| Compound 14 | 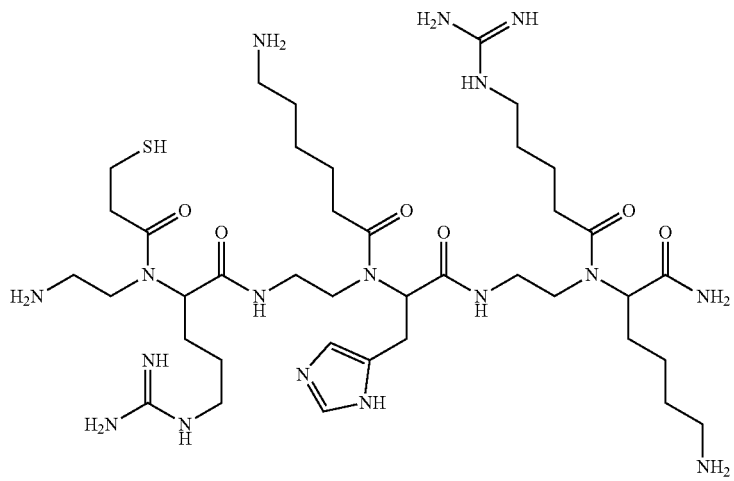 [SMILES: N=C(N)NCCCCC(=O)N(CCNC(=O)C(Cc1cnc[nH]1)N(CCNC(=O)C(CCCNC(=N)N)N(CCN)C(=O)CCS)C(=O)CCCCCN)C(CCCCN)C(N)=O] |
| Compound 15 | 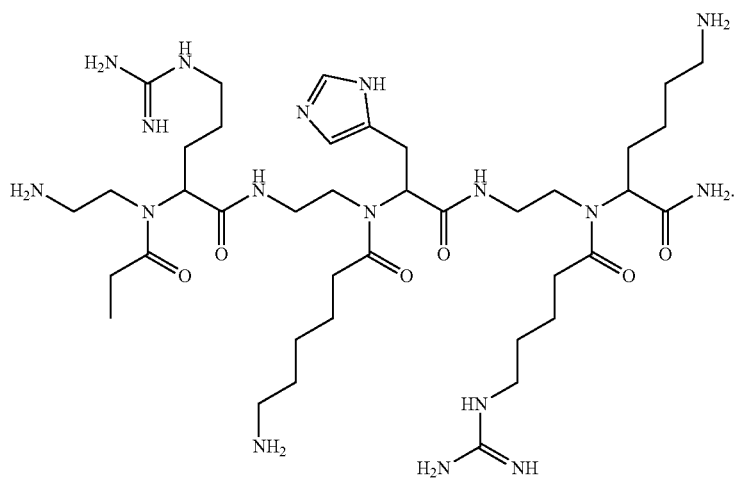 [SMILES: CCC(=O)N(CCN)C(CCCNC(=N)N)C(=O)NCCN(C(=O)CCCCCN)C(Cc1cnc[nH]1)C(=O)NCCN(C(=O)CCCCNC(=N)N)C(CCCCN)C(N)=O] |

| Compound | Structure |
|---|---|
| Compound 16 | 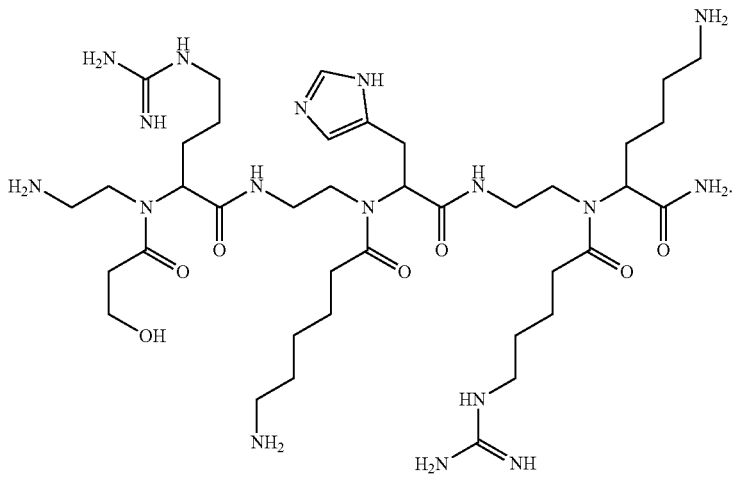 [SMILES: N=C(N)NCCCCC(=O)N(CCNC(=O)C(Cc1cnc[nH]1)N(CCNC(=O)C(CCCNC(=N)N)N(CCN)C(=O)CCO)C(=O)CCCCCN)C(CCCCN)C(N)=O] |
| Compound 17 | 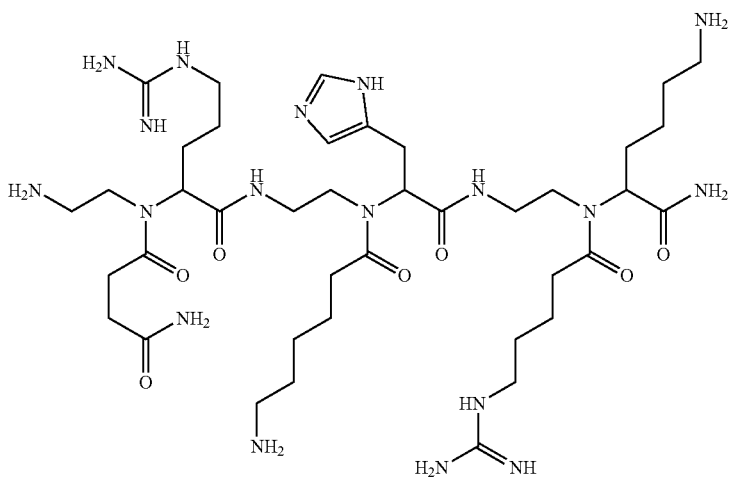 [SMILES: N=C(N)NCCCCC(=O)N(CCNC(=O)C(Cc1cnc[nH]1)N(CCNC(=O)C(CCCNC(=N)N)N(CCN)C(=O)CCC(N)=O)C(=O)CCCCCN)C(CCCCN)C(N)=O] |
| Compound 18 | 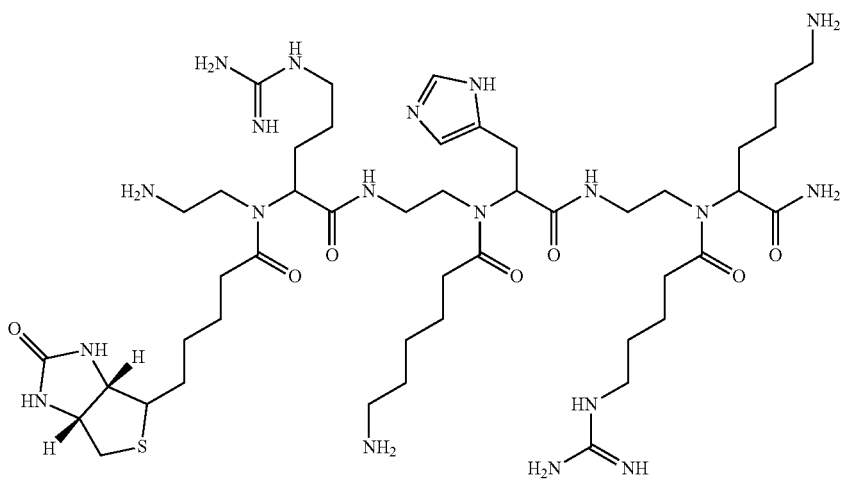 [SMILES: N=C(N)NCCCCC(=O)N(CCNC(=O)C(Cc1cnc[nH]1)N(CCNC(=O)C(CCCNC(=N)N)N(CCN)C(=O)CCCCC1SC[C@@H]2NC(=O)N[C@H]12)C(=O)CCCCCN)C(CCCCN)C(N)=O] |

-continued
| Compound | Structure |
|---|---|
| Compound 19 | 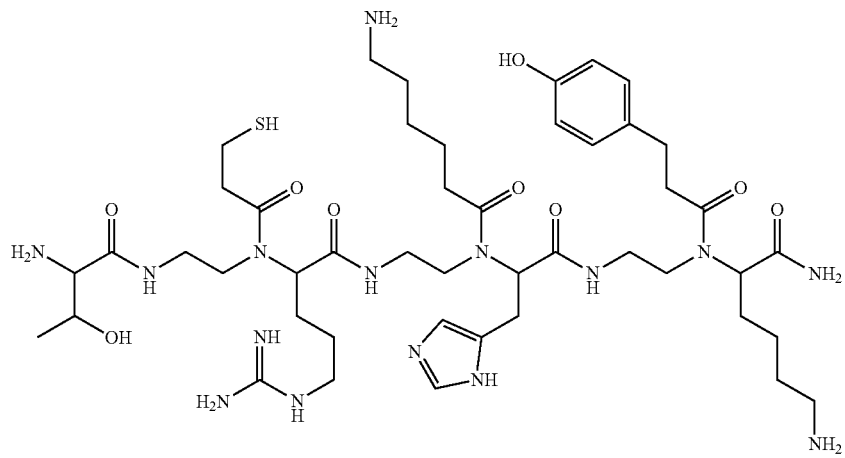 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCc1ccc(O)cc1)C(CCCCN)C(N)=O] |
| Compound 20 | 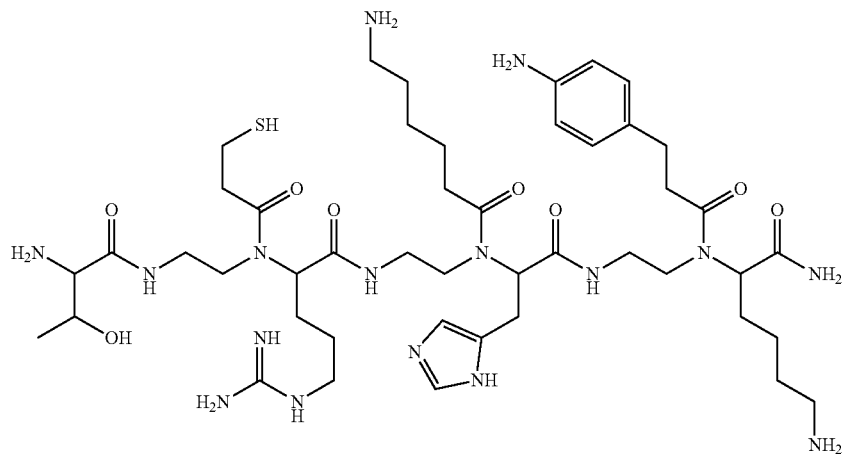 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCc1ccc(N)cc1)C(CCCCN)C(N)=O] |
| Compound 21 | 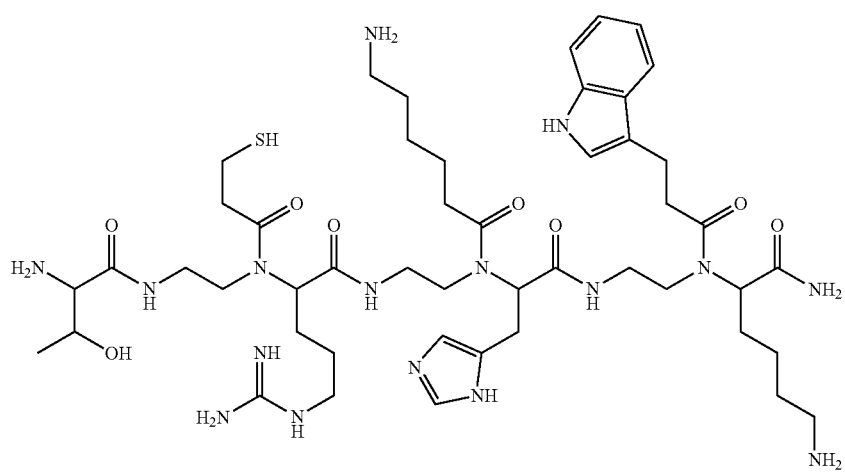 [SMILES: CC(O)C(N)C(=O)NCCN(C(=O)CCS)C(CCCNC(=N)N)C(=O)NCCN(C(=O)CCCCCN)C(Cc1cnc[nH]1)C(=O)NCCN(C(=O)CCc1c[nH]c2ccccc12)C(CCCCN)C(N)=O] |

| Compound | Structure |
|---|---|
| Compound 22 | (structure) |
| Compound 23 | (structure) |
| Compound 24 | (structure) |

| Compound | Structure |
|---|---|
| Compound 25 | 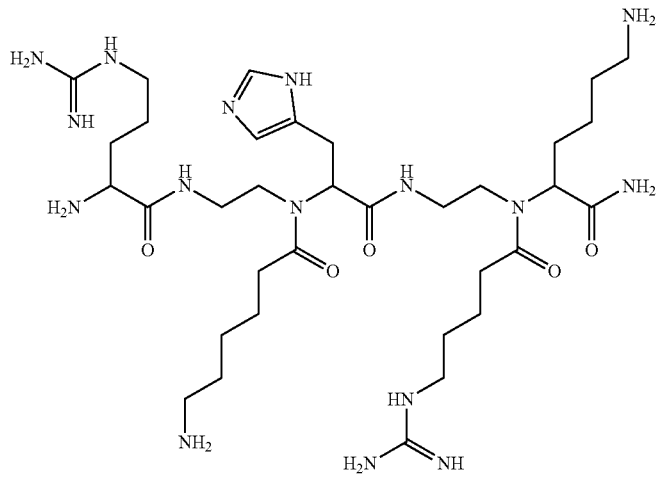 [SMILES: N=C(N)NCCCCC(=O)N(CCNC(=O)C(Cc1cnc[nH]1)N(CCNC(=O)C(N)CCCNC(=N)N)C(=O)CCCCCN)C(CCCCN)C(N)=O] |
| Compound 26 | 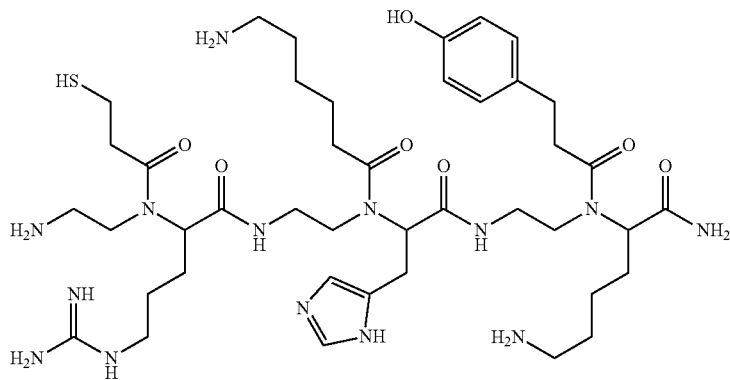 [SMILES: N=C(N)NCCCC(C(=O)NCCN(C(=O)CCCCCN)C(Cc1cnc[nH]1)C(=O)NCCN(C(=O)CCc1ccc(O)cc1)C(CCCCN)C(N)=O)N(CCN)C(=O)CCS] |
| Compound 27 | 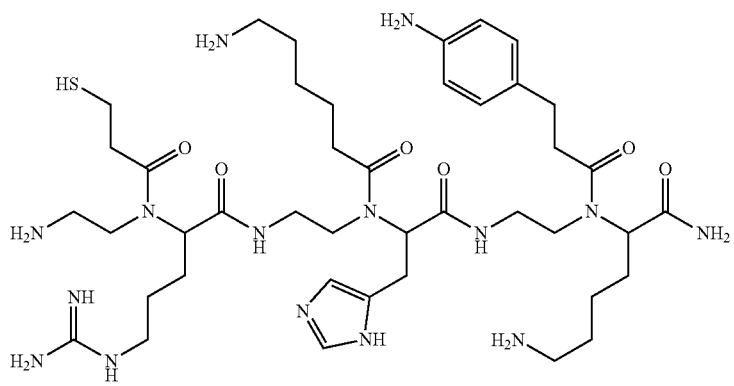 [SMILES: N=C(N)NCCCC(C(=O)NCCN(C(=O)CCCCCN)C(Cc1cnc[nH]1)C(=O)NCCN(C(=O)CCc1ccc(N)cc1)C(CCCCN)C(N)=O)N(CCN)C(=O)CCS] |

| Compound | Structure |
|---|---|
| Compound 28 | 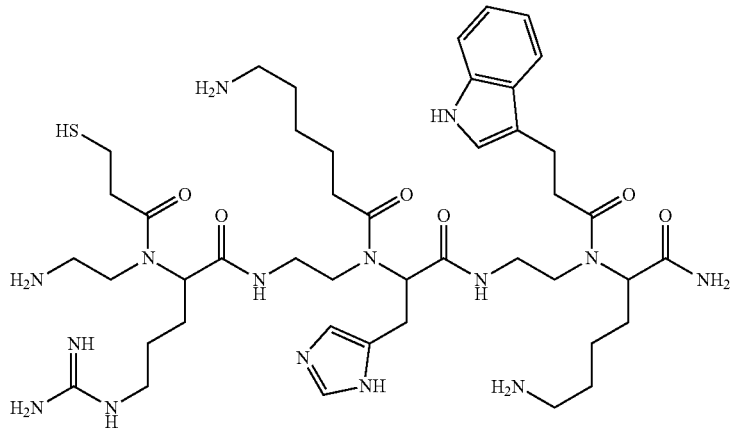 [SMILES: N=C(N)NCCCC(C(=O)NCCN(C(=O)CCCCCN)C(Cc1cnc[nH]1)C(=O)NCCN(C(=O)CCc1c[nH]c2ccccc12)C(CCCCN)C(N)=O)N(CCN)C(=O)CCS] |
| Compound 29 | 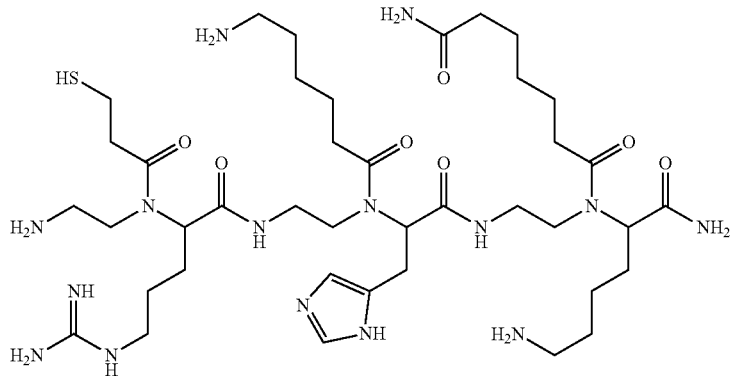 [SMILES: N=C(N)NCCCC(C(=O)NCCN(C(=O)CCCCCN)C(Cc1cnc[nH]1)C(=O)NCCN(C(=O)CCCCCC(N)=O)C(CCCCN)C(N)=O)N(CCN)C(=O)CCS] |
| Compound 30 | 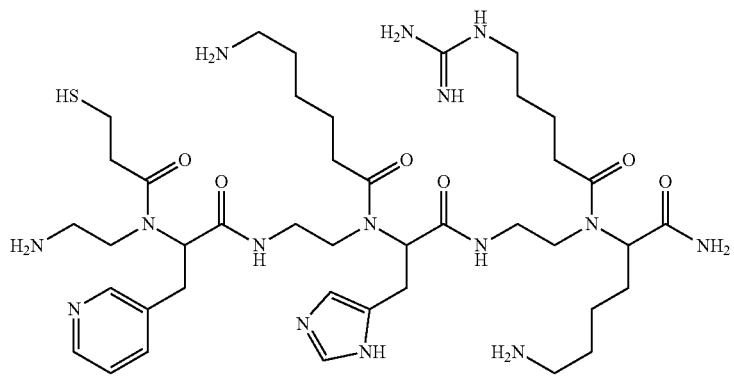 [SMILES: N=C(N)NCCCCC(=O)N(CCNC(=O)C(Cc1cnc[nH]1)N(CCNC(=O)C(Cc1cccnc1)N(CCN)C(=O)CCS)C(=O)CCCCCN)C(CCCCN)C(N)=O] |

| Compound | Structure |
|---|---|
| Compound 31 | 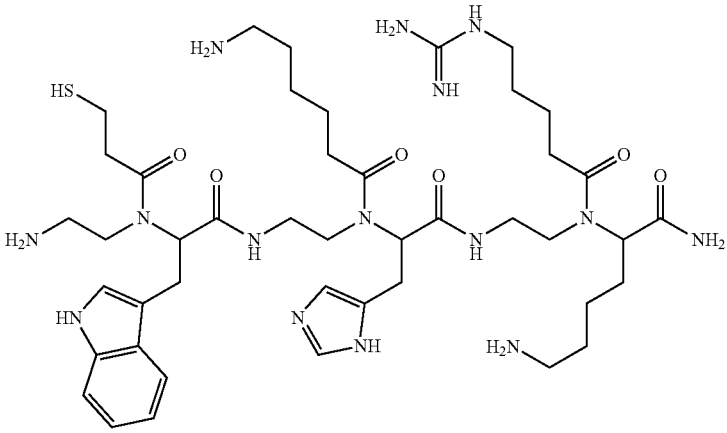 [SMILES: N=C(N)NCCCCC(=O)N(CCNC(=O)C(Cc1cnc[nH]1)N(CCNC(=O)C(Cc1c[nH]c2ccccc12)N(CCN)C(=O)CCS)C(=O)CCCCCN)C(CCCCN)C(N)=O] | or one of its salts;

said compound being in all the possible racemic, enantiomeric and diastereoisomeric isomer forms.

2. The compound according to claim 1, being selected from formula:

3. The compound according to claim 1, wherein said compound is grafted with one or several element(s) selected from the group consisting of a reactive moiety; a targeting agent; a dye; a fluorophore; a chemical tag; and an immunomodulating agent.

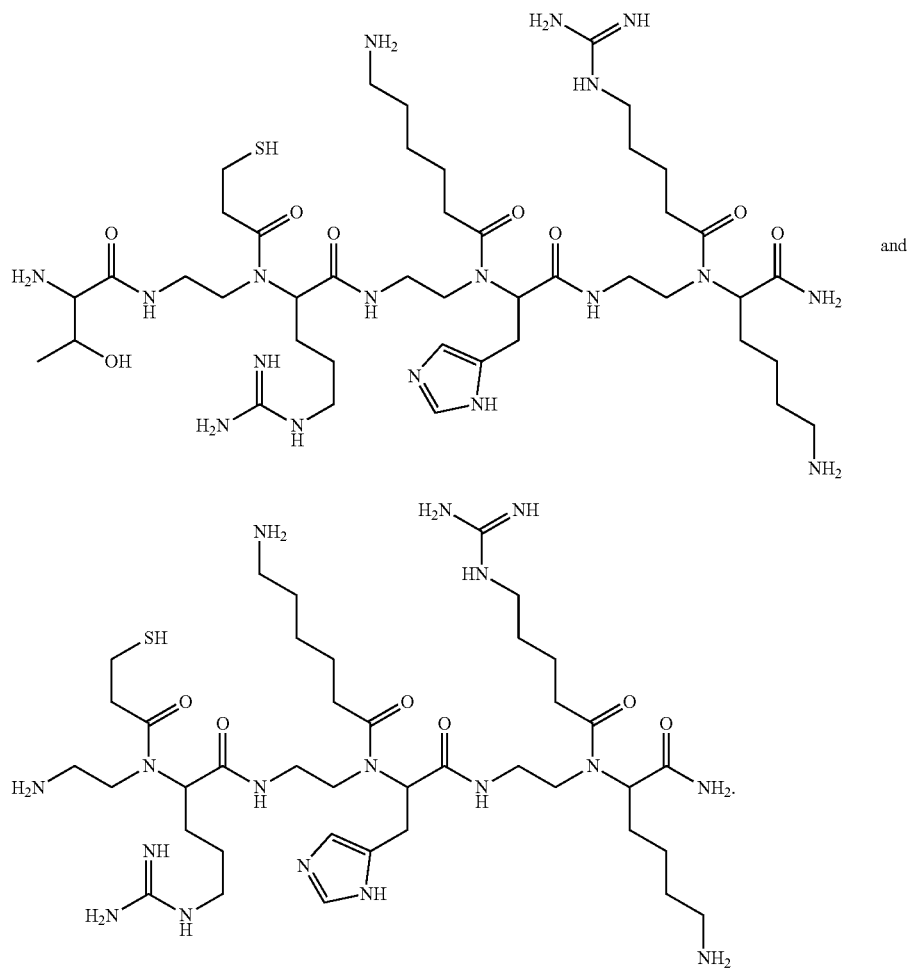

4. The compound according to claim 3, wherein the targeting agent is selected from PEG and biotin.

5. The compound according to claim 3, wherein the dye is a chromophore.

6. The compound according to claim 3, wherein the fluorophore is selected from rhodamine, fluorescein, BODIPY, indocyanine, and 3,6-bis(1-methyl-4-vinylpyridinium).

7. The compound according to claim 3, wherein the chemical tag is a ferrocenyl.

8. The compound according to claim 3, wherein the immunomodulating agent is pomalidomide.

9. The compound according to claim 8, wherein the pomalidomide comprises a PEG linker.

10. A pharmaceutical composition comprising, in a pharmaceutically acceptable medium, at least one compound according to claim 1.

11. A method for the reduction of CD95-mediated cell motility in a subject in need thereof comprising the administration to said subject of a compound according to claim 1, or a composition according to claim 10.

12. A method for the reduction of CD95 mediated cancer cell motility in a subject in need thereof comprising the administration to said subject of a compound according to claim 1 or a composition according to claim 10.

13. A method of treatment of cancer in a subject in need thereof, comprising the administration to said subject of a compound according to claim 1, or a composition according to claim 10, wherein the subject suffers from a cancer selected from the group consisting of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers.

14. A method for the reduction of CD95-mediated lymphocyte motility and/or B cell maturation in a subject in need thereof comprising the administration to said subject of a compound according to claim 1 or a composition according to claim 10.

15. A method for the treatment of an auto-immune inflammatory disease, comprising the administration of a compound according to claim 1 or a composition according to claim 10.

16. A method for the treatment of systemic lupus erythematosus, comprising the administration of a compound according to claim 1 or a composition according to claim 10.

17. A method for the treatment of antibody-mediated diseases selected from the list consisting of graft rejection, graft vs. host disease, and inflammatory-autoimmune diseases, comprising the administration of a compound according to claim 1, or a composition according to claim 10.

18. A method for treating metastases, comprising the administration of a compound according to claim 1, or a composition according to claim 10, in a subject in need thereof.

19. The method according to claim 18, wherein the subject suffers from a triple negative breast cancer.

* * * * *